US012421276B2

(12) United States Patent
Kawas et al.

(10) Patent No.: US 12,421,276 B2
(45) Date of Patent: Sep. 23, 2025

(54) METHODS OF TREATING NEURODEGENERATIVE DISEASE WITH SUBSTITUTED N-HEXANOIC-L-TYROSINE-L-ISOLEUCINE-(6)-AMINOHEXANOIC AMIDE ANALOGUES

(71) Applicant: Athira Pharma, Inc., Seattle, WA (US)

(72) Inventors: Leen H. Kawas, Seattle, WA (US); Jasbir Singh, Seattle, WA (US); Lansing Joseph Stewart, Seattle, WA (US); William R. Baker, Seattle, WA (US)

(73) Assignee: Athira Pharma, Inc., Bothell, WA (US)

( * ) Notice: Subject to any disclaimer, the term of this patent is extended or adjusted under 35 U.S.C. 154(b) by 1200 days.

(21) Appl. No.: 17/228,481

(22) Filed: Apr. 12, 2021

(65) Prior Publication Data

US 2021/0340176 A1    Nov. 4, 2021

Related U.S. Application Data

(62) Division of application No. 16/306,277, filed as application No. PCT/US2017/035547 on Jun. 1, 2017, now Pat. No. 11,021,514.

(60) Provisional application No. 62/344,305, filed on Jun. 1, 2016.

(51) Int. Cl.
  *C07K 5/065* (2006.01)
  *A61K 9/00* (2006.01)
  *C07K 5/02* (2006.01)

(52) U.S. Cl.
  CPC ........ *C07K 5/06078* (2013.01); *A61K 9/0019* (2013.01); *C07K 5/021* (2013.01)

(58) Field of Classification Search
  CPC combination set(s) only.
  See application file for complete search history.

(56) References Cited

U.S. PATENT DOCUMENTS

| | | |
|---|---|---|
| 4,477,440 A | 10/1984 | Boger et al. |
| 4,639,456 A | 1/1987 | Trouet et al. |
| 5,180,816 A | 1/1993 | Dean |
| 5,378,691 A | 1/1995 | Raddatz et al. |
| 5,382,569 A | 1/1995 | Cody et al. |
| 5,430,062 A | 7/1995 | Cushman et al. |
| 5,484,811 A | 1/1996 | Hanson et al. |
| 5,484,812 A | 1/1996 | Hanson et al. |
| 5,618,652 A | 4/1997 | Ueda et al. |
| 5,661,129 A | 8/1997 | Feelisch et al. |
| 5,686,419 A | 11/1997 | Powers et al. |
| 5,763,576 A | 6/1998 | Powers |
| 5,789,383 A | 8/1998 | Wirth et al. |
| 5,817,757 A | 10/1998 | Adams et al. |
| 5,831,004 A | 11/1998 | Campbell et al. |
| 5,840,698 A | 11/1998 | Campbell et al. |
| 5,854,388 A | 12/1998 | Harding et al. |
| 6,022,696 A | 2/2000 | Harding et al. |
| 6,121,489 A | 9/2000 | Dorner et al. |
| 6,242,563 B1 | 6/2001 | Dong |
| 6,348,570 B1 | 2/2002 | Chapman et al. |
| 6,468,977 B1 | 10/2002 | Karimian et al. |
| 6,867,192 B1 | 3/2005 | Armour et al. |
| 7,118,747 B2 | 10/2006 | Harding et al. |
| 7,795,378 B2 | 9/2010 | Sharma et al. |
| 7,910,555 B2 | 3/2011 | Harding et al. |
| 7,981,862 B2 | 7/2011 | Zamora et al. |
| 8,236,761 B2 | 8/2012 | Harding et al. |
| 8,598,118 B2 | 12/2013 | Harding et al. |
| 9,051,351 B2 | 6/2015 | Harding et al. |
| 9,066,901 B2 | 6/2015 | Harding et al. |
| 9,150,613 B2 | 10/2015 | Harding et al. |
| 9,475,854 B2 | 10/2016 | Coffin et al. |
| 9,611,297 B1 | 4/2017 | Leger et al. |
| 9,765,099 B2 | 9/2017 | McMurray et al. |
| 9,877,898 B2 | 1/2018 | Moszner et al. |
| 9,962,388 B2 | 5/2018 | Ding et al. |
| 9,969,719 B2 | 5/2018 | Ding et al. |
| 10,385,080 B2 | 8/2019 | McMurray et al. |

(Continued)

FOREIGN PATENT DOCUMENTS

| | | |
|---|---|---|
| CA | 2016355 A1 | 11/1990 |
| CA | 2075662 A1 | 2/1993 |
| CN | 102838523 A | 12/2012 |
| CN | 104788537 A | 7/2015 |
| CN | 108117582 A | 6/2018 |
| DE | 3320175 A1 | 12/1984 |
| DE | 3915361 A1 | 11/1990 |
| DE | 4122885 A1 | 1/1993 |
| DE | 4321306 A1 | 1/1995 |
| DE | 19914474 A1 | 10/1999 |

(Continued)

OTHER PUBLICATIONS

Deborah Heyl et al: "Peptide Inhibitors of a-Amylase Based on Tendamistat: Development of Analogues with [pi]-Amino Acids Linking Critical Binding Segments", Protein and Peptide Letters: international journal for rapid publication of short papers in protein and peptide science, vol. 12, No. 3, Apr. 1, 2005 (Apr. 1, 2005), pp. 275-280, XP55649610, NL, ISSN: 0929-8665, DOI: 10.2174/0929866053587110.

(Continued)

*Primary Examiner* — Adam Weidner
*Assistant Examiner* — Laura Ann Essex
(74) *Attorney, Agent, or Firm* — McNeill PLLC

(57) ABSTRACT

The present technology relates to compounds, kits, compositions, and methods useful for the treatment of numerous pathologies including dementia, Alzheimer's disease, Parkinson's disease, amyotrophic lateral sclerosis, and other neurodegenerative diseases, spinal cord injury, traumatic brain injury, diabetes and metabolic syndrome, defective wound healing, and/or sensorineural hearing and vision loss.

57 Claims, 2 Drawing Sheets

(56) References Cited

U.S. PATENT DOCUMENTS

| | | |
|---|---|---|
| 10,526,320 B2 | 1/2020 | Yuan et al. |
| 11,021,514 B2 | 6/2021 | Kawas et al. |
| 11,998,556 B2 | 6/2024 | Moebius et al. |
| 2001/0046668 A1 | 11/2001 | Levine et al. |
| 2004/0001801 A1 | 1/2004 | Madison et al. |
| 2005/0238993 A1 | 10/2005 | Watanabe et al. |
| 2006/0063803 A1 | 3/2006 | Ruggeri et al. |
| 2006/0172952 A1 | 8/2006 | Powers et al. |
| 2006/0233748 A1 | 10/2006 | Merzouk et al. |
| 2006/0241057 A1 | 10/2006 | Powers et al. |
| 2007/0116669 A1 | 5/2007 | Merzouk et al. |
| 2007/0117821 A1 | 5/2007 | Ding et al. |
| 2007/0160574 A1 | 7/2007 | Merzouk et al. |
| 2008/0293634 A1 | 11/2008 | Harding et al. |
| 2009/0048238 A1 | 2/2009 | Aebi et al. |
| 2009/0111152 A1 | 4/2009 | Sherman et al. |
| 2009/0186902 A1 | 7/2009 | Merla et al. |
| 2009/0270423 A1 | 10/2009 | Blackwell et al. |
| 2010/0228004 A1 | 9/2010 | Prabhakaran |
| 2012/0142786 A1 | 6/2012 | Goralczyk et al. |
| 2013/0023475 A1 | 1/2013 | Harding et al. |
| 2013/0165392 A1 | 6/2013 | Harding et al. |
| 2013/0281484 A1 | 10/2013 | Kozikowski et al. |
| 2014/0051633 A1 | 2/2014 | Harding et al. |
| 2014/0094413 A1* | 4/2014 | Harding ............... A61K 38/05 514/17.7 |
| 2014/0162937 A1 | 6/2014 | Vaara et al. |
| 2015/0337024 A1 | 11/2015 | Coffin et al. |
| 2015/0357204 A1 | 12/2015 | Ogihara et al. |
| 2016/0009763 A1 | 1/2016 | Lin et al. |
| 2016/0122386 A1 | 5/2016 | Wisniewski et al. |
| 2017/0022149 A1 | 1/2017 | Nguyen |
| 2017/0196830 A1 | 7/2017 | Shanahan et al. |
| 2018/0000897 A1 | 1/2018 | Rusanescu |
| 2018/0072717 A1 | 3/2018 | Liu et al. |
| 2018/0291063 A1 | 10/2018 | Cai et al. |
| 2018/0305360 A1 | 10/2018 | Barrow et al. |
| 2018/0340008 A1 | 11/2018 | Bassiri et al. |
| 2020/0054622 A1 | 2/2020 | Braithwaite et al. |
| 2024/0277735 A1 | 8/2024 | Moebius et al. |

FOREIGN PATENT DOCUMENTS

| | | |
|---|---|---|
| EP | 0163237 A2 | 4/1988 |
| EP | 0126974 A1 | 6/1988 |
| EP | 0355065 A1 | 2/1990 |
| EP | 0393445 A2 | 10/1990 |
| EP | 0412350 A2 | 3/1992 |
| EP | 0497366 A2 | 8/1992 |
| EP | 0457195 A2 | 11/1992 |
| EP | 0498940 A2 | 1/1993 |
| EP | 0528487 A2 | 2/1993 |
| EP | 0519748 A2 | 5/1993 |
| EP | 0547699 A1 | 6/1993 |
| EP | 0600832 A1 | 6/1994 |
| EP | 0661058 A1 | 7/1995 |
| EP | 0731107 A1 | 9/1996 |
| EP | 1059302 A1 | 12/2000 |
| EP | 0443429 A1 | 6/2002 |
| EP | 0987251 A1 | 5/2004 |
| EP | 1932852 A1 | 10/2008 |
| EP | 1867667 A1 | 10/2012 |
| EP | 2746262 A1 | 6/2014 |
| EP | 3345917 A1 | 7/2018 |
| FR | 2778406 A1 | 5/2003 |
| GB | 2292149 A | 2/1996 |
| GB | 2324529 A | 10/1998 |
| JP | 05117169 A | 5/1993 |
| JP | 05178890 A | 7/1993 |
| JP | 06192199 A | 7/1994 |
| JP | 08262673 A | 10/1996 |
| JP | 2000250182 A | 9/2000 |
| JP | 2002145898 A | 5/2002 |
| JP | 2007524598 A | 8/2007 |
| JP | 2007530003 A | 11/2007 |
| JP | 2014511858 A | 5/2014 |
| JP | 2015151458 A | 8/2015 |
| WO | 8704349 A1 | 7/1987 |
| WO | 9005531 A1 | 5/1990 |
| WO | 9213952 A1 | 8/1992 |
| WO | 9220706 A1 | 11/1992 |
| WO | 9221361 A1 | 12/1992 |
| WO | 9312076 A1 | 6/1993 |
| WO | 9314777 A1 | 8/1993 |
| WO | 9316710 A1 | 9/1993 |
| WO | 9323357 A1 | 11/1993 |
| WO | 94000492 | 1/1994 |
| WO | 9406451 A1 | 3/1994 |
| WO | 9414817 A1 | 7/1994 |
| WO | 9422491 A1 | 10/1994 |
| WO | 9422906 A1 | 10/1994 |
| WO | 9428012 A1 | 12/1994 |
| WO | 9513289 A1 | 5/1995 |
| WO | 9616079 A2 | 5/1996 |
| WO | 9633209 A1 | 10/1996 |
| WO | 9633268 A1 | 10/1996 |
| WO | 9640204 A1 | 12/1996 |
| WO | 9640738 A1 | 12/1996 |
| WO | 9703093 A1 | 1/1997 |
| WO | 9708193 A1 | 3/1997 |
| WO | 9716410 A1 | 5/1997 |
| WO | 9740071 A1 | 10/1997 |
| WO | 9812214 A1 | 3/1998 |
| WO | 9812219 A1 | 3/1998 |
| WO | 9822496 A2 | 5/1998 |
| WO | 9827094 A1 | 6/1998 |
| WO | 9829435 A1 | 7/1998 |
| WO | 9931052 A1 | 6/1999 |
| WO | 9932509 A2 | 7/1999 |
| WO | 0005260 A1 | 2/2000 |
| WO | 2001025210 A2 | 10/2001 |
| WO | 2001079263 A1 | 10/2001 |
| WO | 02040016 A2 | 5/2002 |
| WO | 02055543 A2 | 7/2002 |
| WO | 02060432 A1 | 8/2002 |
| WO | 02095007 A2 | 11/2002 |
| WO | 2003053988 A2 | 12/2003 |
| WO | 2004005270 A1 | 1/2004 |
| WO | 2004005324 A2 | 3/2004 |
| WO | 2004018644 A2 | 3/2004 |
| WO | 2004078778 A3 | 11/2004 |
| WO | 2004099124 A2 | 11/2004 |
| WO | 2005017107 A2 | 2/2005 |
| WO | 2005039617 A1 | 5/2005 |
| WO | 2005014623 A2 | 9/2005 |
| WO | 2005080353 A1 | 9/2005 |
| WO | 2005105829 A1 | 11/2005 |
| WO | 2005113580 A1 | 12/2005 |
| WO | 2006061714 A2 | 6/2006 |
| WO | 2007031343 A1 | 3/2007 |
| WO | 2007047991 A1 | 4/2007 |
| WO | 2007048642 A1 | 5/2007 |
| WO | 2007144196 A2 | 12/2007 |
| WO | 2008000512 A2 | 1/2008 |
| WO | 2008000513 A2 | 1/2008 |
| WO | 2008005531 A1 | 6/2008 |
| WO | 2008068487 A1 | 6/2008 |
| WO | 2007070372 A2 | 7/2008 |
| WO | 2007144195 A2 | 9/2008 |
| WO | 2008120098 A2 | 10/2008 |
| WO | 2009003003 A2 | 12/2008 |
| WO | 2009003861 A1 | 1/2009 |
| WO | 2009099677 A2 | 8/2009 |
| WO | 2009103652 A1 | 8/2009 |
| WO | 2009105782 A1 | 8/2009 |
| WO | 2009114950 A1 | 9/2009 |
| WO | 2010014179 A1 | 2/2010 |
| WO | 2010022171 A1 | 2/2010 |
| WO | 2010039461 A2 | 7/2010 |
| WO | 2010080605 A1 | 7/2010 |
| WO | 2010080609 A1 | 7/2010 |
| WO | 2010042212 A2 | 9/2010 |
| WO | 2010138659 A1 | 12/2010 |

(56) References Cited

FOREIGN PATENT DOCUMENTS

| | | | |
|---|---|---|---|
| WO | 2010138685 | A1 | 12/2010 |
| WO | 2010138695 | A1 | 12/2010 |
| WO | 2010138706 | A1 | 12/2010 |
| WO | 2010138758 | A1 | 12/2010 |
| WO | 2010138652 | A1 | 1/2011 |
| WO | 2011011303 | A1 | 1/2011 |
| WO | 2011038066 | A2 | 3/2011 |
| WO | 2010151644 | A2 | 5/2011 |
| WO | 2011038061 | A2 | 7/2011 |
| WO | 2011088345 | A1 | 7/2011 |
| WO | 2011075471 | A2 | 1/2012 |
| WO | 2012020219 | A2 | 2/2012 |
| WO | 2012026988 | A2 | 3/2012 |
| WO | 2012032085 | A1 | 3/2012 |
| WO | 2012122422 | A2 | 9/2012 |
| WO | 2012138599 | A2 | 1/2013 |
| WO | 2013001297 | A1 | 1/2013 |
| WO | 2013063468 | A1 | 5/2013 |
| WO | 2013030569 | A2 | 6/2013 |
| WO | 2013123456 | A1 | 8/2013 |
| WO | 2013128003 | A1 | 9/2013 |
| WO | 2013152298 | A1 | 10/2013 |
| WO | 2013170113 | A1 | 11/2013 |
| WO | 2013170115 | A1 | 11/2013 |
| WO | 2013190520 | A2 | 12/2013 |
| WO | 2013170077 | A2 | 3/2014 |
| WO | 2012122420 | A2 | 4/2014 |
| WO | 2014049610 | A2 | 4/2014 |
| WO | 2014052766 | A1 | 4/2014 |
| WO | 2014067746 | A1 | 5/2014 |
| WO | 2014074789 | A1 | 5/2014 |
| WO | 2014091268 | A1 | 6/2014 |
| WO | 2014139008 | A1 | 9/2014 |
| WO | 2014143241 | A1 | 9/2014 |
| WO | 2014145090 | A1 | 9/2014 |
| WO | 2014207556 | A1 | 12/2014 |
| WO | 2014182928 | A2 | 1/2015 |
| WO | 2015023898 | A1 | 2/2015 |
| WO | 2015073769 | A1 | 5/2015 |
| WO | 2015091795 | A1 | 6/2015 |
| WO | 2015124797 | A1 | 8/2015 |
| WO | 2015166348 | A1 | 11/2015 |
| WO | 2016001319 | A1 | 1/2016 |
| WO | 2016008946 | A1 | 1/2016 |
| WO | 2016023511 | A1 | 2/2016 |
| WO | 2016049174 | A1 | 3/2016 |
| WO | 2016097405 | A1 | 6/2016 |
| WO | 2016123576 | A1 | 8/2016 |
| WO | 2016141881 | A1 | 9/2016 |
| WO | 2016150576 | A1 | 9/2016 |
| WO | 2016178979 | A1 | 11/2016 |
| WO | 2016182898 | A1 | 11/2016 |
| WO | 2017005902 | A1 | 1/2017 |
| WO | 2017106643 | A1 | 6/2017 |
| WO | 2017129331 | A1 | 8/2017 |
| WO | 2017151587 | A1 | 9/2017 |
| WO | 2017151886 | A1 | 9/2017 |
| WO | 2017172881 | A1 | 10/2017 |
| WO | 2017181004 | A1 | 10/2017 |
| WO | 2017201433 | A1 | 11/2017 |
| WO | 2017210188 | A1 | 12/2017 |
| WO | 2017210489 | A1 | 12/2017 |
| WO | 2017217855 | A1 | 12/2017 |
| WO | 2018010656 | A1 | 1/2018 |
| WO | 2018014862 | A1 | 1/2018 |
| WO | 2018035615 | A1 | 3/2018 |
| WO | 2018035617 | A1 | 3/2018 |
| WO | 2018060216 | A1 | 4/2018 |
| WO | 2018122419 | A1 | 7/2018 |
| WO | 2018136646 | A1 | 7/2018 |
| WO | 2018152633 | A1 | 8/2018 |
| WO | 2018174831 | A1 | 9/2018 |
| WO | 2019157527 | A2 | 8/2019 |

OTHER PUBLICATIONS

European Search Report corresponding to European Patent Application No. 17807519.8, mailed Jan. 10, 2020, Examiner A. Schleifenbaum, 7 pages.

International Search Report and Written Opinion for International Application No. PCT/US2017/035547 dated Oct. 18, 2017, 11 pages.

Jin-Mi Noh et al: "Kojic acid-tripeptide amide as a new tyrosinase inhibitor", Biopolymers, vol. 88, No. 2, Jan. 1, 2007 (Jan. 1, 2007), pp. 300-307, XP55649603, US ISSN: 0006-3525, DOI: 10.1002/bip.20670.

McCoy et al., "Evaluation of Metabolically Stabilized Angiotensin IV Analogs as Procognitive/Antidementia Agents," Journal of Pharmacology and Experimental Therapeutics (Jan. 31, 2013), 344(1), pp. 141-154.

Pacofsky et al, "Potent Dipeptide Inhibitors of the pp60 c=src domain," J. Med. Chem 1998, 41, pp. 1894-1908.

Zhang et al, "Structural analysis of angiotensin IV receptor (AT4) from selected bovine tissues," Journal of Pharmacology and Experimental Therapeutics (1999), 289(2), pp. 1075-1083.

Benoist et al., "The Procognitive and Synaptogenic Effects of Angiotensin IV-Derived Peptides Are Dependent on Activation of the Hepatocyte Growth Factor/c-Met System," The Journal of Pharmacology and Experimental Therapeutics, 351:390-402, Nov. 2014.

Kawas et al., "Development of Angiotensin IV Analogs as Hepatocyte Growth Factor/Met Modifiers," The Journal of Pharmacology and Experimental Therapeutics, vol. 340, No. 3, 2012, pp. 539-548.

Kawas et al., "Mimics of the Dimerization Domain of Hepatocyte Growth Factor Exhibit Anti-Met and Anticancer Activity," The Journal of Pharmacology and Experimental Therapeutics, vol. 339, No. 2, Aug. 2011, pp. 509-518 and supplemental figures 1-3 and Erratum.

Kawas et al., "Nanoscale mapping of the Met receptor on hippocampal neurons by AFM and confocal microscopy," Nanomedicine: Nanotechnology, Biology and Medicine, vol. 9, Issue 3, Apr. 2013, pp. 428-438.

Pasricha, "Athira Pharma's shares plunge after Bothell company's CEO placed on leave," Jun. 18, 2021, The Seattle Times, pp. 1-3.

PubPeer, Jul. 13, 2021 [online]. Retrieved from the internet: https://pubpeer.com/publications/01199F548BE82EE44C7D395568982B, "Development of angiotensin IV analogs as hepatocyte growth factor/Met modifiers," pp. 1-5.

PubPeer, Jul. 13, 2021 [online]. Retrieved from the internet: https://pubpeer.com/publications/36F84FDB31C718C8CF8F52C717D15C, "Nanoscale mapping of the Met receptor on hippocampal neurons by AFM and confocal microscopy," pp. 1-8.

PubPeer, Jul. 13, 2021 [online]. Retrieved from the internet: https://pubpeer.com/publications/4D8EFBD349D1A779627479FB694F7C, "Evaluation of metabolically stabilized angiotensin IV analogs as brocognitive/antidementia agents, " pp. 1-2.

PubPeer, Jul. 13, 2021 [online]. Retrieved from the internet: https://pubpeer.com/publications/51C554512CE22267B2E62172DF3DDE, "Mimics of the dimerization domain of hepatocyte growth factor exhibit anti-Met and anticancer activity," pp. 1-8.

PubPeer, Jul. 13, 2021 [online]. Retrieved from the internet: https://pubpeer.com/publications/56408F27C1C94294C69E8466C44C2B, "Plasma phospholipids identify antecedent memory impairment In older adults," pp. 1-3.

PubPeer, Jul. 13, 2021 [online]. Retrieved from the internet: https://pubpeer.com/publications/D5375331091A7EF887CDC02B813ACA, "The Procognitive and Synaptogenic Effects of Angiotensin IV-Derived Peptides Are Dependent on Activation of the Hepatocyte Growth Factor/c-Met System," pp. 1-6.

PubPeer, Jul. 13, 2021 [online]. Retrieved from the internet: https://pubpeer.com/publications/

(56) References Cited

OTHER PUBLICATIONS

D803673763EF5404FAE8CC546CC028, "Hepatocyte growth factor mimetic protects lateral line hair cells from aminoglycoside exposure," pp. 1-2.
PubPeer, Jun. 16, 2021 [online]. Retrieved from the internet: https://pubpeer.com/search?q=Kawas, pp. 1-2.
Schneider, "For Better Science," Jun. 15, 2021, 32 pages.
Athira Pharma Press Release, "Athira Pharma Announces Topline Results from Phase 2/3 LIFT-AD Clinical Trial of Fosgonimeton for Mild-to-Moderate Alzheimer's Disease", Sep. 3, 2024, 3 pages.
Athira Pharma Press Release, "Athira Pharma to Focus on Advancement of ATH-1105 for the Treatment of Neurodegenerative Diseases", Sep. 17, 2024, 2 pages.
Maina, F., et al., "Hepatocyte growth factor, a versatile signal for developing neurons", Nature Neuroscience 2, 1999, 213-217 (5 pgs).
Mattsson, N., et al., "Association Between Longitudinal Plasma Neurofilament Light and Neurodegeneration in Patients With Alzheimer Disease", JAMA Neurol 76, 2019, 791-799 (9 pgs.)
McKhann G.M., et al., "The diagnosis of dementia due to Alzheimer's disease: recommendations from the National Institute on Aging-Alzheimer's Association workgroups on diagnostic guidelines for Alzheimer's disease", Alzheimers Dement 7, 2011, 263-9 (11 pgs.)
Mehta, C.R., et al., "Adaptive increase in sample size when interim results are promising: A practical guide with examples", Statist. Med., 30, 2000, 3267-3284 (20 pgs.)
Meraz-Rios, M.A., et al., "Inflammatory process in Alzheimer's Disease", Front Integr Neurosci 7 (article 59), 2013, 1-15 (15 pgs).
Moebius et al., "ACT-AD: Fosgonimeton in Mild-to-Moderate Alzheimer's Disease—First Results of a Randomized, Placebo-Controlled, 26-Week, Phase 2 Proof-of-Concept Trial", 2022, 13 pages.
Moebius, H., et al., "Fosgonimeton Provides Congruent Benefit on Diverse Biomarkers of Neurodegeneration, Significantly Correlating With a Composite Clinical Score of Cognition and Function in Alzheimer's Disease", 2022, 2 pages.
Molnarfi, N., et al., "Hepatocyte growth factor: A regulator of inflammation and autoimmunity", Autoimmun Rev 14, 2015, 293-303 (12 pgs.)
Muir, J.L., "Acetylcholine, aging, and Alzheimer's disease", Pharmacol Biochem Behav 56, 1997, 687-696 (10 pgs)
Nazem, A., et al., "Rodent models of neuroinflammation for Alzheimer's disease", J Neuroinflammation 12, 74, 2015, 15 pgs.
Noh, M.Y., et al., "Neuroprotective effects of donepezil through inhibition of GSK-3activity in amyloid-beta-induced neuronal cell death", J Neurochem 108, 2009, 1116-1125 (10 pgs.)
Okaichi, H., et al., "Scopolamine impairs both working and reference memory in rats: a replication and extension", Pharmacol Biochem Behav 34, 1989, 599-602 (4 pgs.)
Olichney, J.M., et al., "Predictive Power of Cognitive Biomarkers in Neurodegenerative Disease Drug Development: Utility of the P300 Event-Related Potential", Neural Plast 2104880, 2022, 13 pgs.
Osborn, L.M., et al., "Astrogliosis: An integral player in the pathogenesis of Alzheimer's disease", Prog Neurobiol 144, 2016, 121-141 (21 pgs.)
Park, SA., et al., "Promising Blood Biomarkers for Clinical Use in Alzheimer's Disease: A Focused Update", J Clin Neurol 18, 2022, 401-409 (9 pgs.)
Pasqualetti, G., et al., "The Role of Neuroinflammation in Dementias", Curr Neurol Neurosci Rep 15, 17, 2015, 11 pgs.
Ramesh, V., et al., "Biphasic responses in cell signalling: A unified approach", bioRxiv, 2023, 28 pgs.
Raz, L., et al., "The neuropathology and cerebrovascular mechanisms of dementia", J Cereb Blood Flow Metab. 1, 2016, 172-186 (15 pgs.)
Riekkinen, P., et al., "Effects of scopolamine infusions into the anterior and posteriorcingulate on passive avoidance and water maze navigation", Brain Res 685, 46-54 (9 pgs.)

Salvadó G., et al., "Specific associations between plasma biomarkers and post-mortem amyloid plaque and neurofibrillary tau tangle loads", medRxiv, 2022, 38 pgs.
Selkoe, D. J., "Alzheimer's disease is a synaptic failure", Science 298, 2002, 789-91 (3 pgs.)
Serrano-Pozo, A., et al., "Neuropathological alterations in Alzheimer disease", Cold Spring Harb Perspect Med 1, a006189, 2011, 24 pages.
Shang, J., et al., "Strong neurogenesis, angiogenesis, synaptogenesis, and antifibrosis of hepatocyte growth factor in rats brain after transient middle cerebral arteryocclusion", J Neurosci Res 89, 2011, 86-95 (10 pgs.)
Shen, H., et al., "Neuroprotection by donepezil against glutamate excitotoxicity involves stimulation of alpha7 nicotinic receptors and internalization of NMDA receptors", Br J Pharmacol 161, 2010, 127-39 (13 pgs.)
Shulman, Y., et al., "ATP binding to synapsin IIa regulates usage and clustering of vesicles in terminals of hippocampal neurons", J Neurosci 35, 2015, 985-98 (14 pgs.)
Stancu, I.C, et al., "Models of B-Amyloid Induced Tau-Pathology: The Long and 'Folded' Road to Understand the Mechanism", Molecular Neurodegeneration, 9, 51, 2014, 14 pgs.
Stoiljkovic, M., et al., "Therapy for Alzheimer's disease: Missing targets and functional markers?", Ageing Res Rev 68, 101318, 2021, 15 pgs.
Sun, W., et al., "Overexpression of HGF retards disease progression and prolongs lifespan in a transgenic mouse model of ALS", J Neurosci. 22, 6537-6548 (12 pgs.)
Takada-Takatori, Y., et al., "Acetylcholinesterase inhibitors used in treatment of Alzheimer's disease prevent glutamate neurotoxicity via nicotinic acetylcholine receptors and phosphatidylinositol 3-kinase cascade", Neuropharmacology 51, 2006, 474-486 (13 pgs.)
Takada-Takatori, Y., et al., "Mechanism of neuroprotection by donepezil pretreatment in rat cortical neurons chronically treated with donepezil", J Neurosci Res86, 2008, 3575-3583 (9 pgs.)
Takeuchi, D., et al., "Alleviation of Aβ-induced cognitive impairment by ultrasound-mediated gene transfer of HGF in a mouse model", Gene Ther15, 2008, 561-571 (11 pgs.)
Tancredi, V., et al., "The inhibitory effects of interleukin-6 on synaptic plasticity in the rat hippocampus are associated with an inhibition of mitogen-activated protein kinase Erk", J Neurochem 75, 2000, 634-43 (10 pgs).
Thomas, A., et al., "Donepezil, rivastigmine, and vitamin E in Alzheimer disease: a combined P300 event-related potentials/neuropsychologic evaluation over 6 months", Clin Neuropharmacol 24, 2001, 31-42 (12 pgs.)
Tulasne, D., et al., "The shadow of death on the MET tyrosine kinase receptor", Cell Death Differ 15, 2008, 427-34 (8 pgs.)
Tyndall, S.J., et al., "Hepatocyte growth factor-induced enhancement of dendritic branching is blocked by inhibitors of N-methyl-D-aspartate receptors and calcium/calmodulin-dependent kinases", J Neurosci Res 85, 2007, 2343-2351 (9 pgs.)
Wang, T., et al., "Hepatocyte growth factor acts as a mitogen and chemoattractant for postnatal subventricular zone-olfactory bulb neurogenesis", Mol Cell Neurosci48, 2011, 38-50 (24 pgs.)
Wilczynska, K, et al., "Diagnostic Utility of Selected Serum Dementia Biomarkers: Amyloid β-40, Amyloid β-42, Tau Protein, and YKL-40: A Review", J Clin Med 9, 3452, 2020, 26 pgs.
Xiao, G.H., et al., "Anti-apoptotic signaling by hepatocyte growth factor/Met via the phosphatidylinositol 3-kinase/Akt and mitogen-activated protein kinase pathways", Proc Natl Acad Sci U S A 98, 2001, 247-52 (6 pgs.)
Yaari, R., et al., "Alzheimer's disease clinical trials: past failures and future opportunities", Clin. Invest. (Lond.) 2015 5 (3), 297-309 (13 pgs.)
Yuan, A., et al., "Neurofilament Proteins as Biomarkers to Monitor Neurological Diseases and the Efficacy of Therapies", Front Neurosci 15, 689938, 2021, 28 pgs.
Yuan, J., et al., "Severity Distribution of Alzheimer's Disease Dementia and Mild Cognitive Impairment in the Framingham Heart Study",. J Alzheimers Dis79, 2021, 807-817 (11 pgs.)

(56) References Cited

OTHER PUBLICATIONS

Moebius, et al., "The Case for a Novel Therapeutic Approach to Dementia: Small Molecule Hepatocyte Growth Factor (HGF/MET) Positive Modulators", Journal of Alzheimer's Disease 92, (2023), pp. 1-12 (12 pgs).

Sun, et al., "AngIV-Analog Dihexa Rescues Cognitive Impairment and Recovers Memory in the APP/PS1 Mouse via the PI3K/AKT Signaling Pathway", Brain Sci. 2021, 11, 1487, 13 pgs.

Annonymous, "ATH-1017 Treatment in Subjects with Parkinson's Disease Dementia or Dementia with Lewy Bodies (SHAPE Trial)" ClinicalTrials.gov, Id: NCT04831281, dated Jul. 24, 2023, 11 pages.

Athira Pharma Press Release, "Athira Pharma Provides 2023 Pipeline Outlook," Jan. 5, 2023, 2 pages.

Athira Pharma Press Release, "Athira Pharma Announces Encouraging Results from SHAPE Phase 2 Clinical Trial of Fosgonimeton for the Treatment of Parkinson's Disease Dementia and Dementia with Lewy Bodies", Dec. 12, 2023, 2 pages.

Akimoto, M., et al., "Hepatocyte growth factor as an enhancer of NMDA currents andsynaptic plasticity in the hippocampus", Neuroscience 128, 2004, 155-162 (8 pgs).

Akita, H., et al., "Hepatocyte growth factor improves synaptic localization of the NMDA receptor and intracellular signaling after excitotoxic injury in culturedhippocampal neurons", Expimental Neurology 210, 2008, 83-94 (12 pgs).

Alberts B., et al., "General Principles of Cell Communication", Molecular Biology of the Cell, 4th edition, New York: GarlandScience, 2002. (19 pgs). Available from:https://www.ncbi.nlm.nih.gov/books/NBK26813/. Accessed Mar. 23, 2023.

Ally, B.A., et al., "The P300 component in patients with Alzheimer's disease and their biological children", Biological Psychology 72, 2006 180-7 (8 pgs).

Annonymous, "2022 Alzheimer's disease facts and figures", Alzheimers and Dementia 2022, 18, 700-789 (90 pgs).

Annonymous, "Athira Pharma Highlights Therapeutic Potential of Fosgonimeton in Presentation of Additional Biomarker Data in Mild-to-Moderate Alzheimer's Disease Patients from ACT-AD Phase 2 Study atCTAD Conference", Nov. 29, 2022, 2 pages.

Annonymous, "Form S-1 Registration Statement of Athira Pharma, Inc.," filed with United States Securities and Exchange Commission Sep. 14, 2020, 285 pages.

Annonymous, "WHO Drug Information", vol. 35, No. 2, 2021, 4 pages.

Armada-Moreira, A., et al., "Going the Extra (Synaptic) Mile: Excitotoxicity as the Road Toward Neurodegenerative Diseases", Frontiers in Cellular Neuroscience 14, 90, 2020, (27 pgs.).

Arneson, D., et al., "Shared mechanisms among neurodegenerative diseases: from genetic factors to gene networks", Journals of Genetics 97, 2018, 795-806 (12 pgs.).

Asomugha, C.O., et al., "ACh receptors link two signaling pathways to neuroprotection against glutamate-induced excitotoxicity in isolated RGCs", J Neurochem112, 2010, 214-26 (25 pgs.).

Baiardi, S., et al., "Diagnostic value of plasma p-tau181, NfL, and GFAP in a clinical setting cohort of prevalent neurodegenerative dementias", Alzheimer's Research & Therapy 14, 153, 2022 (12 pgs).

Batista, C.R.A., et al., "Lipopolysaccharide-Induced Neuroinflammation as a Bridge to Understand Neurodegeneration", Int. J. Mol. Sci 20, 2293, 2019, (31 pgs).

Chen, Y., et al., "A non-transgenic mouse model (ICV-STZ mouse) of Alzheimer's disease: similarities to and differences from the transgenic model (3xTg-ADmouse)", Mol Neurobiol 47, 2013, 711-25 (15 pgs).

Chitnis, T. et al., "CNS inflammation and neurodegeneration", J Clin Invest 127, 2017, 3577-3587 (11 pgs).

Cummings, J., et al., "Advances in designs for Alzheimer's disease clinical trials", Am J Neurodegener Dis 2012, 1 (3):205-216, 12 pgs.

Das, J.R., et al., "Additive protective effects of donepezil and nicotine againsts alsolinol-induced cytotoxicity in SH-SY5Y cells", Neurotox Res 16, 2009, 194-204 (11 pgs.).

De Strooper, B., et al., "The Cellular Phase of Alzheimer's Disease", Cell 164, 2016, 603-15 (13 pgs.).

Desole, C., et al., "HGF and MET: From Brain Development to Neurological Disorders", Front Cell Dev Biol 9, 683609, 2021 (21 pgs.).

Eagleson, K.L, et al., "Distinct intracellular signaling mediates c-MET regulation of dendritic growth and synaptogenesis", Developmental Neurobiology 76, 2016, 1160-81 (22 pgs.)

Faes, S., et al., "PI3K and AKT: Unfaithful Partners in Cancer", Int J Mol Sci 16, 2015, 21138-21152 (15 pgs.)

Funakoshi, H., et al. "Hepatocyte Growth Factor (HGF): Neurotrophicfunctions and therapeutic implications for neuronal injury/diseases", Current Signal Transduction Therapy, 6, 2011, 156-167 (12 pgs).

Funakoshi, H., et al., "Hepatocyte growth factor: from diagnosis toclinical applications", Clin Chim Acta 327, 2003, 1-23 (23 pgs.)

Gao, B.L., et al., "Neuroprotective effects of donepezil against AB25-35-inducedneurotoxicity", Eur J Med Res 27, 219, 2022, (8pgs.)

Götze, K., et al., "Plasma neurofilament light chain in memory clinic practice:Evidence from a real-life study", Neurobiol Dis. 176, 105937, 2023, 7 pages.

He, F., et al., "HGF protects cultured cortical neurons against hypoxia/reoxygenationinduced cell injury via ERK1/2 and PI-3K/Akt pathways", Colloids Surf B Biointerfaces 61, 2008, 290-297 (8 pgs.)

Hewett, S.J., et al., "Interleukin-1ß in Central Nervous System Injury and Repair", Eur J Neurodegener Dis 1, 2012, 195-211 (21 pgs.)

Higgins, J. "Prodrugs in Drug Discovery", ACS Webinars, Nov. 19, 2015, 27 pgs.

Hua, X., et al., "Safety, Tolerability, Pharmacokinetics, and Pharmacodynamics of the Positive Modulator of HGF/MET, Fosgonimeton, in Healthy Volunteers and Subjects with Alzheimer's Disease: Randomized, Placebo-Controlled, Double-Blind, Phase 1 Clinical Trial", J Alzheimers Dis 86, 2022, 1399-1413 (15 pgs.)

Hwang, J., et al., "Microglia signaling as a target of donepezil", Neuropharmacology 58, 2010, 1122-1129 (8 pgs.)

Hynd, M.R., et al., "Glutamate-mediated excitotoxicity and neurodegeneration in Alzheimer's disease", Neurochem Int 45, 2004, 583-595 (13 pgs.)

Ishihara, N., et al., "Inhibition of apoptosis-inducing factor translocation is involved in protective effects of hepatocyte growth factor against excitotoxic cell death incultured hippocampal neurons", Journal of Neurochemistry 95, 2005, 1277-1286 (10 pgs.)

Ito, K., et al., "Artificial human Met agonists based on macrocycle scaffolds", Nat Commun 11, 2015, 63-73 (11 pgs.)

Jack Jr., C.R., et al., "A/T/N: An unbiased descriptive classification scheme for Alzheimer disease biomarkers", Neurology 87, 2016, 539-547 (9 pgs).

Jack Jr., C.R., et al., "NIA-AA Research Framework: Toward a biological definition ofAlzheimer's disease", Alzheimer's & Dementia 14, 2018, 535-562 (28 pgs).

Jayaraman, A., et al., "TNF-mediated neuroinflammation is linked to neuronal necroptosis in Alzheimer's disease hippocampus", Acta Neuropathol Commun9, 159, 2021, 21 pgs.

Jeong, J., "EEG dynamics in patients with Alzheimer's disease", Clin Neurophysiol 115, 2004, 1490-1505 (16 pgs).

Jia, Y., et al., "HGF Mediates Clinical-Grade Human Umbilical Cord-Derived Mesenchymal Stem Cells Improved Functional Recovery in a Senescence-Accelerated Mouse Model of Alzheimer's Disease", Adv Sci 7, 1903809, 2020, 17 pgs.

Johnston, J.L., et al., "Fosgonimeton, a Novel Positive Modulator of the HGF/MET System, Promotes Neurotrophic and Procognitive Effects in Models of Dementia", Neurotherapeutics, 2022, 21 pgs. Available from:https://pubmed.ncbi.nlm.nih.gov/36538176/. Accessed Mar. 23, 2023.

Kennedy, R., et al., "Association of Concomitant Use of Cholinesterase Inhibitors or Memantine With Cognitive Decline in Alzheimer Clinical Trials A Meta-analysis", JAMA Network Open, 2018, 10 pages. Downloaded From: https://jamanetwork.com/ on May 23, 2023.

(56) References Cited

OTHER PUBLICATIONS

Knopman, D.S., et al., "Alzheimer disease", Nat Rev Dis Primers 7, 33, 2021, 47 pgs.
Koffie, R.M., et al., "Alzheimer's disease: synapses gone cold", Molecular Neurodegeneration 6, 63, 2011, 9 pgs.
Koike, H., et al., "Prevention of onset of Parkinson's disease by in vivo gene transfer of human hepatocyte growth factor in rodent model: a model of gene therapy for Parkinson's disease", Gene Ther 13, 2006, 1639-1644 (6 pgs).
Kraska, A., et al., "In Vivo Cross-sectional Characterization of Cerebral Alterations Induced by Intracerebroventricular Administration of Streptozotocin", PLOS ONE 7, e46196, 2012, 9 pgs.
Kulczynska-Przybik, A., et al. "Cerebrospinal Fluid and Blood CX3CL1 as a Potential Biomarker in Early Diagnosis and Prognosis of Dementia", Curr Alzheimer Res 17, 2020, 709-721 (13 pgs.)
Leblanc, C. A., "The Role of Apoptotic Pathways in Alzheimer's Disease Neurodegeneration and Cell Death", Current Alzheimer Research 2, 2005, 389-402 (14 pgs.)
Lewczuk, P., et al., "Plasma neurofilament light as a potential biomarker of neurodegeneration in Alzheimer's disease", Alzheimers Res Ther 10, 71, 2018, 10 pgs.
Liu, J., et al., "The Role of NMDA Receptors in Alzheimer's Disease", Front Neurosci 8, 43, 2019, 22 pgs.
Liu, X.S., et al., "Human umbilical cord mesenchymal stem cells infected with adenovirus expressing HGF promote regeneration of damaged neuron cells in a Parkinson's disease model", Biomed Research International, 2014, Article ID: 909657, 7 pages.
Lloret, A., et al., "Amyloid-β toxicity and tau hyperphosphorylation are linked via RCAN1 in Alzheimer's disease", Journal of Alzheimer's disease, JAD 27, 2011, 701-9 (9 pgs.).
Ghosh et al., "Organic Carbamates in Drug Design and Medicinal Chemistry," J. Med. Chem., 2015, 58:2895-2940.
Athira Pharma Inc., United States Securities and Exchange Commission, Form 8-K, Oct. 18, 2021, 7 pages.
Athira Pharma Press Release, Retrieved from the internet: https://www.athira.com/athira-pharma-announces-leadership-changes//, "Athira Pharma Announces Leadership Changes," Oct. 21, 2021, 2 pages.
"ATH-1017 Treatment in Subjects with Parkinson's Disease Dementia or Dementia with Lewy Bodies (SHAPE Trial)" ClinicalTrials.gov, Id: NCT04831281, dated Jul. 24, 2023, 11 pages.
"ATH-1017 Treatment in Subjects with Parkinson's Disease Dementia" ClinicalTrials.gov, ID: NCT04831281, dated Apr. 5, 2021, 7 pages.
Aduhelm™, New Drug Approval, Jun. 7, 2021, 4 pages.
Aduhelm™, Prescribing Information, 2021, 22 pages.
ATH-1017=NDX-1017=Fosgonimenton_June 30, 2021; Screenshot, Google search page results, Snagit generated by examiner, date limited, (Year: 2024) 1 page.
Athira Pharma Inc., United States Securities and Exchange Commission, Draft Form S-1, confidentially submitted Jul. 24, 2020, 229 pages.
Athira Pharma Inc., United States Securities and Exchange Commission, Form 8-K, Jun. 21, 2022, 26 pages.
Athira Pharma Inc., United States Securities and Exchange Commission, Form S-1, Aug. 26, 2020, 351 pages.
Athira Pharma Press Release, "Athira Pharma Presents Data from ACT-AD Phase 2 Proof-of-Concept Clinical Study of Fosgonimeton in Mild-to-Moderate Alzheimer's Patients at the Alzheimer's Patients at the Alzheimer's Association International Conference 2022," Aug. 3, 2022, 3 pages.
Athira Pharma, "LIFT-AD Topline Readout", Sep. 3, 2024 (15 pages).
Campbell, Jay, "Dihexa Peptide: Benefits", Dosage and Side Effects. https://jaycampbell.com/peptides/ dihexa-the-cognitive-repairment-peptide, 2020, 24 pages.
Cummings et al., "Alzheimer's Disease Drug Development Pipeline: 2018," Alzheimer's & Dementia: Transl Res & Clin Internventions, 2018, 4:195-214.
Cummings, et al., "Treatment Combinations for Alzheimer's Disease: Current and Future Pharmacotherapy Options", Journal of Alzheimer's Disease 67 (2019) 779-794 (16 pages).
Guo, et al., "Memantine, Donepezil, or Combination Therapy-What is the best therapy for Alzheimer's Disease? A Network Meta-Analysis", Brain and Behavior, 2020, (13 pgs).
Hua et al., "Safety, Tolerability, Pharmacokinetics, and Pharmacodynamics of the Positive Modulator of HGF/MET, Fosgonimeton, in Healthy Volunteers and Subjects with Alzheimer's Disease: Randomized, Placebo-Controlled, Double-Blind, Phase I Clinical Trial," J Alzheimer's Disease, 2022, 86:1399-1413.
International Search Report and Written Opinion received in PCT/US2021/042071, dated Oct. 26, 2021, Applicant: Athira Pharma, Inc.; Examiner: Kari Rodriguez, 9 pages.
International Search Report and Written Opinion received in PCT/US2021/042974, dated Dec. 30, 2021, Applicant: Athira Pharma, Inc.; Examiner: Kari Rodriguez; 16 pages.
International Search Report and Written Opinion received in PCT/US2022/034386, dated Oct. 5, 2022, Applicant: Athira Pharma, Inc.; Examiner: Kari Rodriguez, 9 pages.
International Search Report and Written Opinion received in PCT/US2022/074021, dated Oct. 4, 2022, Applicant: Athira Pharma, Inc.; Examiner: Shane Thomas; 11 pages.
Irwin et al., "Neuropathological and genetic correlates of survival and dementia onset in synucleinopathies: a retrospective analysis," Lancet Neurol, 2017, 16:55-65.
Kokras et al., "Acetyl Cholinesterase Inhibitors and Cell-Derived Peripheral Inflammatory Cytokines in Early Stages of Alzheimer's Disease," J Clin Psychopharmacology, 2018, 38(2): 1-6.
Kulisevsky et al., "Cognitive Impairment in Parkinson's Disease: Tools for Diagnosis and Assessment," Movement Disorders, 2009, 24(8): 1103-1110.
Leuzy et al., "Blood-based biomarkers for Alzheimer's disease," EMBO Mol Med, 2022, 14:e14408, 15 pages.
Miller et al., "Gender Differences in Parkinson's Disease: Clinical Characteristics and Cognition," Movement Disorders, 2010, 25(16): 2695-2703.
Moebius et al., Fosgonimeton Provides Congruent Improvements on Neurodegeneration Biomarkers, Significantly Correlating with Composite Clinical Scores of Cognition and Function in Alzheimer's Disease, Apr. 22-27, 2023, Boston, MA, Presentation at the 75th AAN Annual Meeting, 16 pages.
Moebius et al., "HGF/MET Receptor Agonist NDX-1017 Translational Phase 1a and b Results," Athira Pharma Presentation, Dec. 2019, 24 pages.
Moebius et al., "ACT-AD: Fosgonimeton in Mild-to-Moderate Alzhemier's Disease—First Results of a Randomized, Placebo-Controlled, 26-Week, Phase 2 Proof-of-Concept Trial," Presentation at AAIC 2022, 13 pages.
PubChem ID No. CID-156596375, Fosgonimeton, dated Sep. 16, 2021, 12 pages.
Sarikaya et al., "Evaluation of Cognitive Functions in Parkinson's Patients without Dementia with Auditory Event Related Potential (P300)," J Psychiatry Neurological Sci, 2014, 27:132-137.
U.S. Appl. No. 18/905,361, filed Oct. 3, 2024, available at Patent Center.

* cited by examiner

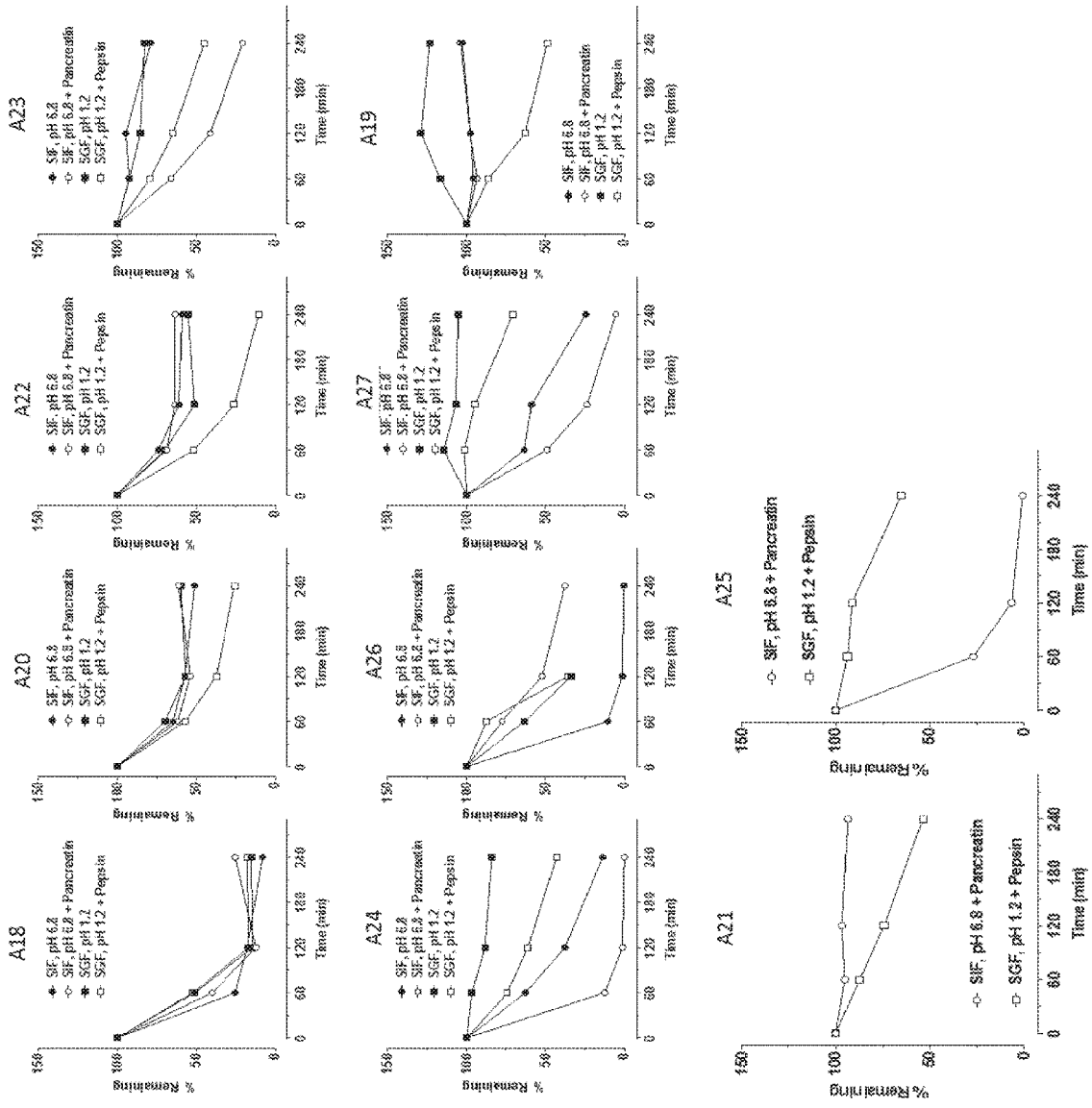
FIG 1. Stability of pro-drugs in Simulated Intestinal or Gastric Fluids

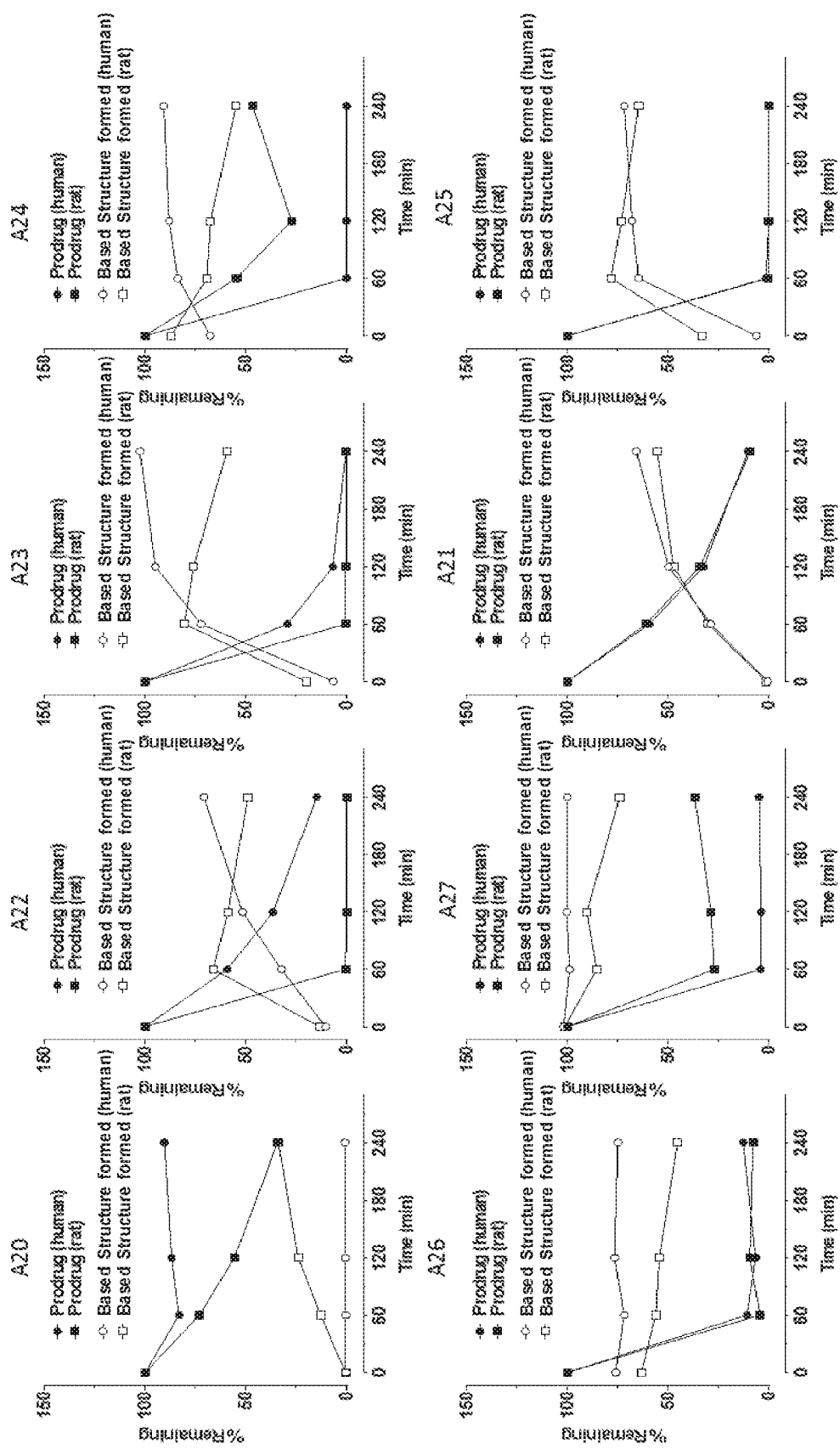
FIG 2. Formation of active pro-drugs

METHODS OF TREATING NEURODEGENERATIVE DISEASE WITH SUBSTITUTED N-HEXANOIC-L-TYROSINE-L-ISOLEUCINE-(6)-AMINOHEXANOIC AMIDE ANALOGUES

1. CROSS REFERENCE TO RELATED APPLICATIONS

This application is a divisional of U.S. application Ser. No. 16/306,277, filed Nov. 30, 2018, which is a 35 U.S.C. § 371 national stage of International Application No. PCT/US2017/035547, filed Jun. 1, 2017, which claims the benefit of U.S. Provisional Application No. 62/344,305, filed Jun. 1, 2016, each of which is hereby incorporated in its entirety by reference for any purpose.

2. BACKGROUND

The small molecule peptidic compound, N-hexanoic-L-tyrosine-L-isoleucine-(6)-aminohexanoic amide ("Base Structure"), has been shown or predicted to have potential as a neuroprotective/neuroregenerative agent, to protect from or reverse neurodegenerative disease, to prevent or reverse the symptoms of dementia, to facilitate repair of traumatic injury to the nervous system, and to enhance cognitive function. Given Base Structure's therapeutic potential to treat Alzheimer's disease, Parkinson's disease, amyotrophic lateral sclerosis, other dementias and neurodegenerative diseases, spinal cord injury, traumatic brain injury, and sensorineural hearing and vision loss, there is a need in the art for compounds that retain Base Structure's therapeutic activities while possessing optimized pharmacokinetic and pharmacodynamic properties.

3. SUMMARY

Compounds have been synthesized that demonstrate increased stability in simulated intestinal fluid and simulated gastric fluid, but that can be hydrolyzed in plasma to produce Base Structure or Base Structure-like compounds that retain Base Structure's beneficial properties.

Accordingly, in a first aspect, compounds are provided.

In typical embodiments, the compounds possess a di-amino acid core structure and are substituted by one or more organic functional groups at the C-terminus, N-terminus, and/or the side-chain of the core.

In some embodiments, the compound is a compound of formula I:

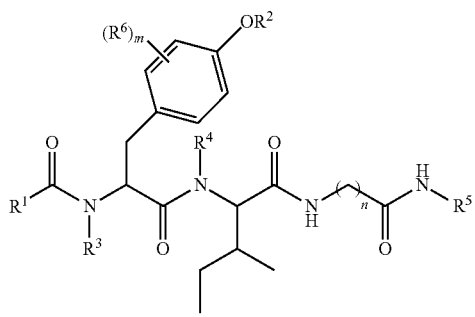

(I)

wherein:
n is 1, 2, 3, 4, 5, 6, 7, 8, or 9;
m is 0, 1, 2, 3, or 4;
$R^1$ is selected from the group consisting of: amino, substituted amino, alkoxy, substituted alkoxy, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_1$-$C_6$ alkyl aryl, $C_1$-$C_6$ substituted alkyl aryl, $C_1$-$C_6$ alkenyl aryl, $C_1$-$C_6$ substituted alkenyl aryl, $C_1$-$C_6$ alkynyl aryl, $C_1$-$C_6$ substituted alkynyl aryl, norleucine, tyrosine, phenylalanine, aspartic acid, arginine, isoleucine, serine, threonine, histidine, glycine, cysteine, methionine, tryptophan, lysine norvaline, norleucine, ornithine, S-benzyl cysteine, O-benzyl serine, O-benzyl threonine, cyclohexylalanine, 4-tetrahydropyranyl-glycine, and azaleucine;
$R^2$ is selected from the group consisting of: hydrogen, —CH($R^a$)OPO(OH)$_2$, —CO—Y,

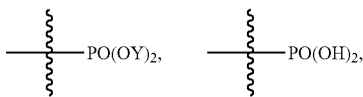

—C(=O)—Y, —CO—U, —C(=O)—(CH$_2$)$_r$U, and —CH$_2$—V, where $R^a$ is hydrogen or CH$_3$, where Y is —Z—(CH$_2$)$_q$—W—$R^b$, q is 0-4, where Z and W are independently selected from the group consisting of: CH$_2$, O, S, NR$^c$ and R$^b$, where $R^c$ is selected from the group consisting of: hydrogen, $C_1$-$C_4$ alkyl, and $C_3$-$C_6$ cycloalkyl, $R^b$ is selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_3$-$C_8$ cycloalkyl, $C_3$-$C_8$ substituted cycloalkyl, $C_6$-$C_{10}$ aryl, $C_6$-$C_{10}$ substituted aryl, $C_3$-$C_8$ heterocycloalkyl, $C_3$-$C_8$ substituted heterocycloalkyl, $C_4$-$C_{10}$ heteroaryl, and $C_4$-$C_{10}$ substituted heteroaryl, where r is 0-5, U is selected from aryl, heteroaryl or heterocycloalkyl, where V is —O—C(=O)-Q-(CH$_2$)$_r$—$R^d$, where Q is selected from the group consisting of: a bond, O, and N($R^c$), where $R^d$ is selected from the group consisting of: $C_6$-$C_{10}$ aryl, $C_4$-$C_{10}$ heteroaryl, $C_3$-$C_8$ heterocycloalkyl, a hexose, a pentose, and -(5-methyl-2-oxo-1,3-dioxol-4-yl)methyl), or alternatively —C(=O)—Y forms an amide bond thru a nitrogen atom on Y in which case Y is a selected from the group consisting of: glycine, sarcosine, N,N-diemthyl glycine, alanine, valine, leucine, isoleucine, lysine, ornithine, arigine, serine, and theronine;
$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_3$-$C_8$ cycloalkyl, $C_3$-$C_8$ substituted cycloalkyl, $C_6$-$C_{10}$ aryl, $C_6$-$C_{10}$ substituted aryl, $C_3$-$C_8$ heterocycloalkyl, $C_3$-$C_8$ substituted heterocycloalkyl, $C_4$-$C_{10}$ heteroaryl, $C_4$-$C_{10}$ substituted heteroaryl,

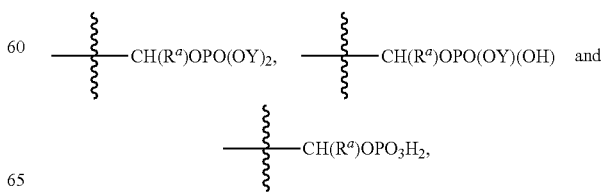

or optionally $R^3$ and $R^4$ together are bonded to form a fused bicyclic ring system or a spirocyclic ring system;

$R^5$ is selected from the group consisting of: hydrogen,

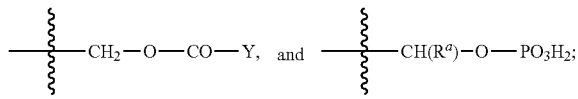

each $R^6$ is independently selected from the group consisting of: hydrogen, deuterium, $CH_3$, F, $^{19}F$, and $^{18}F$;

wherein optionally Z and W are taken together to form a $C_3$-$C_8$ heterocycloalkyl or $C_4$-$C_{10}$ heteroaryl or fused bicyclic ring system in which one of the rings is a $C_4$-$C_{10}$ heteroaryl;

and wherein the amino acid of $R^1$, if present, is covalently bonded either thru the nitrogen atom of the N-terminus of the amino acid to the carbon atom of the C(=O) in

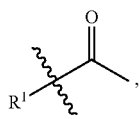

or a carbon atom of the amino acid of $R^1$ is bonded to the C(=O) such that

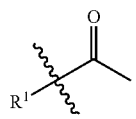

taken together represents amino acid where the C(=O) of

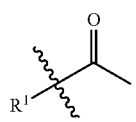

is the carboxy-terminus of the amino acid;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when both $R^2$ and $R^5$ are hydrogen and n is 5, at least one of the $R^3$ or $R^4$ groups is not hydrogen;

or a tautomer and/or a pharmaceutically acceptable salt thereof.

In various embodiments, the compound is selected from among certain specific compounds disclosed herein.

In another aspect, compositions comprising at least one of the compounds described herein are provided.

In a further aspect, pharmaceutical compositions comprising at least one of the compounds described herein are provided.

In a still further aspect, methods of treatment are provided.

The methods comprise administering at least one compound as described herein to a subject in an amount effective to treat, protect from, or reverse neurodegenerative disease, to prevent or reverse the symptoms of dementia, to facilitate repair of traumatic injury to the nervous system, or to enhance cognitive function. In various embodiments, the subject has a disease selected from Alzheimer's disease, Parkinson's disease, amyotrophic lateral sclerosis, other dementias and neurodegenerative diseases, spinal cord injury, traumatic brain injury, and/or sensorineural hearing loss. In typical embodiments, the method comprises administering a pharmaceutical composition comprising at least one of the compounds described herein, as described herein.

In various embodiments, the compound is administered as the sole medical treatment. In various embodiments, the compound is administered in combination with other medical and/or surgical interventions according to the prevailing standards of care.

These and other embodiments are described in further detail herein.

4. BRIEF DESCRIPTION OF THE DRAWINGS

These and other features, aspects, and advantages of the present invention will become better understood with regard to the following description, and accompanying drawings, where:

FIG. 1 are graphs containing data from experiments testing stability of various compounds synthesized as potential prodrugs of Base Structure in the presence of Simulated Intestinal Fluid (SIP), pH 6.8 (+/−Pancreatin) or Simulated Gastric Fluid (SGF), pH 1.2 (+/−Pepsin). The results demonstrate increased stability of some prodrugs even in the presence of enzymes native to either intestinal or gastric fluids over 240 minutes.

FIG. 2 are graphs showing data measuring the formation of Base Structure from various prodrugs in both human and rat plasma over 240 minutes, measured both as percent prodrug compound remaining (left y-axis).

5. DETAILED DESCRIPTION

5.1. Definitions

Various terms used in the specification and claims herein are defined as set forth below, unless otherwise specifically defined in this disclosure. All technical and scientific terms not defined herein have the meaning commonly understood by a person skilled in the art to which this invention belongs.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkenyl" refers to straight or branched hydrocarbyl groups having from 1 to 6 carbon atoms and preferably 2 to 4 carbon atoms and having at least 1 and preferably from 1 to 2 sites of unsaturation (>C=C<). Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

In some embodiments, the substituted alkyl groups include halogenated alkyl groups and particularly halogenated methyl groups such as trifluoromethyl, difluromethyl, fluoromethyl and the like.

"Alkyl aryl" refers to an alkyl group having from 1 to 8, preferably 1 to 5, or more preferably 1 to 3 carbon atoms in length and is substituted specifically at any one of the carbons along the chain with an aryl group. "Alkenyl aryl" refers to an alkenyl or alkene group having from 1 to 8, preferably 1 to 5, or more preferably 1 to 3 carbon atoms in length and is substituted specifically at any one of the carbons along the chain with an aryl group. The aryl group can include heteroatoms or not. Alkynyl aryl" refers to an alkynyl or alkyne group having from 1 to 8, preferably 1 to 5, or more preferably 1 to 3 carbon atoms in length and is substituted specifically at any one of the carbons along the chain with an aryl group. The aryl group can include heteroatoms or not.

"Cycloalkyl" or "Cyclyl alkyl" refers to a saturated or partially saturated, but not aromatic, group having from 3 to 10 ring carbon atoms and no heteroatoms. Cycloalkyl encompasses single ring systems.

"Substituted alkenyl" refers to alkenyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Ar" and/or "aryl" refers to any group which is aromatic. This group must be cyclic; and does not contain heteroatoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NR$^{30}$C(O)alkyl, —NR$^{30}$C(O)substituted alkyl, —NR$^{30}$C(O)cycloalkyl, —NR$^{30}$C(O)substituted cycloalkyl, —NR$^{30}$C(O)alkenyl, —NR$^{30}$C(O)substituted alkenyl, alkoxy, substituted alkoxy-NR$^{30}$C(O)alkynyl, —NR$^{30}$C(O)substituted alkynyl, —NR$^{30}$C(O)aryl, —NR$^{30}$C(O)substituted aryl, —NR$^{30}$C(O)heteroaryl, —NR$^{30}$C(O)substituted heteroaryl, —NR$^{30}$C(O)heterocyclic, and —NR$^{30}$C(O)substituted heterocyclic wherein R$^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the groups H—C(N)—, alkyl-C(N)—, substituted alkyl-C(N)—, alkenyl-C(N)—, substituted alkenyl-C(N)—, alkynyl-C(N)—, substituted alkynyl-C(N)—, cycloalkyl-C(N)—, substituted cycloalkyl-C(N)—, aryl-C(N)—, substituted aryl-C(N)—, heteroaryl-C(N)—, substituted heteroaryl-C(N)—, heterocyclic-C(N)—, and substituted heterocyclic-C(N)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —$C(O)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl carbonyloxy" refers to the group —$C(NR^{33})OR^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —$C(S)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}C(O)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —$NR^{30}C(S)NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—$C(O)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, a monosaccharide (which may be covalently bonded to the aryl group thru any oxygen atom on the saccharide), and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Ethylene glycol" refers to the group —O—CH2CH2-O-E, wherein E is either H or CH3.

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 4 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 2 to 10 ring carbon atoms and from 1 to 4 ring heteroatoms selected from the group consisting of nitrogen, sulfur, or oxygen. $C_x$ cycloalkyl or heterocycloalkyl refers to a group having x number of ring carbon atoms excluding the ring heteroatoms. Heterocycle encompasses single ring or multiple condensed rings, including fused, bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, dexahydroindole, dihydropyridine, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, imidazolinone, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Phthalimido" refers to the group

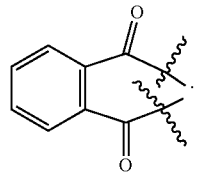 [SMILES: *C(=O)c1ccccc1C(*)=O]

Phthalimide functional groups are well known in the art and can be generated by covalently bonding a nitrogen atom to a $C_6H_4(CO)_2$ group.

"Polyethylene glycol" refers to the group —O—$(CH_2CH_2$—O$)_n$-E, wherein E is either H or $CH_3$, where n is between 2-20,000.

"Spirocyclic ring system" refers to a ring system with two rings that has a single ring carbon atom in common to both rings. Herein used the term bicyclic can incorporate up to four heteroatoms in either ring.

"Bicyclic ring" or "Bicyclic ring system" refers to a ring system with two rings that has two ring carbon atoms in common, and which can located at any position along either ring. Herein used the term bicyclic ring system can incorporate up to four heteroatoms in either ring.

"Sulfinyl" refers to the divalent group —SO—.

"Sulfonyl" refers to the divalent group —S(O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substitution" or "substitution" or "substitutied" generally refers groups which are covalently bonded to an atom to replace a hydrogen atom. The atom in this general context can be a carbon atom or a heteroatom, for example a nitrogen atom.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Tautomer" refers to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

The term "ameliorating" refers to any therapeutically beneficial result in the treatment of a disease state, e.g., an inflammatory disease state, including lessening in the severity or progression, remission, or cure thereof. In some embodiments, "ameliorating" includes prophylaxis of a disease state.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can, in some embodiments, be a "prophylactically effective amount" as prophylaxis can be considered therapy.

"Subject" refers to a mammalian organism treated using a compound of the present invention. The "subject" can be a human or non-human mammalian organism.

"Treating" or "treatment" of a disease or disorder in a subject refers to 1) preventing the disease or disorder from occurring in a subject that is predisposed or does not yet display symptoms of the disease or disorder; 2) binding the disease or disorder or arresting its development; or 3) ameliorating or alleviating the cause of the regression of the disease or disorder.

As used herein, an agent is said to be "specific" if it reacts or associates more frequently, more rapidly, with greater duration and/or with greater affinity with a specified target than it does with alternative substances, especially as compared to substances that are structurally related to the target, e.g., an isoform of the target. In some embodiments, an agent is "specific" for a target if a concentration of the agent that produces a maximal effect in an in vitro or in vivo target assay (e.g., a binding assay or an enzyme activity assay) produces no measurable effect in a comparable assay carried out using another substance, especially one or more substances that are structurally related to the target.

As used herein, the term "contacting," as used herein, includes both directly contacting cells, for example, in vivo, in vitro, or ex vivo, or indirectly contacting cells, such as, for example, by administering an agent to a subject. Further, "contacting" a cell with an agent includes administering or applying a prodrug version of the agent.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

5.2. Additional Interpretational Conventions

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium, $^{14}C$, $^{32}P$ and $^{35}S$ are thus within the scope of the present technology. Procedures for inserting such labels into the compounds of the present technology will be readily apparent to those skilled in the art based on the disclosure herein.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures, and d or l enriched stereomeric mixtures, as well as the individual optical isomers can be isolated or synthesized so as to be substantially free of their enantiomeric or diastereomeric partners, and these stereoisomers are all within the scope of the present technology.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

Herein any substituted functional group is substituted at from one to three different positions, and those one to three substituting groups are capable of each independently being substituted at one to three positions, wherein any and each substituting group is independently selected from the group consisting of: halogen, hydroxyl, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, acyl, acylamino, aminocarbonylamino, aminoacyl, acyloxy, amino, substituted amino, aminocarbonyl, aminothiocarbonyl, aminoacyl carbonyloxy, aminocarbonylamino, aminothiocarbonylamino, aminocarbonyloxy, aminosulfonyl, aminosulfonyloxy, aminosulfonylamino, amidino, $C_1$-$C_8$ alkoxy, substituted $C_1$-$C_8$ alkoxy, $C_3$-$C_7$ aryl, substituted $C_3$-$C_7$ aryl, $C_3$-$C_7$ aryloxy, substituted $C_3$-$C_7$ aryloxy, $C_3$-$C_7$ arylthio, substituted $C_3$-$C_7$ arylthio, carboxyl, carboxyl ester, (carboxyl ester)amino, (carboxyl ester)oxy, $C_3$-$C_{10}$ cycloalkyl, substituted $C_3$-$C_{10}$ cycloalkyl, $C_3$-$C_7$ heterocycloalkyl, guanidino, substituted guanidino, $C_3$-$C_7$ heteroaryloxy, $C_3$-$C_7$ substituted heteroaryloxy, $C_3$-$C_7$ heteroarylthio, $C_3$-$C_7$ substituted heteroarylthio, sulfonyl, substituted sulfonyl, sulfinyl, substituted sulfinyl, sulfonyloxy, substituted sulfonyloxy, thioacyl, alkylthio, substituted alkylthio, $C_3$-$C_7$ heteroaryl, and substituted $C_3$-$C_7$ heteroaryl.

Herein any and all heteroaryl and heterocycloalkyl substituents may contain up to four heteroatoms selected from the group consisting of: O, N, and S but may not contain a heteroatom-heteroatom bond such as: O—O, O—S, N—S, N—O and S—S bonds are not covered. It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the definitions presented herein are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

5.3. Compounds

In a first aspect, compounds are provided that demonstrate improved drug characteristics and enhanced solubility properties, improved DMPK properties demonstrated by increased stability in simulated intestinal fluid and simulated gastric fluid, but that can be hydrolyzed in plasma to produce Base Structure, or to produce Base Structure-like compounds that retain Base Structure's therapeutic activity, are provided.

In typical embodiments, the compounds possess a diamino acid core structure and are substituted by one or more organic functional groups at the C-terminus, N-terminus, and/or the side-chain of the core.

In some embodiments, the compound is a compound of formula II:

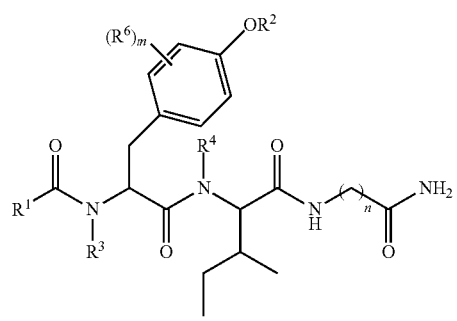

(II)

wherein:
n is 1, 2, 3, 4, 5, 6, 7, 8, or 9;
m is 0, 1, 2, 3, or 4;
$R^1$ is selected from the group consisting of: $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl;
$R^2$ is selected from the group consisting of: hydrogen,

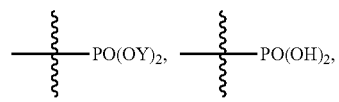

—C(=O)—Y and —CO—U, where Y is —Z—$(CH_2)_q$—W—$R^b$, q is 0-4, where Z and W are independently selected from the group consisting of: $CH_2$, O, S, $NR^c$ and $R^b$, where $R^c$ is selected from the group consisting of: hydrogen, $C_1$-$C_4$ alkyl, and $C_3$-$C_6$ cycloalkyl, $R^b$ is selected from the group consisting of: hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl, or alternatively —C(=O)—Y forms an amide bond thru a nitrogen atom on Y in which case Y is a selected from the group consisting of: glycine, sarcosine, N,N-diemthyl glycine, alanine, valine, leucine, isoleucine, lysine, ornithine, arigine, serine, and theronine and where U is selected from the group consisting of: pyridine, 1,4-dihydropyridine, N-alkyl-1,4-dihydropyridine, and C-imidazole or U is selected from aryl, heteroaryl or heterocycloalkyl;

$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl, or optionally $R^3$ and $R^4$ together are bonded to form a fused bicyclic ring system or a spirocyclic ring system;

each $R^6$ is independently selected from the group consisting of: hydrogen, deuterium, $CH_3$, F, $^{19}$F, and $^{18}$F;

wherein optionally Z and W are taken together to form a $C_3$-$C_8$ heterocycloalkyl or $C_4$-$C_{10}$ heteroaryl or bicyclic ring system in which one of the rings must be a $C_4$-$C_{10}$ heteroaryl;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer and/or a pharmaceutically acceptable salt thereof.

In some embodiments, the compound is a compound of formula III:

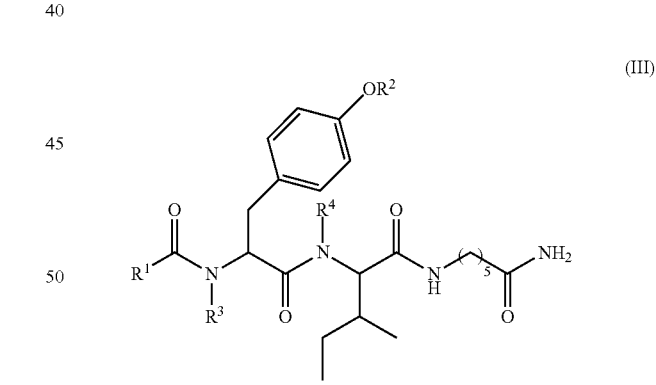

(III)

wherein:
$R^1$ is a $C_1$-$C_{12}$ alkyl or $C_1$-$C_{12}$ substituted alkyl;
$R^2$ is selected from the group consisting of: hydrogen,

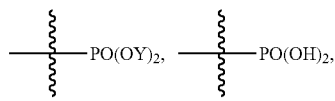

and —C(=O)—Y, where Y is —Z—$(CH_2)_q$—W—$R^b$, q is 0-4, where Z and W are independently selected from the group consisting of: $CH_2$, O, S, $NR^c$ and $R^b$, where $R^c$ is selected from the group consisting of: hydrogen, $C_1$-$C_4$ alkyl, and $C_3$-$C_6$ cycloalkyl, $R^b$ is selected from the group consisting of: hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl;

$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl, or optionally $R^3$ and $R^4$ together are bonded to form a fused bicyclic ring system or a spirocyclic ring system, where the fused ring is a $C_3$-$C_8$ heterocycloalkyl or $C_6$-$C_{10}$ aryl or $C_4$-$C_{10}$ heteroaryl;

wherein optionally Z and W are taken together to form a $C_3$-$C_8$ heterocycloalkyl or $C_4$-$C_{10}$ heteroaryl or bicyclic ring system in which one of the rings must be a $C_4$-$C_{10}$ heteroaryl;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer and/or a pharmaceutically acceptable salt thereof.

In some embodiments, the compound is a compound of formula IV:

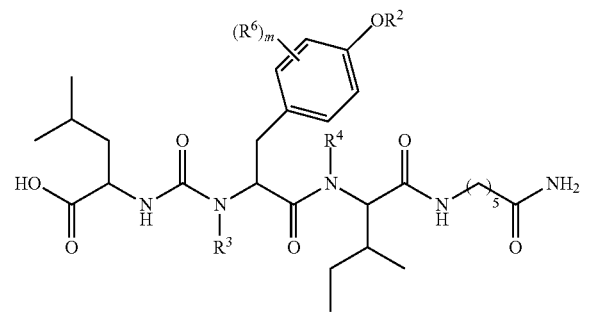

(IV)

wherein:
n is 1, 2, 3, 4, 5, 6, 7, 8, or 9;
m is 0, 1, 2, 3, or 4;
$R^2$ is selected from the group consisting of: hydrogen, —CH($R^a$)OPO(OH)$_2$, —CO—Y,

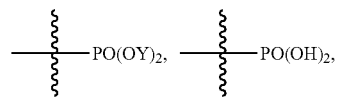

—C(=O)—Y, —CO—U, —C(=O)—(CH$_2$)$_r$U, and —CH$_2$—V, where $R^a$ is hydrogen or $CH_3$, where Y is —Z—(CH$_2$)$_q$—W—$R^b$, q is 0-4, where Z and W are independently selected from the group consisting of: $CH_2$, O, S, $NR^c$ and $R^b$, where $R^c$ is selected from the group consisting of: hydrogen, $C_1$-$C_4$ alkyl, and $C_3$-$C_6$ cycloalkyl, $R^b$ is selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, $C_1$-$C_{12}$ substituted alkynyl, $C_3$-$C_8$ cycloalkyl, $C_3$-$C_8$ substituted cycloalkyl, $C_6$-$C_{10}$ aryl, $C_6$-$C_{10}$ substituted aryl, $C_3$-$C_8$ heterocycloalkyl, $C_3$-$C_8$ substituted heterocycloalkyl, $C_4$-$C_{10}$ heteroaryl, and $C_4$-$C_{10}$ substituted heteroaryl, where r is 0-5, U is selected from aryl, heteroaryl or heterocycloalkyl, where V is —O—C(=O)-Q-(CH$_2$)$_r$—$R^d$, where Q is selected from the group consisting of: a bond, O, and N($R^c$), where $R^d$ is selected from the group consisting of: $C_6$-$C_{10}$ aryl, $C_4$-$C_{10}$ heteroaryl, $C_3$-$C_8$ heterocycloalkyl, a hexose, a pentose, and -(5-methyl-2-oxo-1,3-dioxol-4-yl)methyl), or alternatively —C(=O)—Y forms an amide bond thru a nitrogen atom on Y in which case Y is a selected from the group consisting of: glycine, sarcosine, N,N-diemthyl glycine, alanine, valine, leucine, isoleucine, lysine, ornithine, arigine, serine, and theronine;

$R^3$ and $R^4$ are independently selected from the group consisting of: hydrogen, $C_1$-$C_{12}$ alkyl, $C_1$-$C_{12}$ substituted alkyl, $C_1$-$C_{12}$ alkenyl, $C_1$-$C_{12}$ substituted alkenyl, $C_1$-$C_{12}$ alkynyl, and $C_1$-$C_{12}$ substituted alkynyl, or optionally $R^3$ and $R^4$ together are bonded to form a fused bicyclic ring system or a spirocyclic ring system;

each $R^6$ is independently selected from the group consisting of: hydrogen, deuterium, $CH_3$, F, $^{19}F$, and $^{18}F$;

wherein optionally Z and W are taken together to form a $C_3$-$C_8$ heterocycloalkyl or $C_4$-$C_{10}$ heteroaryl or bicyclic ring system in which one of the rings must be a $C_4$-$C_{10}$ heteroaryl;

and wherein any and all heterocyclic and heteroaryl rings contain up to four heteroatoms selected from the group consisting of: O, N, and S;

with the proviso that when both Z and W are heteroatoms, the value of q cannot be 1;

and with the proviso that when $R^2$ is hydrogen, at least one of the $R^3$ or $R^4$ groups is not hydrogen;

or a tautomer and/or a pharmaceutically acceptable salt thereof.

In some embodiments, the compound is a compound of formula V:

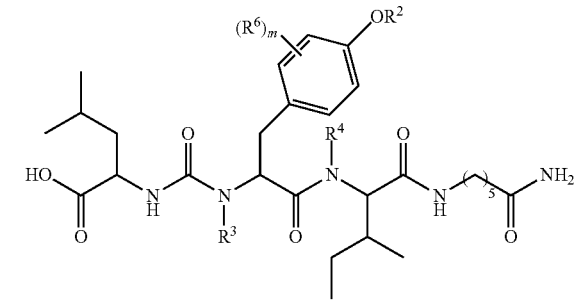

(V)

wherein:
m is 0, 1, 2, 3, or 4;
$R^2$ is selected from the group consisting of: hydrogen,

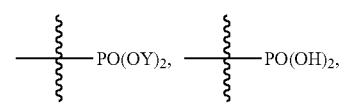

and —C(=O)—Y, where Y is —Z—(CH$_2$)$_q$—W—$R^b$, q is 0-4, where Z and W are independently selected from the group consisting of: CH$_2$, O, S, NR$^c$ and R$^b$, where R$^c$ is selected from the group consisting of: hydrogen, C$_1$-C$_4$ alkyl, and C$_3$-C$_6$ cycloalkyl, R$^b$ is selected from the group consisting of: hydrogen, C$_1$-C$_{12}$ alkyl, C$_1$-C$_{12}$ substituted alkyl, C$_3$-C$_8$ cycloalkyl, C$_3$-C$_8$ substituted cycloalkyl, C$_3$-C$_8$ heterocycloalkyl, and C$_3$-C$_8$ substituted heterocycloalkyl, or alternatively —C(=O)—Y forms an amide bond thru a nitrogen atom on Y in which case Y is a selected from the group consisting of: glycine, sarcosine, N,N-diemthyl glycine, alanine, valine, leucine, isoleucine, lysine, ornithine, arigine, serine, and theronine;

R$^3$ and R$^4$ are independently selected from the group consisting of: hydrogen, C$_1$-C$_{12}$ alkyl, C$_1$-C$_{12}$ substituted alkyl, C$_1$-C$_{12}$ alkenyl, C$_1$-C$_{12}$ substituted alkenyl, C$_1$-C$_{12}$ alkynyl, and C$_1$-C$_{12}$ substituted alkynyl, or optionally R$^3$ and R$^4$ together are bonded to form a fused bicyclic ring system or a spirocyclic ring system, where the fused ring is a C$_3$-C$_8$ heterocycloalkyl or C$_6$-C$_{10}$ aryl or C$_4$-C$_{10}$ heteroaryl;

each R$^6$ is independently selected from the group consisting of: hydrogen, deuterium, CH$_3$, F, $^{19}$F, and $^{18}$F;

wherein optionally Z and W are taken together to form a C$_3$-C$_8$ heterocycloalkyl or C$_4$-C$_{10}$ heteroaryl or bicyclic ring system in which one of the rings must be a C$_4$-C$_{10}$ heteroaryl;

and wherein any and all heterocyclic and heteroaryl rings contain up to four heteroatoms selected from the group consisting of: 0, N, and S;

with the proviso that when both Z and W are heteroatoms, the value of q cannot be 1;

and with the proviso that when R$^2$ is hydrogen, at least one of the R$^3$ or R$^4$ groups is not hydrogen;

or a tautomer and/or a pharmaceutically acceptable salt thereof.

In some embodiments, the compound is a compound of formula VI:

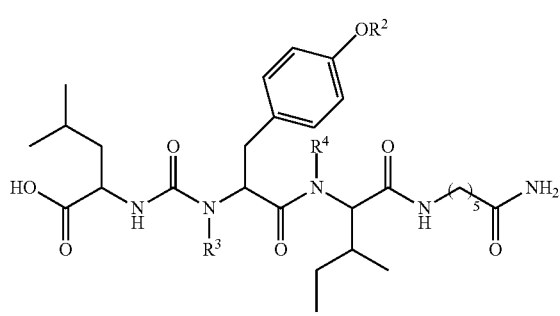

(VI)

wherein:
R$^2$ is selected from the group consisting of: hydrogen,

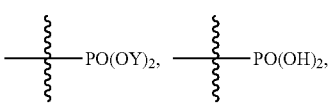

and —C(=O)—Y, where Y is —Z—(CH$_2$)$_q$—W—R$^b$, q is 0-4, where Z and W are independently selected from the group consisting of: CH$_2$, O, S, NR$^c$ and R$^b$, where R$^c$ is selected from the group consisting of: hydrogen, C$_1$-C$_4$ alkyl, and C$_3$-C$_6$ cycloalkyl, R$^b$ is selected from the group consisting of: hydrogen, C$_1$-C$_{12}$ alkyl, C$_1$-C$_{12}$ substituted alkyl, C$_3$-C$_8$ cycloalkyl, C$_3$-C$_8$ substituted cycloalkyl, C$_3$-C$_8$ heterocycloalkyl, and C$_3$-C$_8$ substituted heterocycloalkyl;

wherein optionally Z and W are taken together to form a C$_3$-C$_8$ heterocycloalkyl or C$_4$-C$_{10}$ heteroaryl or bicyclic ring system in which one of the rings must be a C$_4$-C$_{10}$ heteroaryl;

wherein any and all heterocyclic rings contain up to four heteroatoms selected from the group consisting of: O, N, and S;

with the proviso that when both Z and W are heteroatoms, the value of q cannot be 1;

or a tautomer and/or a pharmaceutically acceptable salt thereof.

In some embodiments, the compound is a compound of Formula I, where R$^1$ is a C$_5$ alkyl.

In some embodiments, the compound is a compound of Formula I, where R$^2$ is —C(=O)—Y, where Z is N, and Z and W taken together form a C$_5$ heterocycle.

In some embodiments, the compound is a compound of Formula I, where R$^2$ is

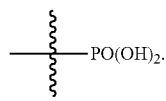

In some embodiments, the compound is a compound of Formula I, where R$^5$ is

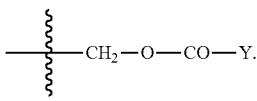

In some embodiments, the compound is a compound of Formula I, where R$^1$ is a C$_1$-C$_{12}$ alkyl, R$^3$ and R$^4$ are both hydrogen and R$^5$ is hydrogen.

In some embodiments, the compound is a compound of Formula II, where R$^1$ is C$_1$-C$_{12}$ alkynyl.

In some embodiments, the compound is a compound of Formula II, where R$^2$ is a —C(=O)—Y, where Z is CH$_2$, q is 0, W is N, and R$^3$ and R$^4$ together form a spirocyclic ring system where one ring is a C$_4$ heterocycle and the other is a C$_5$ cycloalkyl.

In some embodiments, the compound is a compound of Formula II, where m is 0, R$^1$ is a C$_1$-C$_{12}$ alkyl, and R$^3$ and R$^4$ together form a spirocyclic ring system.

In some embodiments, the compound is a compound of Formula II, where m is 1 or 2, R$^1$ is a C$_1$-C$_{12}$ alkyl, R$^3$ and R$^4$ together form a spirocyclic ring system, and R$^6$ is selected from the group consisting of: hydrogen, deuterium, F, $^{19}$F, and $^{18}$F.

In some embodiments, the compound is a compound of Formula III, where R$^1$ is a C$_5$ alkyl.

In some embodiments, the compound is a compound of Formula III, where R$^3$ and R$^4$ are both hydrogen and R$^2$ is

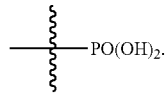

In some embodiments, the compound is a compound of Formula III, where $R^1$ is a $C_1$-$C_{12}$ alkyl, $R^2$ is —C(=O)—Y, and $R^3$ and $R^4$ are both hydrogen.

In some embodiments, the compound is a compound of Formula III where $R^1$ is a $C_1$-$C_{12}$ alkyl, $R^2$ is

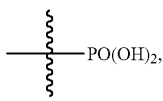

and $R^3$ and $R^4$ are both hydrogen.

In some embodiments, the compound is a compound of Formula IV, where n is 5, m is 1 or 2, and $R^6$ is selected from the group consisting of: hydrogen, deuterium, F, $^{19}F$, and $^{18}F$.

In some embodiments, the compound is a compound of Formula IV, where $R^5$ is a $C_5$ alkyl.

In some embodiments, the compound is a compound of Formula IV, where m is 1 or 2, $R^3$ and $R^4$ are both hydrogen, and $R^6$ is selected from the group consisting of: hydrogen, deuterium, F, $^{19}F$, and $^{18}F$.

In some embodiments, the compound is a compound of Formula IV, where m is 0, $R^3$ and $R^4$ are both hydrogen.

In some embodiments, the compound is a compound of Formula V, where $R^2$ is —C(=O)—Y, where Y is —Z—$(CH_2)_q$—W—$R^b$, q is 2, where Z is NH, W is $N(CH_3)$ and $R^b$ is $CH_3$.

In some embodiments, the compound is a compound of Formula V, where $R^3$ and $R^4$ together form a spirocyclic ring system.

In some embodiments, the compound is a compound of Formula V, where m is 1 or 2, $R^2$ is —C(=O)—Y, and $R^6$ is selected from the group consisting of: hydrogen, deuterium, F, $^{19}F$, and $^{18}F$.

In some embodiments, the compound is a compound of Formula V, where m is 1 or 2, $R^2$ is

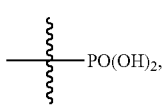

and $R^6$ is selected from the group consisting of: hydrogen, deuterium, F, $^{19}F$, and $^{18}F$.

In some embodiments, the compound is a compound of Formula VI, where $R^2$ is

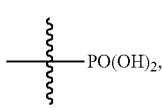

In some embodiments, the compound is a compound of Formula VI, where $R^2$ is hydrogen.

In some embodiments, the compound is a compound of Formula VI, where $R^2$ is —C(=O)—Y, and Z and W together form a $C_3$-$C_8$ heterocycloalkyl.

In some embodiments, the compound is a compound of Formula VI, where $R^2$ is

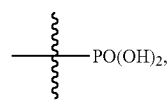

In some embodiments, the compound is a compound selected from the following structures:

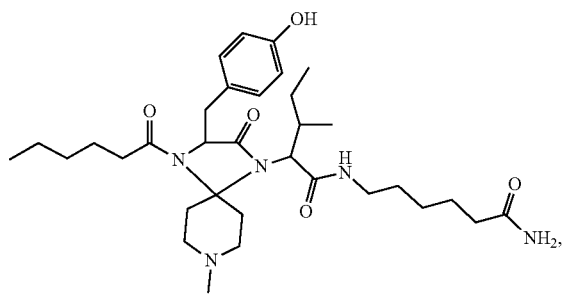

1

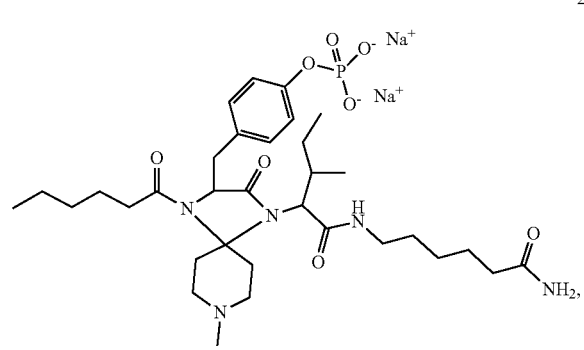

2

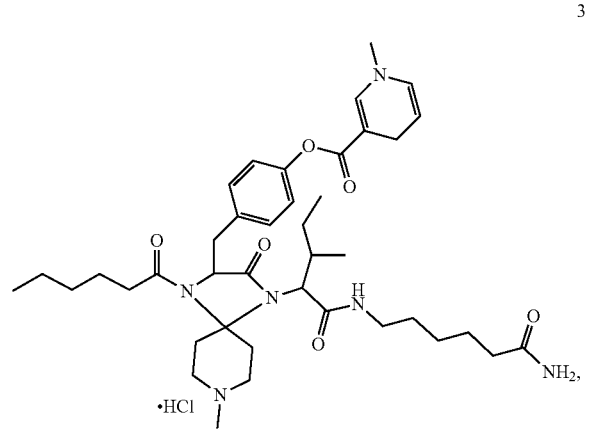

3

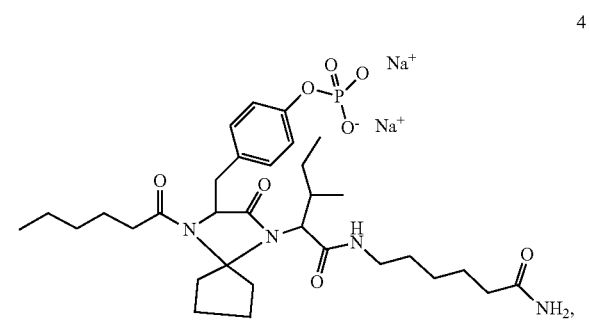

4

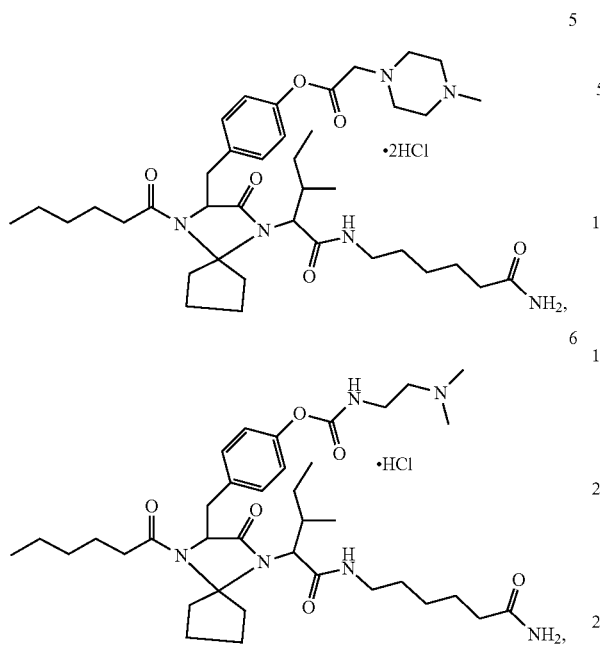
5
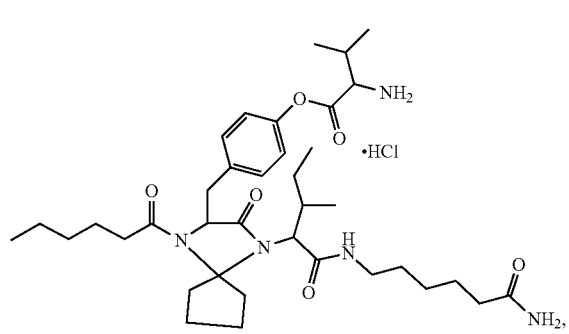
6
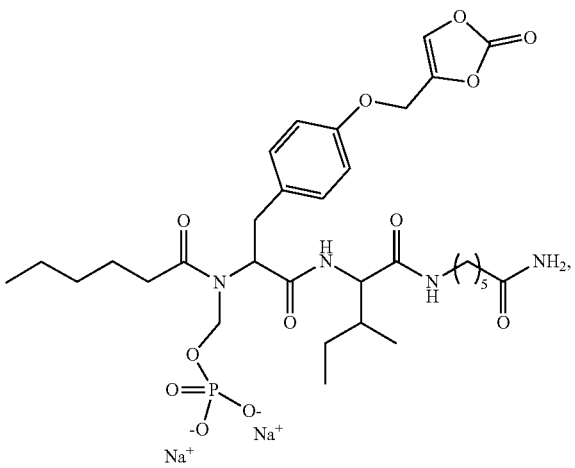
7
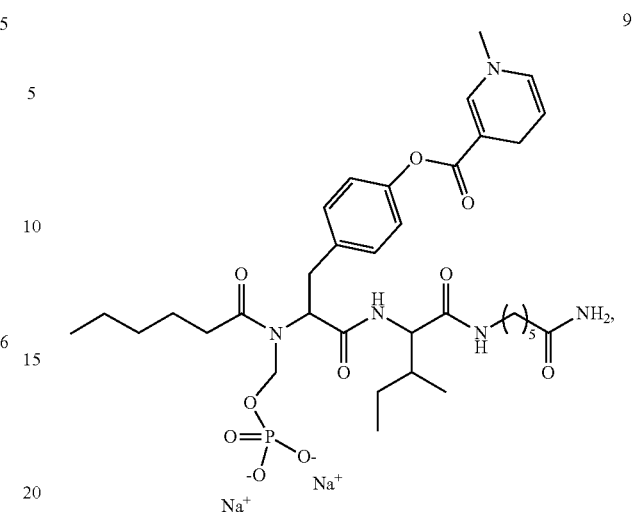
9
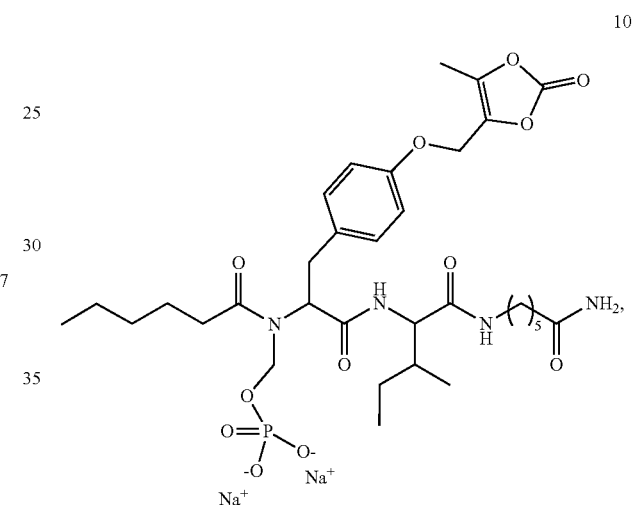
10
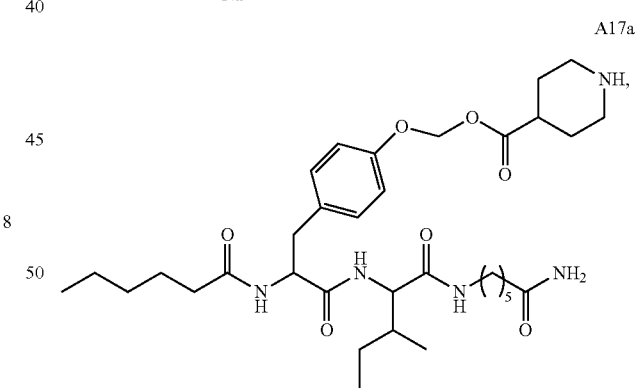
A17a
A17b

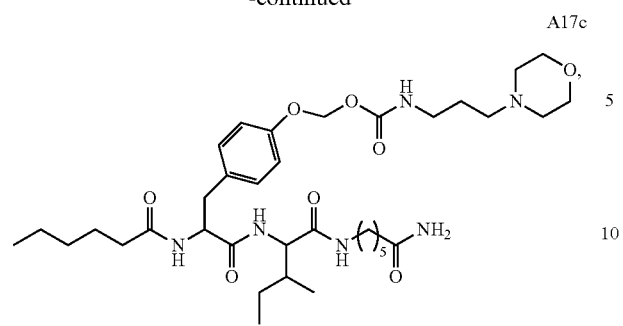
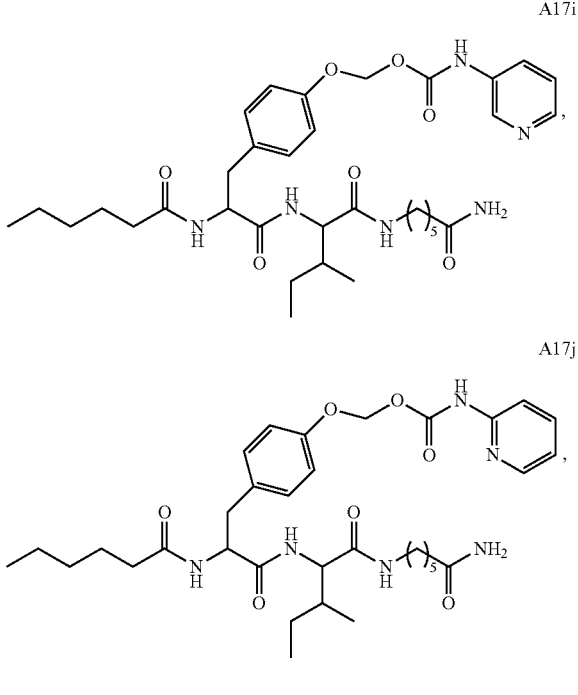
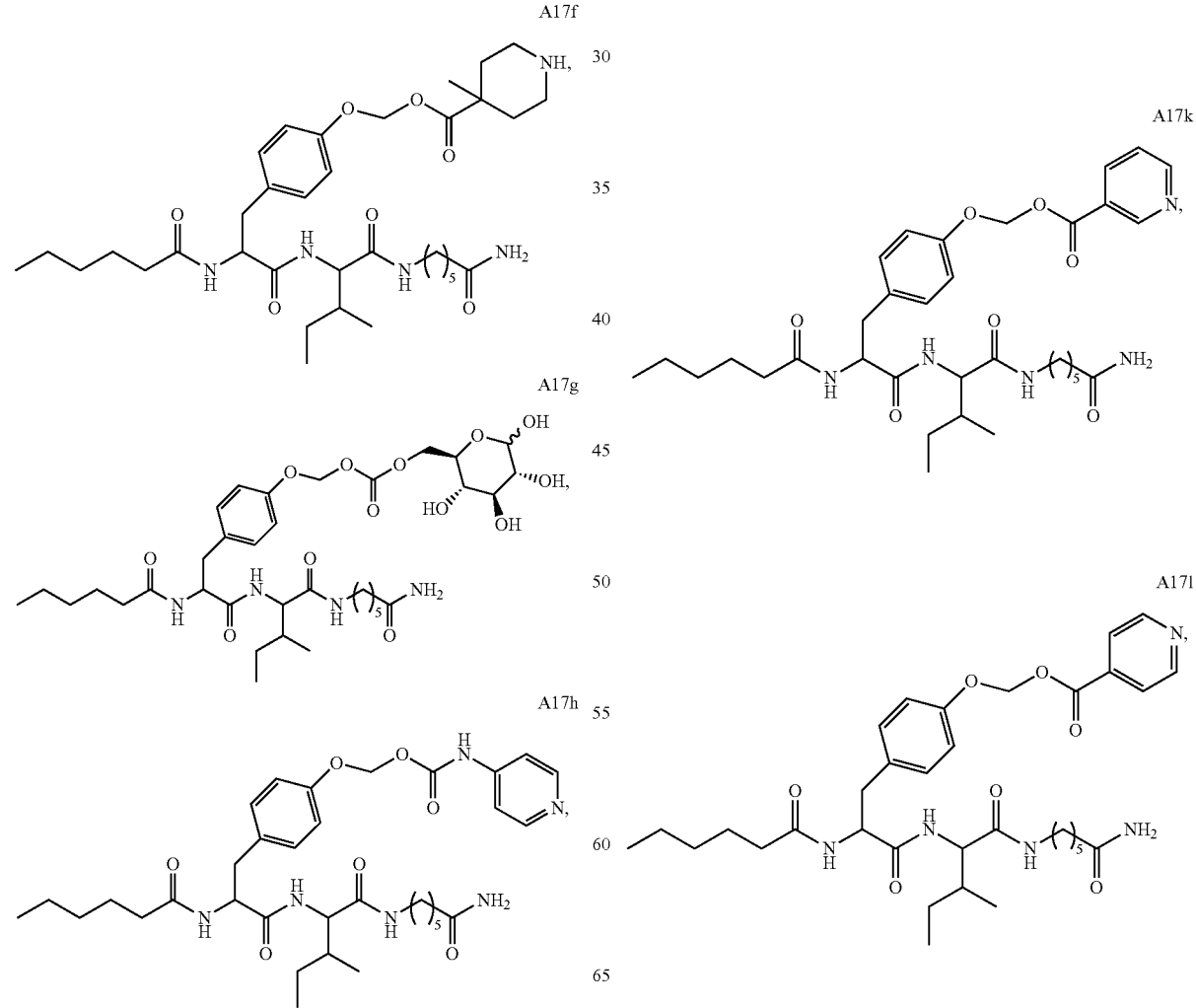

-continued
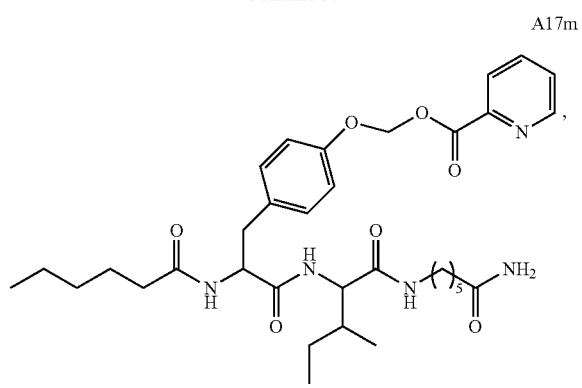
A17m
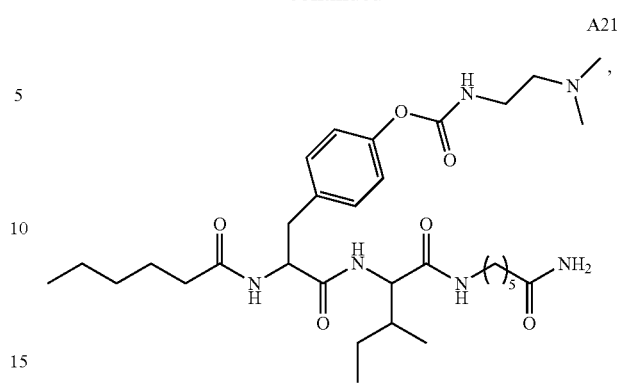
A21
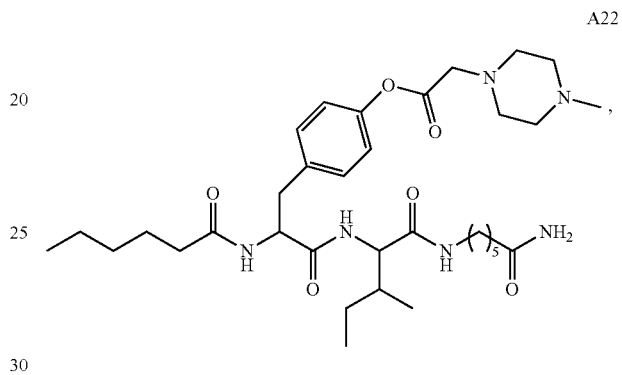
A22
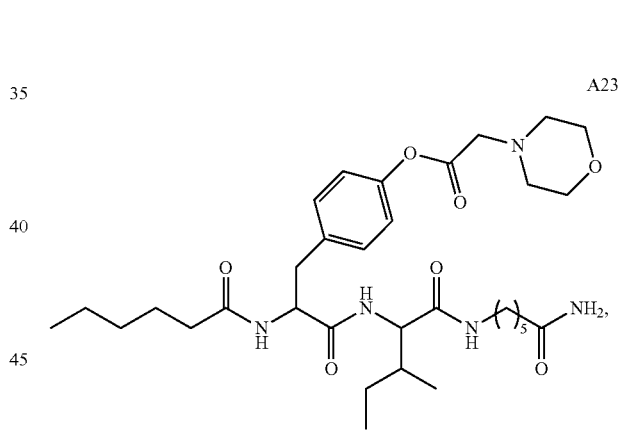
A23
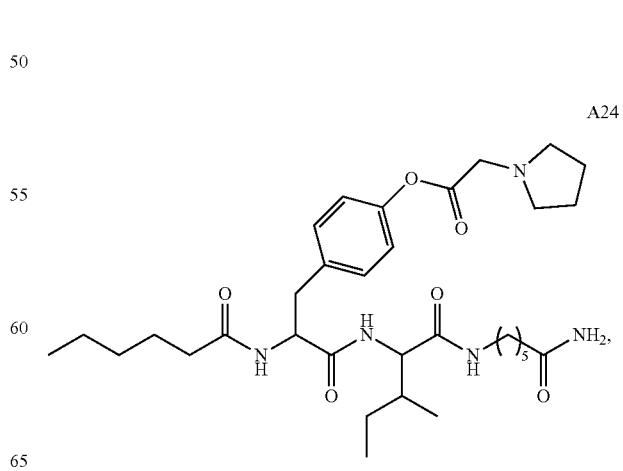
A24
A18
A19
A20

-continued
A25
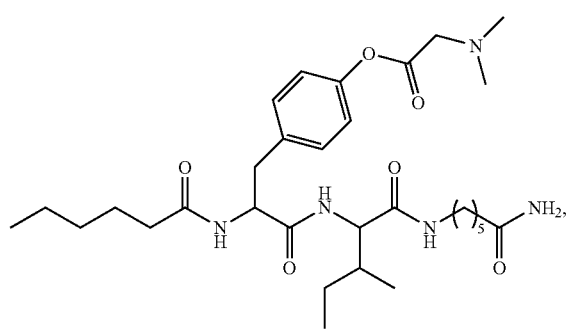
A26
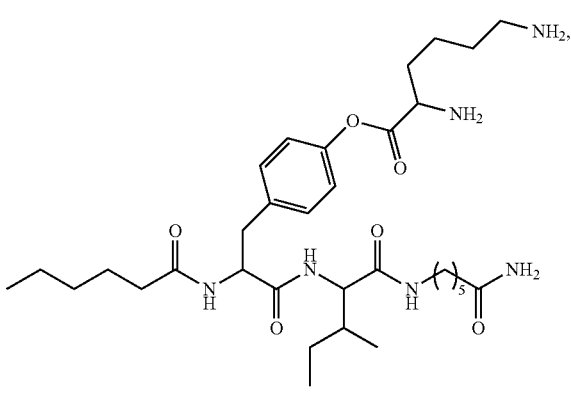
A27
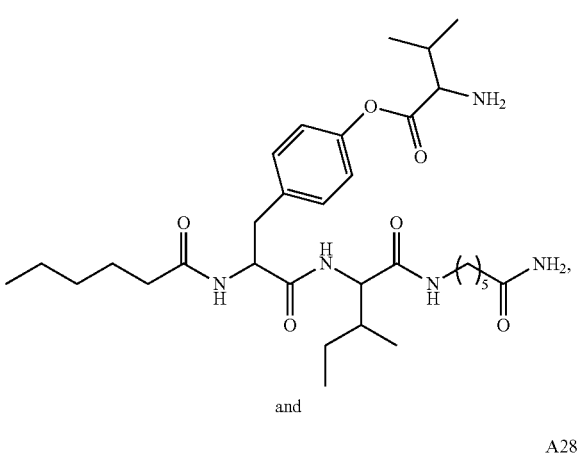
and
A28
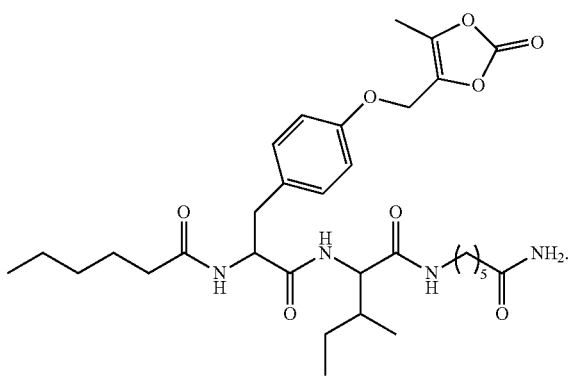
In some embodiments, the compound is a compound selected from the following structures:
B1
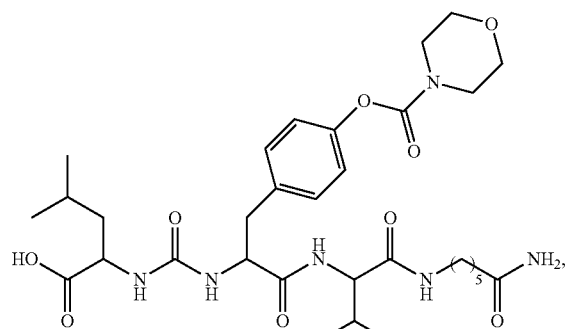
B2
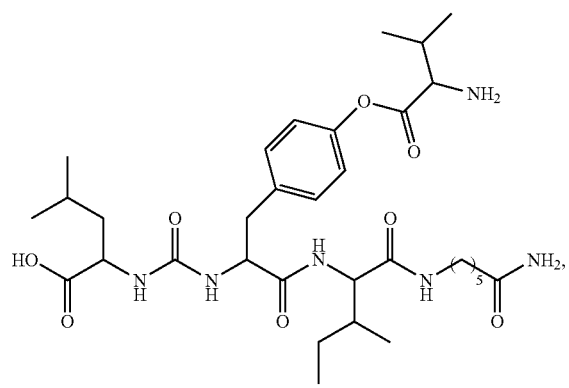
B3
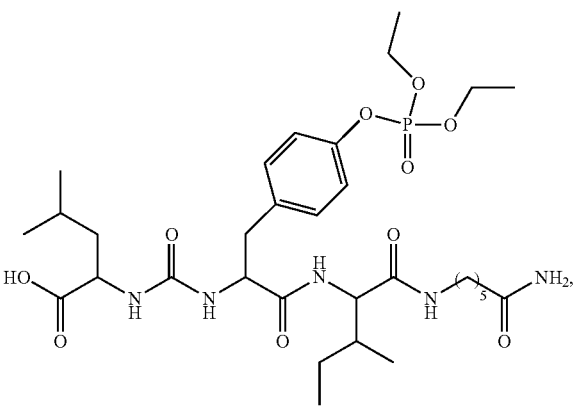
B4
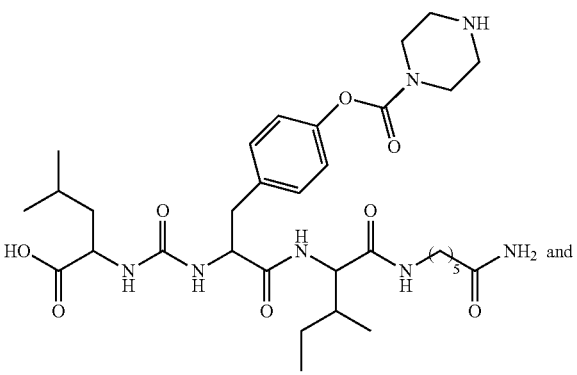
and

B5

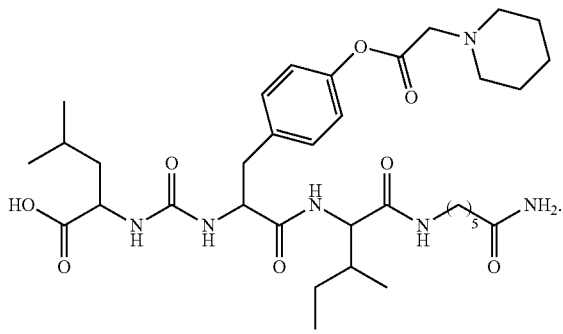

Synthesis

5.3.1. General Synthetic Methods

The compounds described herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactant or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional group are well known in the art. For example, numerous protecting groups are described in T. W. Greene and P. G. M. Wuts, Protecting Groups in Organic Synthesis, Third Edition, Wiley, New York, 1999, and references cited therein.

If the compounds described herein contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA), CombiChem (SAN DIEGO, CA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

5.3.2. Synthesis Routes to Described Compounds

The following specific, non-limiting examples are illustrative of the invention.

In one general embodiment, the method comprises reacting an appropriately N-protected compound with nucleophilic coupling partner and HATU to give the desired amide. It is appreciated that other suitable coupling conditions and reagents, such as HOBt and/or DMAP, may be used to form a requisite amide. The skilled artisan will appreciate that there are many synthetic conditions or methods by which an amide functional group can be made, for example by reacting the starting carboxylate to synthesize a reactive derivative such as the corresponding acid chloride and then reacting that intermediate directly with the amine nucleophile to produce the desired amide. These synthetic methods are well within in the scope of the present technology disclosed.

On the other hand, it is generally known that the N-terminus of di-peptide derivatives can be produced by first protecting or blocking (i.e. putting on the desired amide group on the C-terminus if the functional groups are compatible so as to not interfere with the subsequent steps in the overall synthesis of the compound and thus, are "orthogonal") the C-terminus and reacting the free di-peptide amine with an activated electrophile such as an acid anhydride, acid chloride, phosphorus oxychloride or phosphonyl chloride.

Of course it is recognized that esterification reactions may be used to generate non-trivial groups on the tyrosine moiety. Such reactions can be accelerated by using anhydrides, or other acid catalysts, when reacting the free alcohol with a reactive carboxy compound. Functional groups which are appropriate for active carboxy compound include, but are not limited to, anhydrides, acid chlorides, Mitsunobu conditions or Steglich-type conditions or anhydrous acid conditions with the carboxylic acid.

In one general embodiment, the synthesis can include functionalizing the nitrogen atoms of the amides on the di-peptide derivative. Such reactions are commonly accomplished by protecting sensitive functional groups on the rest of the molecule whilst generating an anion on one or both of the nitrogen by adding a strong base such as sodium amide, LDA, a Grignard reagent, or $LiN(i-Pr)_2$. Of course this list of bases is not comprehensive. The next step would be to add the appropriate electrophile. In the case where the artisan would like to make a spirocyclic ring system with the two nitrogen atoms of the di-peptide derivative, one could add a di-functionalized electrophile such as 1,1 di-bromo-cyclopentane, or even the requisite carbonyl compound under strong Lewis acidic conditions will work.

Herein it is understood that amino, keto, thio, hydroxyl, and any other necessary protecting groups and their methods of deprotection are known in the art, such as those described in T. W. Greene and P. G. M. Wuts, Protecting Groups in Organic Synthesis, Third Edition, Wiley, New York, 1999.

Alternatively, the skilled artisan will recognize that there is additional synthetic functional group modifications that one can use to prepare spirocyclic and other bicyclic or tricyclic compounds from dipeptide derivative intermediates.

5.4. Compositions

In another aspect, compositions are provided that comprise at least one compound as described herein.

In various embodiments, the compositions comprise one compound as described herein. In other embodiments, the compositions comprise a plurality of compounds as described herein. In certain of these latter embodiments, the compositions comprise 2, 3, 4, or 5 or more of the herein described compounds. In typical embodiments comprising a plurality of compounds, the compounds are selected to have pharmacokinetic properties different from one another.

In certain embodiments, the composition comprises at least one compound as described herein, and Base Structure. In various embodiments, the composition comprises 1, 2, 3, 4, or 5 compounds as described herein, and Base Structure. In typical embodiments, the compounds are selected to have pharmacokinetic properties different from Base Structure. In certain embodiments in which a plurality of compounds as described herein are included, the compounds are selected to have pharmacokinetic properties different from one another.

In various embodiments, the composition comprises at least one compound of Formula I, or tautomers, stereoisomers, salts, solvates or hydrates thereof.

In various embodiments, the composition comprises at least one compound of Formula II, or tautomers, stereoisomers, salts, solvates or hydrates thereof.

In certain embodiments, the composition comprises at least one compound selected from the group consisting of Compound 1, Compound 2, Compound 3, Compound 4, Compound 5, Compound 6, Compound 7, Compound 8, Compound 9, and Compound 10, as described herein above, or tautomers, stereoisomers, salts, solvates or hydrates thereof.

In certain embodiments, the composition comprises at least one compound selected from the group consisting of compound 1-10, A2-A17, A17a-17m, A18-A34f, and B1-B5 as described herein above, tautomers, stereoisomers, salts, solvates or hydrates thereof.

In various embodiments, the composition is a solid.

In various other embodiments, the composition is a liquid.

In various fluid embodiments, at least one of the at least one compound in the composition is present at a concentration of at least 10 ng/mL, 50 ng/mL, 100 ng/mL, 500 ng/mL, 1 ug/mL, 10 ug/mL, 50 ug/mL, 75 ug/mL, 0.1 mg/ml, 0.2 mg/ml, 0.3 mg/ml, 0.4 mg/ml, even at least 0.5 mg/ml. In some fluid embodiments, at least one of the at least one compound in the composition is present at a concentration of at least 1 mg/ml, 2 mg/ml, 3 mg/ml, 4 mg/ml or 5 mg/ml. In some fluid embodiments, at least one of the at least one compound in the composition is present at a concentration of at least 10 mg/ml, 20 mg/ml, 30 mg/ml, 40 mg/ml or 50 mg/ml. In some fluid embodiments, at least one of the compound in the composition is present at a concentration of at least 100 mg/ml, 125 mg/ml, 150 mg/ml, 175 mg/ml, or 200 mg/ml. In some fluid embodiments, at least one of the at least one compound in the composition is present at a concentration of at least 250 mg/ml.

In certain fluid embodiments, each of the at least one compound in the composition is present at a concentration of at least 0.1 mg/ml, 0.2 mg/ml, 0.3 mg/ml, 0.4 mg/ml, even at least 0.5 mg/ml. In some fluid embodiments, each of the at least one compound in the composition is present at a concentration of at least 1 mg/ml, 2 mg/ml, 3 mg/ml, 4 mg/ml or 5 mg/ml. In some fluid embodiments, each of the at least one compound in the composition is present at a concentration of at least 10 mg/ml, 20 mg/ml, 30 mg/ml, 40 mg/ml or 50 mg/ml. In some fluid embodiments, each of the at least one compound in the composition is present at a concentration of at least 100 mg/ml, 125 mg/ml, 150 mg/ml, 175 mg/ml, or 200 mg/ml. In some fluid embodiments, each of the at least one compound in the composition is present at a concentration of at least 250 mg/ml.

5.5. Pharmaceutical Compositions

In a further aspect, pharmaceutical compositions are provided that comprise at least one of the compounds described herein and a pharmaceutically acceptable carrier or excipient.

In various embodiments, the pharmaceutical compositions comprise one compound as described herein. In other embodiments, the pharmaceutical compositions comprise a plurality of compounds as described herein. In certain of these latter embodiments, the pharmaceutical compositions comprise 2, 3, 4, or 5 or more of the herein described compounds. In typical embodiments comprising a plurality of compounds, the compounds are selected to have pharmacokinetic properties different from one another.

In certain embodiments, the pharmaceutical composition comprises at least one compound as described herein, and Base Structure. In various embodiments, the pharmaceutical composition comprises 1, 2, 3, 4, or 5 compounds as described herein, and Base Structure. In typical embodiments, the compounds are selected to have pharmacokinetic properties different from Base Structure. In certain embodiments in which a plurality of compounds as described herein are included, the compounds are selected to have pharmacokinetic properties different from one another.

In various embodiments, the pharmaceutical composition comprises at least one compound of Formula I, or tautomers, stereoisomers, salts, solvates or hydrates thereof.

In various embodiments, the pharmaceutical composition comprises at least one compound of Formula II, or tautomers, stereoisomers, salts, solvates or hydrates thereof.

In certain embodiments, the pharmaceutical composition comprises at least one compound selected from the group consisting of Compound 1, Compound 2, Compound 3, Compound 4, Compound 5, Compound 6, Compound 7, Compound 8, Compound 9, and Compound 10, as described herein above, or tautomers, stereoisomers, salts, solvates or hydrates thereof.

In certain embodiments, the pharmaceutical composition comprises at least one compound selected from the group consisting of Compound 1-10, A2-A17, A17a-17m, A18-A34f, and B1-B5, as described herein above, tautomers, stereoisomers, salts, solvates or hydrates thereof.

In various embodiments, the pharmaceutical composition is formulated for enteral route of administration.

Pharmaceutical compositions for enteral route of administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included. A pharmaceutical composition can include a cyclodextrin. A pharmaceutical composition can contain poloxamer and/or Vitamin E TPGS.

In embodiments in which the pharmaceutical composition is formulated for enteral route of administration in a solid dosage form, the composition will contain, on a weight percent (wt %) basis, from about 0.01-99.99 wt % of the compound of the present technology based on the total formulation, with the balance being one or more suitable pharmaceutical excipients. Preferably, the compound is present at a level of about 1-80 wt %.

In other embodiments, the pharmaceutical composition is formulated for inhalation suspended in solutions or mixtures of excipients (e.g., preservatives, viscosity modifiers, emulsifiers, buffering agents) in non-pressurized or pressurized dispensers that deliver a spray containing a metered dose of at least one compound as described herein. In certain inhalation embodiments, the pharmaceutical composition is formulated for nasal or oral administration.

In other embodiments, the pharmaceutical composition is formulated for topical administration. In certain topical embodiments, the pharmaceutical composition is formulated for enepidermic route, Epidermic route, Instillation administration, or Painting/Swabbing.

In other embodiments, the pharmaceutical composition is formulated for parenteral administration. In certain parenteral embodiments, the pharmaceutical composition is formulated for intravenous, subcutaneous, or intradermal administration. In other embodiments, the pharmaceutical composition is formulated for intrathecal or intracerebroventricular administration.

In typical parenteral embodiments, the composition will be in the form of a parenterally acceptable aqueous solution that is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In various fluid embodiments, at least one of the compound in the pharmaceutical composition is present at a concentration of at least 0.1 mg/ml, 0.2 mg/ml, 0.3 mg/ml, 0.4 mg/ml, even at least 0.5 mg/ml. In some fluid embodiments, at least one of the at least one compound in the pharmaceutical composition is present at a concentration of at least 1 mg/ml, 2 mg/ml, 3 mg/ml, 4 mg/ml or 5 mg/ml. In some fluid embodiments, at least one of the at least one compound in the pharmaceutical composition is present at a concentration of at least 10 mg/ml, 20 mg/ml, 30 mg/ml, 40 mg/ml or 50 mg/ml. In some fluid embodiments, at least one of the at least one compound in the pharmaceutical composition is present at a concentration of at least 100 mg/ml, 125 mg/ml, 150 mg/ml, 175 mg/ml, or 200 mg/ml. In some fluid embodiments, at least one of the at least one compound in the pharmaceutical composition is present at a concentration of at least 250 mg/ml.

In certain fluid embodiments, each of the at least one compound in the pharmaceutical composition is present at a concentration of at least 0.1 mg/ml, 0.2 mg/ml, 0.3 mg/ml, 0.4 mg/ml, even at least 0.5 mg/ml.

In some fluid embodiments, each of the at least one compound in the pharmaceutical composition is present at a concentration of at least 1 mg/ml, 2 mg/ml, 3 mg/ml, 4 mg/ml or 5 mg/ml. In some fluid embodiments, each of the at least one compound in the pharmaceutical composition is present at a concentration of at least 10 mg/ml, 20 mg/ml, 30 mg/ml, 40 mg/ml or 50 mg/ml. In some fluid embodiments, each of the at least one compound in the pharmaceutical composition is present at a concentration of at least 100 mg/ml, 125 mg/ml, 150 mg/ml, 175 mg/ml, or 200 mg/ml. In some fluid embodiments, each of the at least one compound in the pharmaceutical composition is present at a concentration of at least 250 mg/ml.

5.6. Methods of Use

In another aspect, methods of treatment are provided.

The methods comprise administering at least one compound as described herein to a subject in an amount effective to treat, protect from, or reverse neurodegenerative disease, to prevent or reverse the symptoms of dementia, to facilitate repair of traumatic injury to the nervous system, or to enhance cognitive function. In various embodiments, the subject has a disease selected from Alzheimer's disease, Parkinson's disease, amyotrophic lateral sclerosis, other dementias and neurodegenerative diseases, spinal cord injury, traumatic brain injury, and/or sensorineural hearing and vision loss. In typical embodiments, the method comprises administering a pharmaceutical composition comprising at least one of the compounds described herein, as described above.

In some aspects, a method for treating a disease state or condition is provided for, the method comprising administration of an effective amount of one or more compounds of the formulae as disclosed herein or a pharmaceutical composition as disclosed herein to a subject in need thereof.

In some aspects, a method for treating a disease state or condition is provided for, where the disease is neurodegenerative disease.

In some aspects, a method for treating a disease state or condition is provided for, where the disease is selected from the group consisting of: Alzheimer's disease, Parkinson's disease, amyotrophic lateral sclerosis, other dementias and neurodegenerative diseases, spinal cord injury, traumatic brain injury, sensorineural hearing and vision loss.

In some aspects, a method for treating a disease state or condition is provided for, where the disease is Alzheimer's disease.

In some aspects, a method for treating a disease state or condition is provided for, where the disease is Parkinson's disease.

In some aspects, a method for treating a disease state or condition is provided for, where wherein the route of administration is selected from the group consisting of: enteral, parenteral, inhalation, topical including but not limited to oral, intravenous, subcutaneous, intrathecal, and intracerebroventricular administration.

In some aspects, a method for treating a disease state or condition is provided for, where the administration is intravenous.

In some aspects, a method for treating a disease state or condition is provided for, where the method is performed in-vitro. In some aspects, a method for treating a disease state or condition is provided for, where the method is performed in-vivo.

In some aspects, a method for treating a disease state or condition is provided for, where the subject is a mammal. In some aspects, a method for treating a disease state or condition is provided for, where the subject is a human.

In some aspects, the use of one or more compounds disclosed herein is provided for in the manufacture of a medicament for treating a disease state or condition described herein.

In various embodiments, the compound is administered as the sole medical treatment. In various embodiments, the compound is administered in combination with other medical and/or surgical interventions according to the prevailing standards of care.

In various embodiments, the dose is determined without regard to patient weight. In certain embodiments, the dose is between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. Additionally, a dose can be administered daily or alternatively, a few times a week, where the subsequent dose is administered after 1, 2 or 3 day interval.

In some embodiments, the dose is determined based on patient weight. In certain embodiments, the dose is between 0.001 mg/kg patient weight to about 15 mg/kg per kg patient weight per administration, or 0.01 mg/kg to about 1.5 mg/kg.

The amount of compound administered will vary depending upon the disease treated, the route of administration, and the dosage schedule.

It will be understood, however, that the specific dose level for any particular subject will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

Therapy can extend for a number of days, a number of weeks or months, and in some cases, years.

A composition can be administered alone or in combination with other treatments, either simultaneously or sequentially dependent upon the condition to be treated.

Dosage amount and dosage schedule may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

6. EXAMPLES

The following synthetic and biological examples are offered to illustrate this the present technology and are not to be construed in any way as limiting the scope of this the present technology. Unless otherwise stated, all temperatures are in degrees Celsius.

The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ *Ed*. (Plenum Press) Vols A and B(1992), and Organic Reactions, Volumes 1-40 (John Wiley, and Sons, 1991).

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. +If an abbreviation is not defined, it has its generally accepted meaning.

aq.=aqueous
LC-MS=liquid chromatography-mass spectrometry
MS=mass spectrometry
THF=tetrahydrofuran
NaHCO$_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trI zolo[4,5-b]pyridinium 3-oxid hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
Na$_2$CO$_3$=sodium carbonate
NMR=nuclear magnetic resonance
NaOH=sodium hydroxide
Na$_2$SO$_4$=sodium sulfate
TLC=thin layer chromatography
UV=ultraviolet
wt %=weight percent
µM=micromolar

6.1. Example 1: Syntheses

General Experimental Details

Final compounds were confirmed by HPLC/MS analysis and determined to be ≥90%. $^1$H and $^{13}$C NMR spectra were recorded in CDCW (residual internal standard CHCW=δ 7.26), DMSO-d$_6$ (residual internal standard CD$_3$SOCD$_2$H=δ 2.50), methanol-d$_4$ (residual internal standard CD$_2$HOD=δ 3.20), or acetone-d$_6$ (residual internal standard CD$_3$COCD$_2$H=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

In general, the compounds of the present invention may be prepared as illustrated in the general reaction schemes described below, or by modifications thereof, using readily available starting materials, reagents, and conventional synthesis procedures, or could be inferred by one skilled in the art. Generally, compounds of the Formula I, may be prepared by standard solution phase or solid-phase synthesis from commercially available inputs by procedures well established in the art. For example, acylation of the amino terminal would then provide a common intermediate A2. The tyrosyl hydroxyl group of A2 can be acylated with a carboxylic acid derivative (A3), which may be a N—BOC protected amino-acid (such as α, β, γ or ω amino acid, or a di-amino acid derivative such as Lys or Orn) followed by removal of the amine protecting group under acidic conditions to provide A4 (Scheme 1 below).

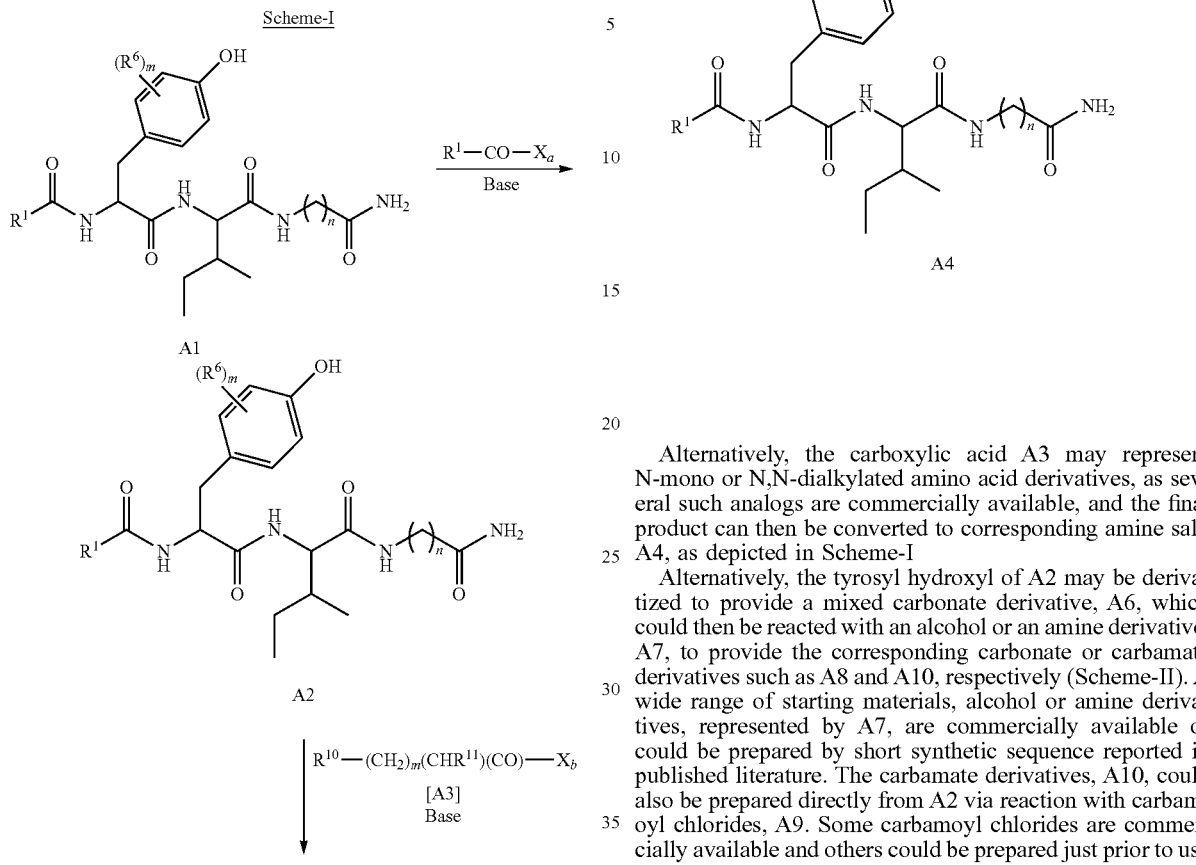

Scheme-I

A1

A2

A4

Alternatively, the carboxylic acid A3 may represent N-mono or N,N-dialkylated amino acid derivatives, as several such analogs are commercially available, and the final product can then be converted to corresponding amine salt, A4, as depicted in Scheme-I Alternatively, the tyrosyl hydroxyl of A2 may be derivatized to provide a mixed carbonate derivative, A6, which could then be reacted with an alcohol or an amine derivative, A7, to provide the corresponding carbonate or carbamate derivatives such as A8 and A10, respectively (Scheme-II). A wide range of starting materials, alcohol or amine derivatives, represented by A7, are commercially available or could be prepared by short synthetic sequence reported in published literature. The carbamate derivatives, A10, could also be prepared directly from A2 via reaction with carbamoyl chlorides, A9. Some carbamoyl chlorides are commercially available and others could be prepared just prior to use from corresponding secondary amine and diphosgene.

Scheme-II

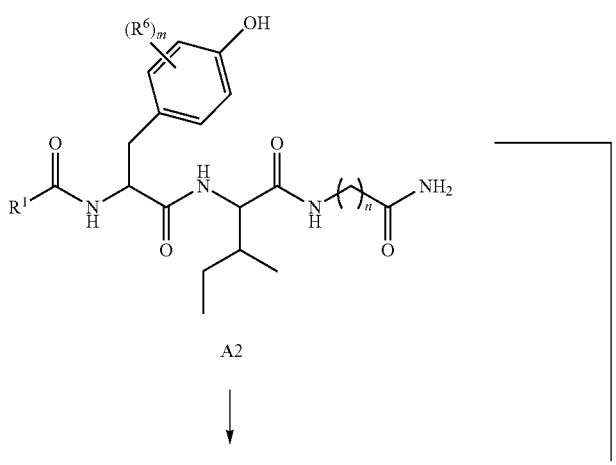

A2

-continued
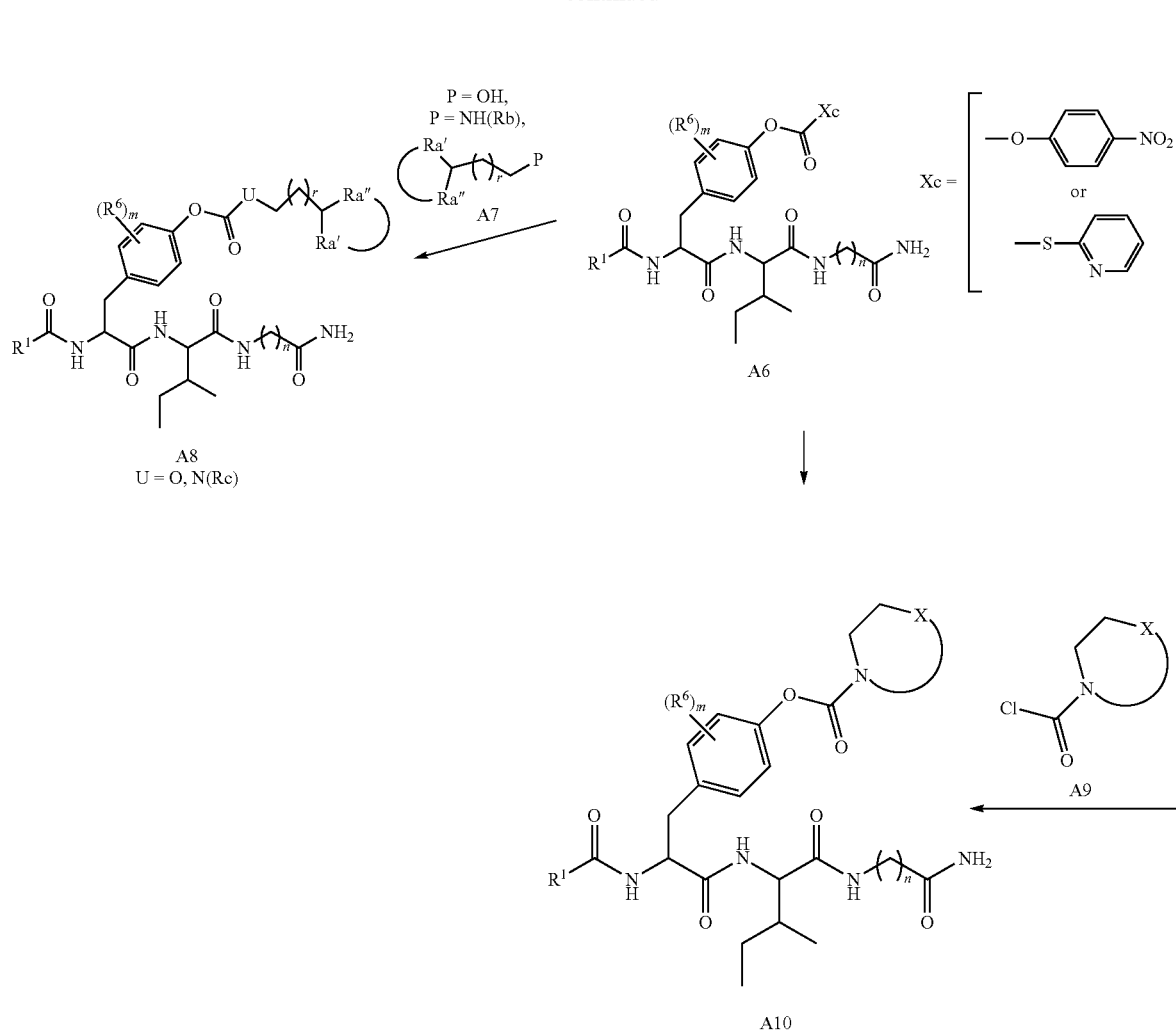
Tyrosyl hydroxyl could be converted to phosphate derivatives A12, A13, A15, as shown in Scheme-III. The reaction with 2-eq of appropriate alcohols with either POCl3 or 4-nitrophenyl phosphorodichloridate provides intermediate A14, which is then used to derivatize the phenolic hydroxyl of A2 to provide a desired product, A15.
Scheme-III
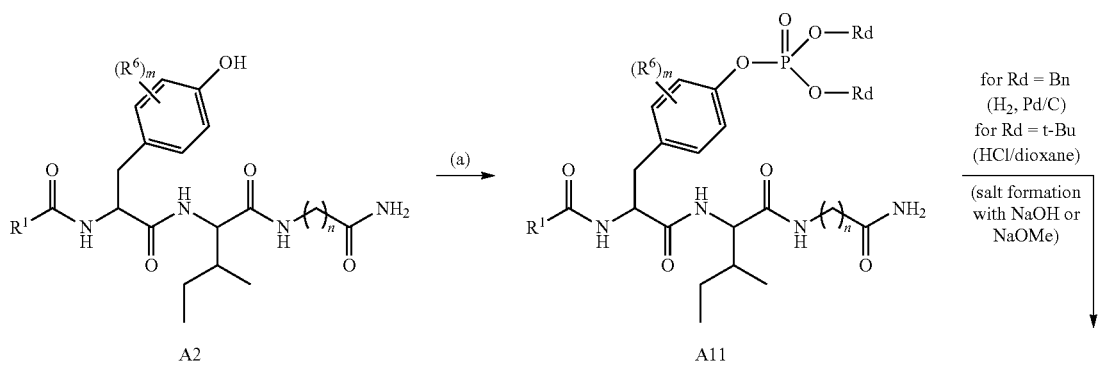

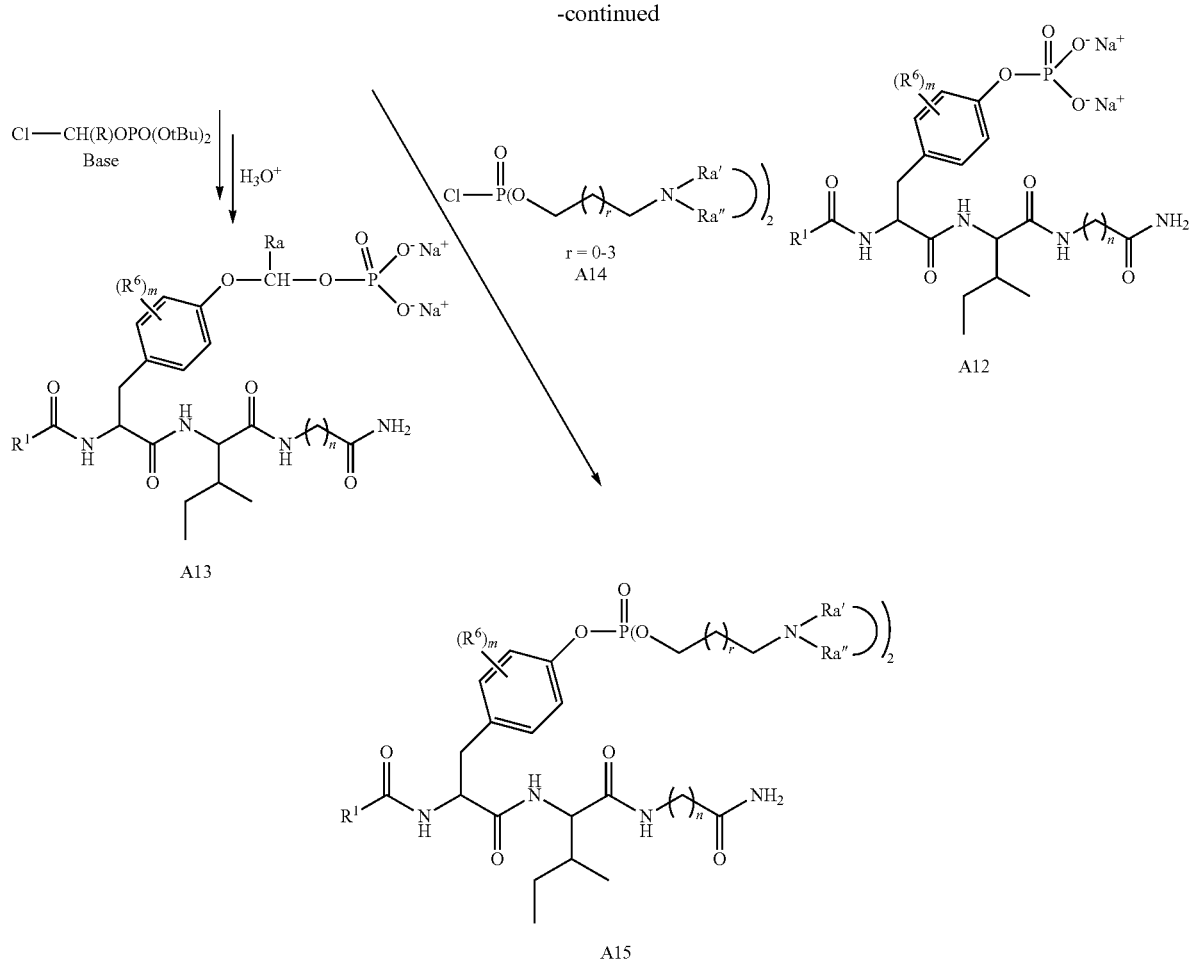

Another variant of R2 derivatives where the prodrug moiety represents alkoxy-carbonyl based-derivatives can be prepared by route and chemistries shown in Scheme IV. For alkylation of A2, the alkoxy-carbonyl reagents, A16, where the amine is protected with an acid labile BOC group can be prepared utilizing the chemistries, as outlined in Scheme V, or via commercially available reagents. Table 1 below represents some non-limiting examples of these derivatives as a R2 substituent, where A17g represents an example of non-amine based, polyhydroxyl solubility enhancing moiety.

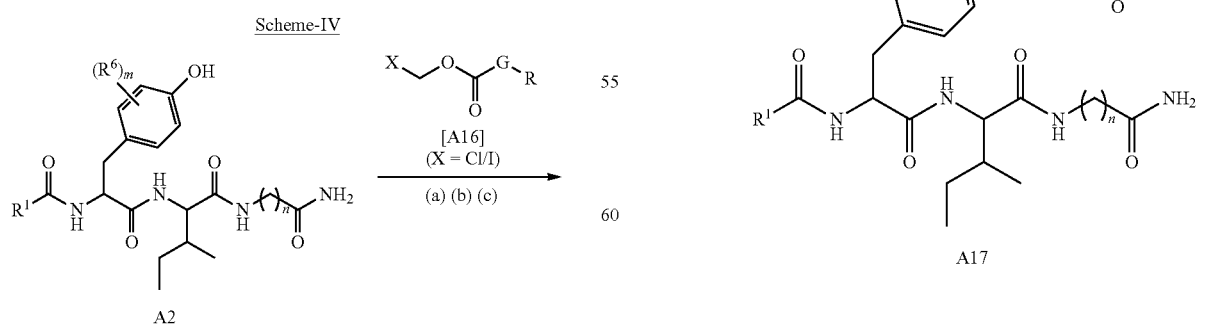

Scheme V: Preparation of Prodrug moiety (A16).
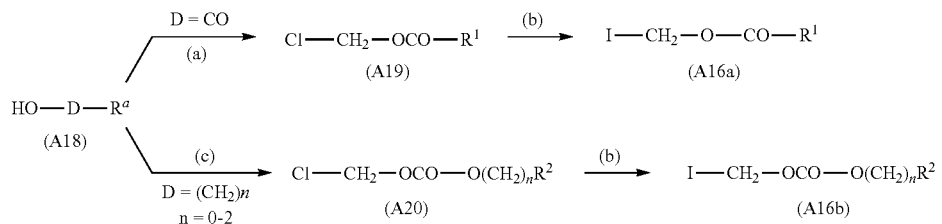
Reagents: (a) Cl—CH$_2$—OSO$_2$Cl, aq. NaHCO3, CH$_2$Cl$_2$
(b) NaI/acetone (if required),
(c) Cl—CH$_2$—OCOCl, base,
TABLE 1
Representative Examples of Alkoxy-carbonyl-derived compounds, for simplicity shown for
$R^6 = H$
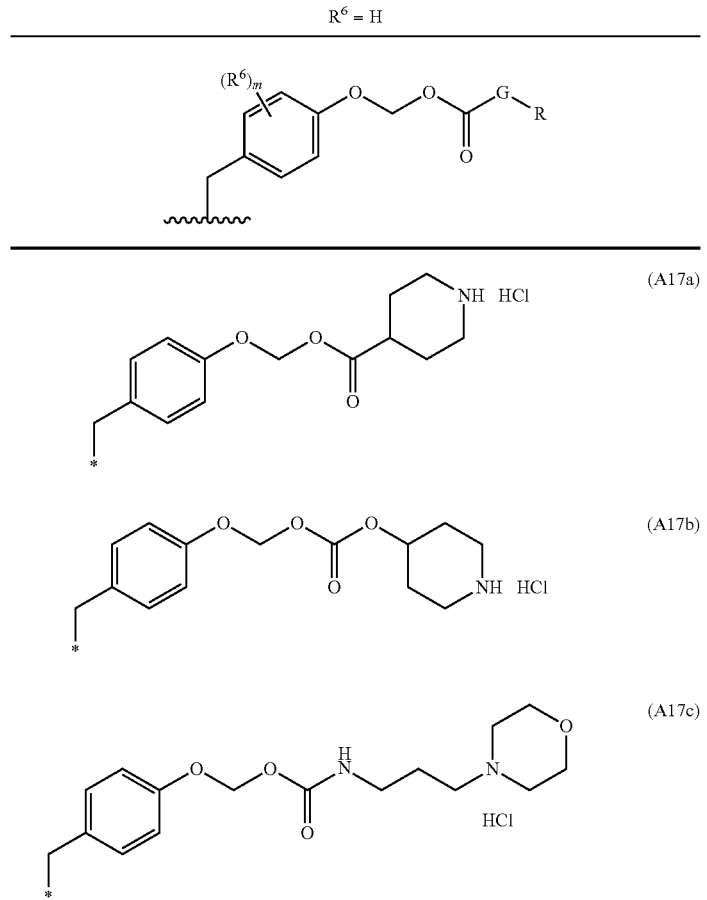

TABLE 1-continued

Representative Examples of Alkoxy-carbonyl-derived compounds, for simplicity shown for $R^6 = H$

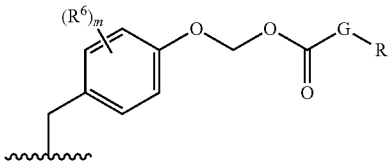

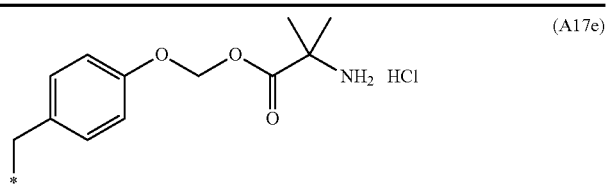

(A17e)

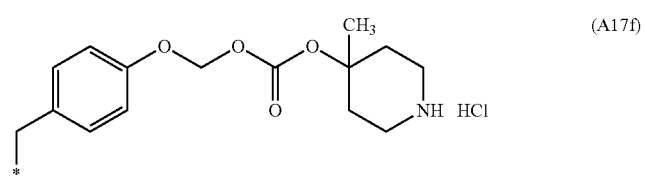

(A17f)

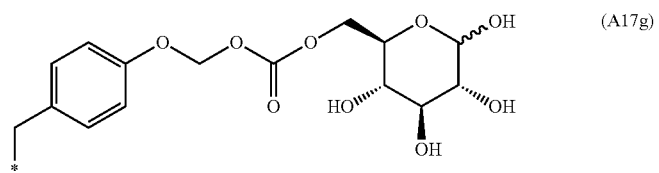

(A17g)

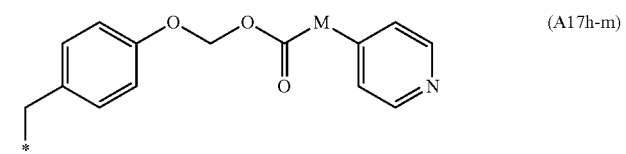

(A17h-m)

[M = covalent bond or CH$_2$], also 2-Py, 3-Py

Chemistries for incorporation of R3-R4 bicyclic derivatives are shown in the Schemes below. When symmetrical acyclic or cyclic ketones are used for ring formation, no new chiral center will be produced. However, unsymmetrical ketone or aldehyde derived cyclization will generate a new chiral center. The cyclization is expected to proceed via the intermediacy of a Schiff's base, and since chirally pure peptide derivative will be used, one would expect to obtain a thermodynamically stable cyclic-aminal (imidazolidinone) product. A literature report by Lydie, H. et. al. Tett. Letters (2015) 6240-6243, provides an example of cyclization reaction using 2-pyridine carboxaldehyde with a dipeptide, which provides two diastereomers in 46% and 11% yield]. The R3-R4 bridged mono- and/or spirocyclic aminals can be prepared either under acidic or base catalyzed conditions such as similar to or variations of conditions reported in the literature, such as, by, Gomes, P. et. al. Tetrahedron, 2004, 5551-62, DeMong. D. et. al. J. Med. Chem. 2014, 57, 2601-10, and reference cited therein. Subsequent N-acylation of A23A, followed by hydrogenation and removal of the acid labile protecting group, where applicable, will provide the target imidazolidinone derivatives A24A, Scheme VI.

Scheme VI

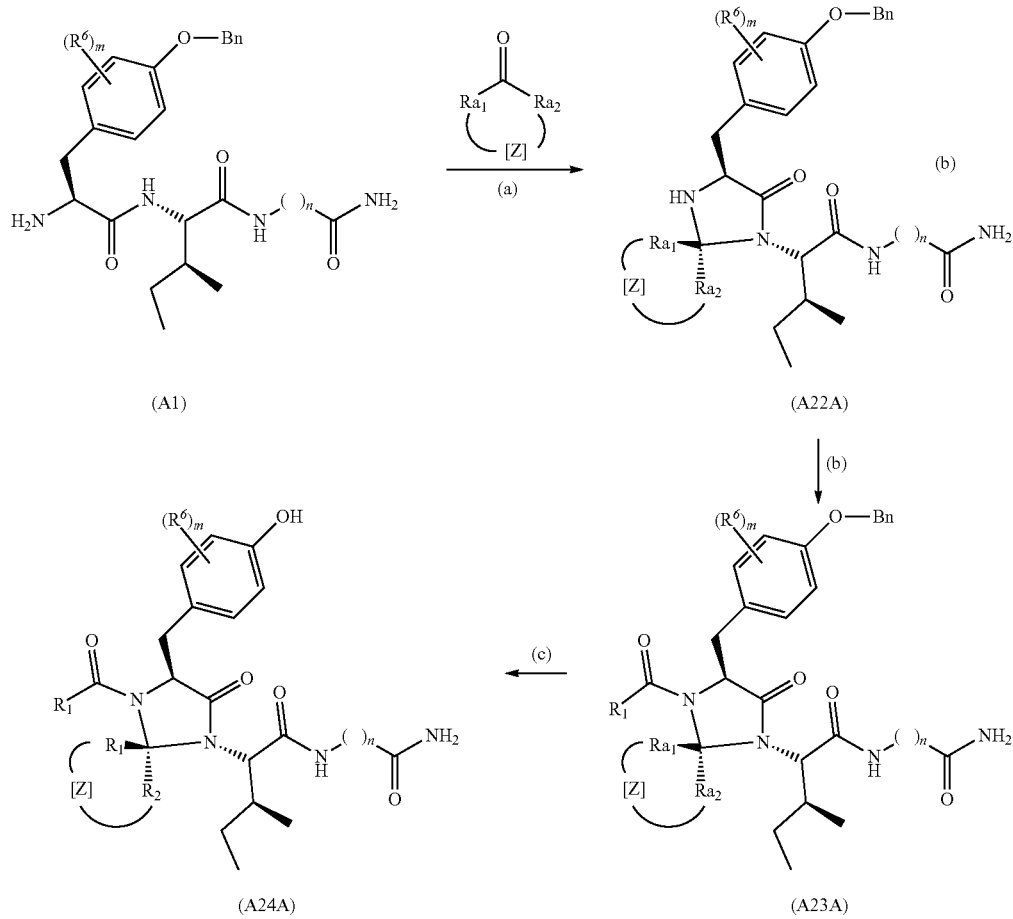

Reagents: (a) Cat. acid (pTSA or HOAc), in ROH (MeOH, EtOH, IPA) rt or gentle heat,
(b) R¹COCl or (R¹—CO)₂O, Et₃N, THF or DMF,
(c) H₂—Pd/C EtOH/IPA or galc. HOAc, RT, Alternatively, reaction of dipeptide (A25A) with a carbonyl compound could be used to prepare the cyclic aminals, A26A (Scheme VII). Subsequent N-acylation, followed by the coupling reaction shown, should provide the desired key intermediate (A23A), which would then be elaborated further as shown in Scheme VI.

Scheme VII

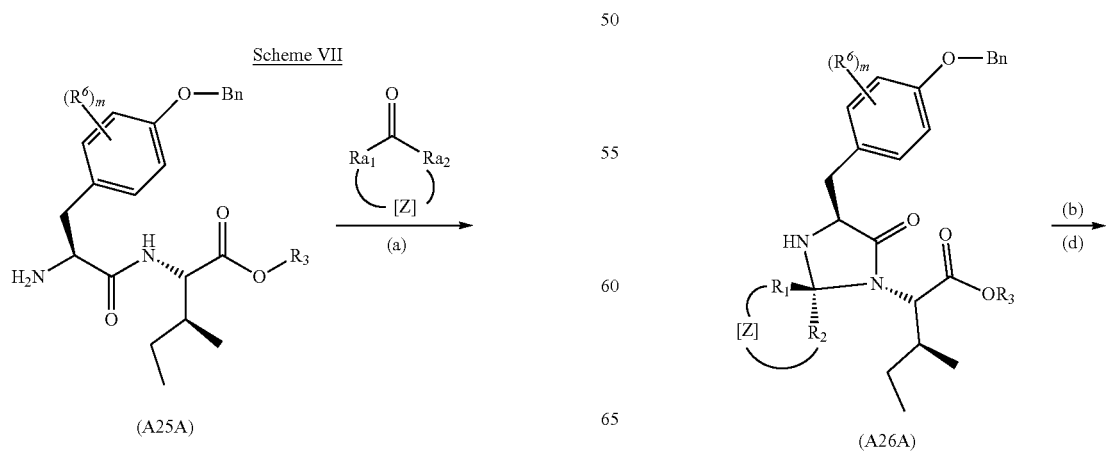

-continued

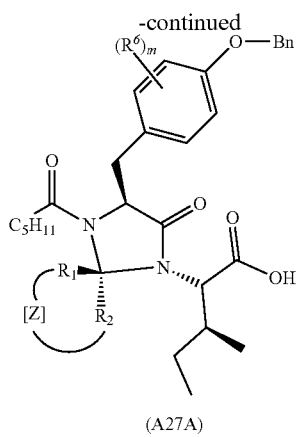

(A27A)

Reagents: (a) Cat. acid (pTSA or HOAc), in ROH (MeOH, EtOH, IPA) rt or gentle heat, (b) R₁COCl or (R₁—CO)₂O, Et₃N, THF or DMF,
(c) H₂—Pd/C EtOH/IPA or galc. HOAc, RT, (d) R₃ = TBDMS, 0.5-1M aq HCl
(e) EDCI, HOBt, NH₂—(CH₂)n—CONH₂

The alkoxy-carbonyl bearing an amino group can also be introduced at the C-terminal amide, which following esterase mediated bioconversion should regenerate A2. The chemistry to prepare reagents [A16] is similar to the one described above in Scheme V, except the prodrug generating reagents [A16] contains a CBZ protected amine. Some examples of the reagents used are shown in the box (insert) in Scheme VIII. Following synthesis of the protected penultimate intermediate, the final hydrogenation step in the presence of an acid would provide the desired prodrug derivative A33A.

Scheme VIII, C-terminal Amide Prodrugs

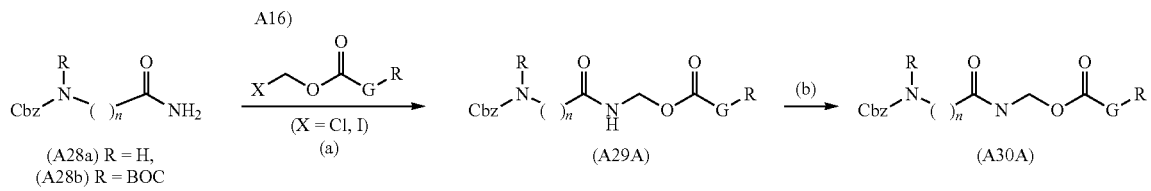

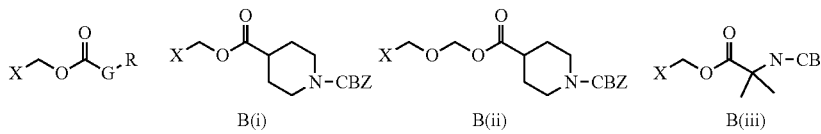

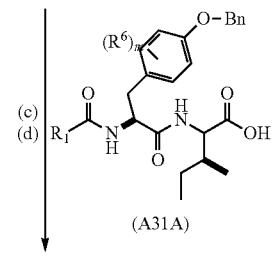

(see Scheme 2b for synthetic approaches)

Prepared via solid-phase or solution synthesis

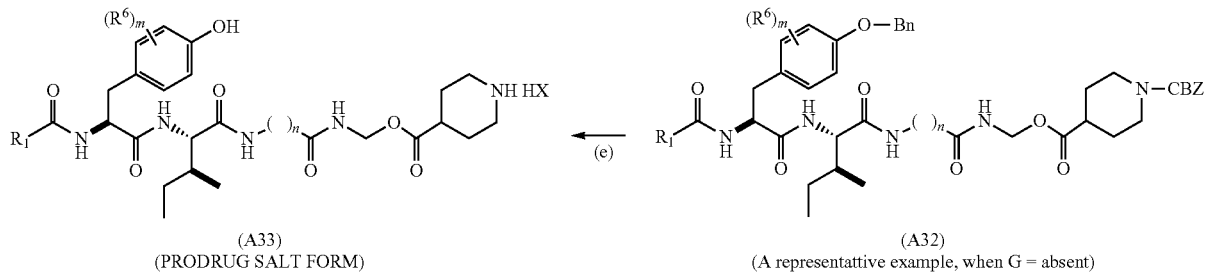

Reagents: (a) Cs₂CO₃, DMF, (b) 4M HCl/p-dioxane, (C) H2/Pd/c, (d) HATU, HBOT, DMF or EDCI, HOBt, DMF,
(e) H₂/Pd—C glac HOAc/aq. HCl (1-1.5 eq.)

One may also be able to prepare derivatives incorporating dual prodrug moieties, one at the Tyr and other at the C-terminal amide, or at R3/R4 bridge and at R2, or some combination of the chemistries described above. As an example, dual prodrug analogs from one of these approaches, and corresponding proposed synthetic route, is shown in Scheme IX, below.

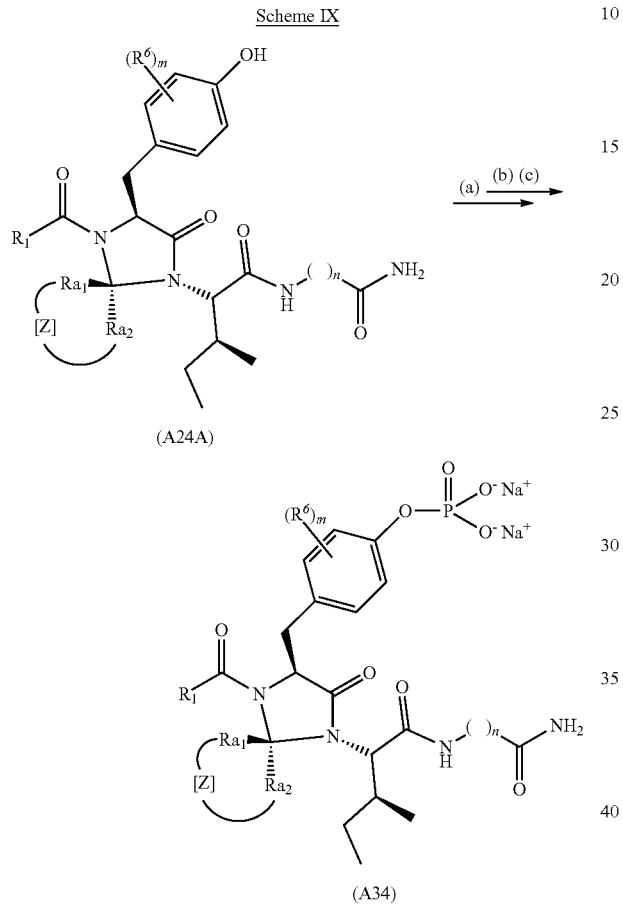

(a) (BnO)₂PO—O—PO(OBn)₂/ (non-aq) Base/DMF, (b) H₂/Pd—C, glac HOAc, (c) salt formation, (e.g. Ion-exchange resin)

Some Examples of (Cyclic Aminal) Imidazolidinone Fragments: CH(Ra)O

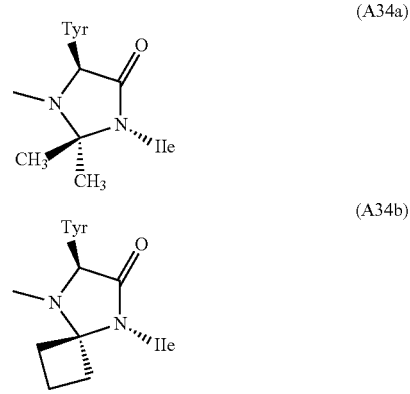

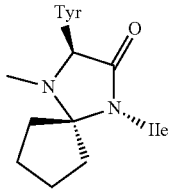

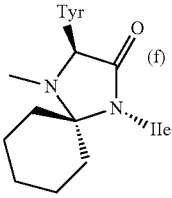

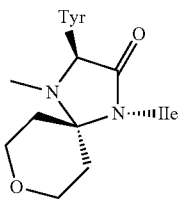

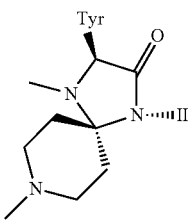

Furthermore, the tyrosine analogs with R6 variants such as F, $^2$H and $CH_3$ are reported in the published primary literature and/or in the patents and references cited therein. [For $(R_6)_m$ as $^2$H: 2,6-didetutero tyrosine, Nishiyama, B. et. al. J. Labeled Compounds and Radiopharmaceuticals, 1994, 34(9), 831-37; 2,3,4,6-tetradeutero tyrosine: Walker, T. E. et al. al J. Org Chem. 1986, 51(8), 1775-79; for $(R_6)_m$ as $CH_3$: 2-methyl tyrosine, Schmidt, E. W. Tett. Letters, 2004, 3921-24; for 2,3-dimethyl tyrosine or 2,5-dimethyl tyrosine, Santagada, V. J. Med. Chem. 2006, 49(6), 1882-90, for 2,6-dimethyl tyrosine EP1481965A1 (2004) and EP2959918A1 (2015); and for $(R_6)_m$ as F: 2,6- or 2,3- or 2,4-difluoro and/or 2,3,5- or 2,3,6-trifluoro tyrosine, Seyedsayamdost, H. et. al. J. Am. Chem. Soc 2006, 49(6), 1882-90; and 2,3,5,6-tetrafuloro tyrosine is commercially available.] In addition, the derivative of A2 where R6 is 2-fluoro, such derivatives should be accessible via regiospecific electrophilic fluorination of the tyrosine-containing peptide or peptide mimetics utilizing in-situ generated CH3COOF, as described by Hebel, D., Tett. Letters, 1990, 31(5), 619-622. Other such R6 derivatives should be accessible from extension of these chemistries.

The following specific, non-limiting examples are illustrative of the invention.

Example-1A

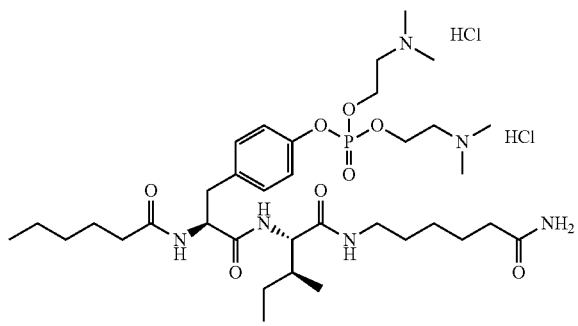

To a mixture of 4-nitrophenyl phosphorodichloridate (504 mg, 1.98 mmol) in THF (30 mL) at 0° C. was added, 2-(dimethylamino)ethanol (397 µL, 3.97 mmol) and stirred for two hours at room temperature. THF was evaporated and crude product was dissolved in DMF (20 mL) followed by addition of Base Structure (500 mg, 0.992 mmol) and LiOH·H$_2$O (208 mg, 4.96 mmol) and the mixture was stirred at room temperature overnight. Quenched with 4 Molar HCl, concentrated, washed (DCM/CH$_3$CN), and purified by preparative HPLC using Isocratic 40% MeOH vs 60% aqueous formic acid solution (0.1%), pure fractions were combined, (HCl Salt was formed by addition of 4 Molar HCl) to give the title compound, as a white solid, after lyophilization. [(obs) MH$^+$=727.5]

Example-1B

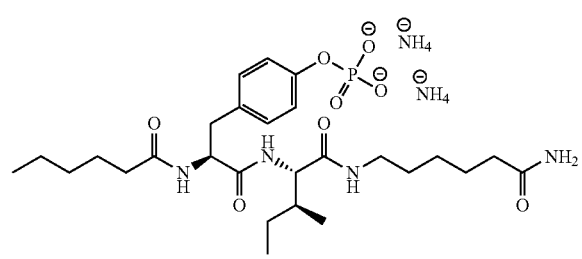

Step-1: A mixture of Base Structure (500 mg, 0.992 mmol) in DMF, tetrabenzyl diphosphate (587 mg, 1.09 mmol) and LiOH·H$_2$O (46 mg, 1.09 mmol) was stirred at room temperature overnight. Concentrated, washed (DCM) and used in the next step without further purification.

Step-2: 4-((S)-3-((2S,3S)-1-(6-amino-6-oxohexylamino)-3-methyl-1-oxopentan-2-ylamino)-2-hexanamido-3-oxo-propyl)phenyl dibenzyl phosphate was dissolved in acetic acid (15 mL) and 10% Pd/C 0.5 eq (w/w) was added and stirred for two hours under hydrogen atmosphere. Reaction mixture was filtered through a pad of celite. Filtrate was concentrated, washed (DCM) and purified by preparative HPLC (Isocratic 70% MeOH vs 30% ammonium acetate buffer (pH 8) to give the desired compound after lyophilization as a white solid (NH$_4^+$ Salt). [(obs) MH$^+$=684.5]

Example-1C

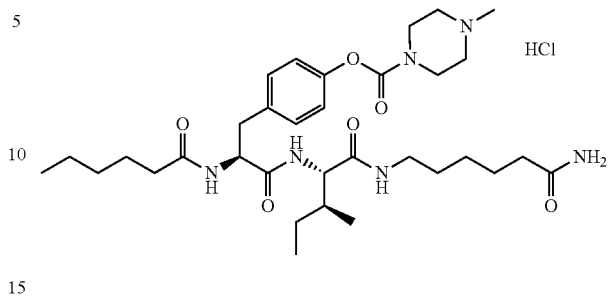

Base Structure (564.9 mg, 1.119 mmol) was dissolved in dry DMF (12 mL) then LiOH·H$_2$O (46.9 mg, 1.119 mmol) and bis(4-nitrophenyl)carbonate (374.6 mg, 1.231 mmol) were added. The solution was stirred at room temperature under nitrogen atmosphere for 17 h. N-methylpiperazine hydrochloride (198.8 mg, 1.455 mmol) was added and the mixture stirred for another 6 h then quenched with HCl and concentrated to dryness. The solid was washed (DCM, EtOAc) then purified by Biotage C-18 reverse phase flash chromatography (30%-100% MeOH vs 0.1% aqueous formic acid) to give the title compound Base Structure-C-PIPM (227.6 mg, 30%) after treatment with HCl and lyophilization. [(obs) MH$^+$=631.4 and M+Na$^+$=653.4]

Example-1D

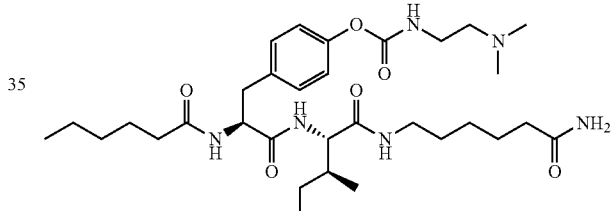

Base Structure (508.1 mg, 1.007 mmol) was dissolved in dry DMF (8 mL) then LiOH·H$_2$O (42.2 mg, 1.007 mmol) and bis(4-nitrophenyl)carbonate (336.9 mg, 1.107 mmol) were added. The solution was stirred at room temperature under nitrogen atmosphere overnight. N,N-dimethylethane-1,2-diamine hydrochloride (163.1 mg, 1.309 mmol) was added and the mixture stirred for another 4 h then quenched with HCl and concentrated to dryness. The solid was washed (DCM, EtOAc) then purified by preparative HPLC (50%-70% MeOH vs 0.1% aqueous formic acid) to give the title compound (154.8 mg, 12%) after treatment with HCl and lyophilization. [(obs) MH$^+$=619.5 and M+Na$^+$=641.6]

Example-1E

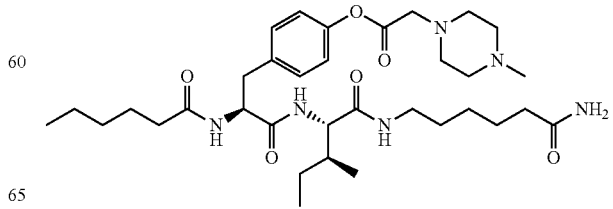

To a solution of Base Structure (200 mg; 0.39 mmol) and 2-(4-methylpiperazin-1-yl)acetic acid (175.6 mg; 1.1 mmol) in anhydrous DMF (15 mL), EDC HCl (247.3 mg; 1.3 mmol) and HOBt (61 mg; 039 mmol) were added at 0° C. The mixture was warmed to room temperature and stirred overnight. The reaction was quenched with 4M HCl in 1,4-dioxane (0.5 mL). The solvent was evaporated in vacuum and the solid material was dissolved in methanol (2 mL). Product was precipitated by adding diethylether to the above solution, and was separated by filtration. Crude product was purified by reverse phase HPLC using methanol (B): 0.1% formic acid in water (D), [gradient elution; 10 to 100% of B vs D in 20 min]. The combined fractions were acidified with HCl and lyophilized to offer the compound (206 mg, 82%) as white solid. [(obs) MH$^+$=645.4]

Example-1F

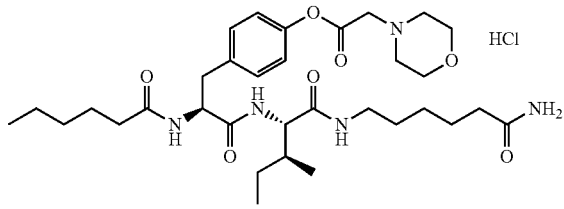 [SMILES: CCCCCC(=O)N[C@@H](Cc1ccc(OC(=O)CN2CCOCC2)cc1)C(=O)N[C@H](C(=O)NCCCCCC(N)=O)[C@@H](C)CC ; Cl]

Step-1: A mixture of 2-morpholinoacetic acid (975 mg, 6.73 mmol), 4-nitrophenol (850 mg, 6.12 mmol), DCC (1386 mg, 6.73 mmol) and DMAP (40 mg, 0.306 mmol) in DCM (50 mL) was stirred at room temperature overnight. Reaction mixture was filtered, concentrated and washed with DCM gave 4-nitrophenyl 2-morpholinoacetate as a white solid which was used in the next step without further purification.

Step-2: A mixture of 4-nitrophenyl 2-morpholinoacetate (288 mg, 0.95 mmol), Base Structure (400 mg, 0.79 mmol), and LiOH·H$_2$O (74 mg, 1.75 mmol) in DMF (10 mL) was stirred at room temperature overnight. Quenched with 4 molar HCl, Concentrated and washed (DCM/THF/CH$_3$CN) gave the desired compounds as a white solid (HCl Salt). [(obs) MH$^+$=632.5, M+Li$^+$=638.5]

Example-1G

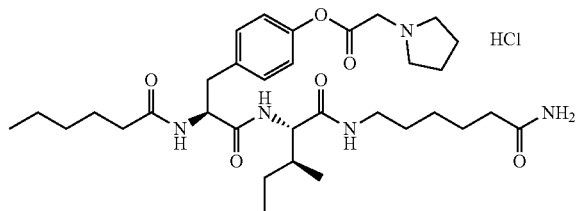 [SMILES: CCCCCC(=O)N[C@@H](Cc1ccc(OC(=O)CN2CCCC2)cc1)C(=O)N[C@H](C(=O)NCCCCCC(N)=O)[C@@H](C)CC ; Cl]

Step-1: A mixture of 2-(pyrrolidin-1-yl)acetic acid hydrochloride (1000 mg, 6.06 mmol), 4-nitrophenol (842 mg, 6.06 mmol), DCC (1500 mg, 7.27 mmol) and DMAP (39 mg, 0.30 mmol) in CH$_3$CN (50 mL) was stirred at room temperature overnight. Reaction mixture was filtered, concentrated and washed with DCM gave 4-nitrophenyl 2-(pyrrolidin-1-yl)acetate hydrochloride as yellow viscous oil which was used in the next step without further purification.

Step-2: A mixture of 4-nitrophenyl 2-(pyrrolidin-1-yl) acetate hydrochloride (187 mg, 0.66 mmol), Base Structure (300 mg, 0.59 mmol), and LiOH·H$_2$O (55 mg, 1.31 mmol) in DMF (10 mL) was stirred at room temperature overnight. Quenched with 4 molar HCl, concentrated, washed (DCM/CH$_3$CN) and purified by preparative HPLC using isocratic 40% MeOH and 60% 0.1% aqueous formic acid solution gave the desired compounds as a white solid 4 molar HCl was added to make HCl Salt of the final product) after lyophilization. [(obs) MH$^+$=616.5 and M+Na$^+$=638.4]

Example-1H

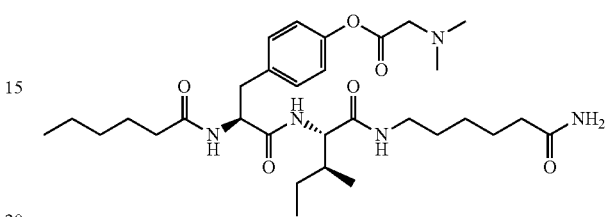

To a solution of Base Structure (200 mg; 0.39 mmol) and 2-(dimethylamino) acetic acid (124.4 mg; 1.1 mmol) in anhydrous DMF (15 mL), EDC HCl (191.7 mg; 1 mmol) and HOBt (61.2 mg; 0.39 mmol) were added at 0° C. The mixture was warmed to room temperature and stirred overnight. The reaction was quenched with 4M HCl in 1,4-dioxane (0.5 mL). The solvent was evaporated in vacuum and the solid material was dissolved in methanol (2 mL). Product was precipitated by adding diethylether to the above solution, and was separated by filtration. The crude product was purified by reverse phase HPLC using methanol (B): 0.1% formic acid in water (D), [gradient elution; 10 to 100% of B vs D in 20 min]. The combined fractions were acidified with HCl and lyophilized to offer as white solid (94 mg 40%). In addition, 63 mg of Base Structure was also recovered from this reaction. [(obs) MH$^+$=590.4 and M+Na$^+$=612.4]

Example-1I

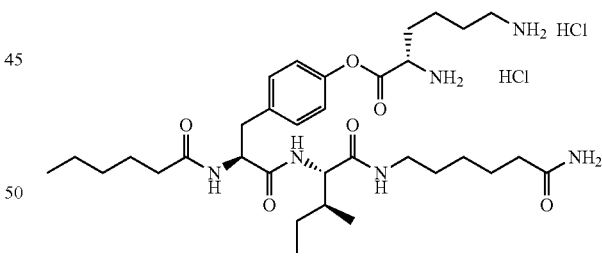

Step-1: A mixture of Boc-(S)-Lys(Boc)-OH (741 mg, 2.14 mmol), 4-nitrophenol (282.7 mg, 2.03 mmol), DCC (441.3 mg, 2.14 mmol) and DMAP (26.1 mg, 0.214 mmol) in dry acetonitrile (20 mL) was stirred at room temperature under nitrogen atmosphere overnight. Reaction mixture was filtered, concentrated and crude product was purified by flash chromatography (silica gel, hexanes/EtOAc) to provide (S)-4-nitrophenyl 2,6-bis(tert-butoxycarbonylamino) hexanoate (548.7 mg, 55%).

Step-2: (S)-4-nitrophenyl 2,6-bis(tert-butoxycarbonylamino)hexanoate (512.0 mg, 1.095 mmol) in solution in dry DMF (5 mL) was added to a solution of Base Structure (460.6 mg, 0.9127 mmol) and LiOH·H$_2$O (40.2 mg, 0.958 mmol). The mixture was stirred at room temperature under nitrogen atmosphere overnight. Concentration and washing (DCM, acetonitrile) gave bis(Boc-protected)-(578.2 mg, 76%).

Step-3: Bis(Boc-protected)-(307.1 mg, 0.369 mmol) was stirred in a DMF (1.5 mL)/4N HCl in dioxane (8 mL) mixture at room temperature for 3.5 h then concentrated, washed (DCM) and purified by preparative HPLC (40%-100% MeOH vs 0.1% aqueous formic acid), after treatment with HCl and lyophilisation provided the title compound (204.1 mg, 68%). [(obs) $MH^+$=633.5 and $M+Na^+$=655.6]

Example-1J

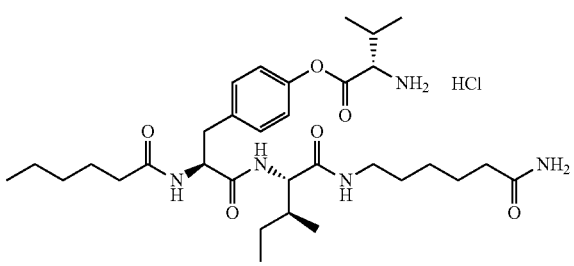 [SMILES: CCCCCC(=O)N[C@@H](Cc1ccc(OC(=O)[C@@H](N)C(C)C)cc1)C(=O)N[C@H](C(=O)NCCCCCC(N)=O)[C@@H](C)CC ; Cl]

Step-1: To a solution of 4-nitrophenol (1 g, 7.2 mmol) and (S)-2-(tert-butoxycarbonylamino)-3-methylbutanoic acid (1.8 g, 8.6 mmol) in anhydrous acetonitrile (25 mL), was added DCC (1.8 g, 8.6 mmol) and DMAP (44 mg, 0.36 mmol). The mixture was stirred overnight under nitrogen atmosphere. The solvent evaporated in vacuum and crude mixture was purified by normal phase column chromatography using DCM (100%) as eluent to offer (S)-4-nitrophenyl-2-(tert-butoxycarbonylamino)-3-methylbutanoate (0.7 g, 29%).

(S)-4-nitrophenyl-2-(tert-butoxycarbonylamino)-3-methylbutanoate and Base Structure (300 mg; 0.59 mmol) was dissolved in anhydrous DMF (25 mL). LiOH $H_2O$ (24.9 mg, 0.59 mmol) was added to the solution. The mixture was stirred at room temperature under nitrogen atmosphere overnight. The solvent was evaporated in vacuum, solid material was washed with DCM (100%) and then acetonitrile (100%) to offer pure BOC-protected-product (300 mg), which was dissolved in a mixture of DMF (3 mL) and 1,4-dioxane (1 mL). 4 M HCl in 1,4-dioxane (10 mL) was added to the above solution. The mixture was stirred at room temperature for 4 h. The solvent was evaporated in vacuum and the crude product was purified by reverse phase HPLC using methanol (B): 0.1% formic acid in water (D), [gradient elution; 40 to 100% of B vs D in 20 min]. The combined fractions were acidified with HCl and lyophilized to offer the compound (180 mg, 50%) as white solid. [(obs) $MH^+$=604.4, $M+Na^+$=626.5]

6.2. Example 2: Stability in Simulated Intestinal Fluid, Simulated Gastric Fluid, and Plasma|Permeability Experiments were conducted to assess the metabolic stability of test compounds in the simulated intestinal fluid (SIF), simulated gastric fluid (SGF), and plasma.
Plasma Stability Study
Assay Conditions
 [Compound]=1 μM
 Time=0, 60, 120, and 240 min
 Temperature=37° C.
Experimental Protocol
 Human and rat plasma (K2 EDTA) were obtained from Bioreclamation.

Compounds were dissolved as 0.3 mM DMSO stocks. Compounds were transferred to the plasma at 1 μM on a 96-well deep well plate. After mixing, samples were transferred to several 96-well plates (25 μL/well), and incubated at 37° C. The extent of metabolism was calculated as the disappearance of the test compound, compared to the 0-min control reaction incubations. Propantheline was included as a positive control to verify assay performance.

At each of the time points, 150 μL of quench solution (50% acetonitrile, 50% methanol with 0.05% formic acid) with internal standard (bucetin for positive ESI mode and warfarin for negative ESI mode) was transferred to each well. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed in the table below.

TABLE 1

| Gradient Conditions | | | |
|---|---|---|---|
| Time (min) | Flow (μL/min) | % A | % B |
| 0 | 500 | 98 | 2 |
| 0.30 | 500 | 98 | 2 |
| 1.40 | 500 | 2 | 98 |
| 2.00 | 500 | 2 | 98 |
| 2.01 | 500 | 98 | 2 |
| 2.50 | 500 | 98 | 2 |

Initial rates of the clearance of test compounds were calculated using linear regression of semi-log plot of % remaining of compounds versus time. The elimination rate constant (equals to −slope) of the linear regression was then used to determine t½ values.
Metabolic Stability in SIF and SGF (Simulated Intestinal and Gastric Fluid)
Assay Conditions
 [Drug]=5 μM
 Buffer 1=SGF without enzyme
 Buffer 2=SGF with 0.32% pepsin
 Buffer 3=SIF without enzyme
 Buffer 4=SIF with 1% pancreatin
 Time=0, 60, 120, and 240 min
 Temperature=37° C.
Experimental Protocol
 SIF was prepared freshly with 8.7 mM NaOH, 28.65 mM $NaH_2PO_4$, 105.85 mM NaCl, with a final pH of 6.8. SGF was prepared freshly with 34.2 mM NaCl, with a final pH of 1.2. Enzymes such as pepsin or pancreatin were added to some buffers. Human and rat plasma (K2 EDTA) were purchased from BioreclamationIVT.

Compounds were dissolved as 1.5 mM DMSO stocks. Compounds were transferred to SIF, SGF, or plasma at 5 μM on a 96-well deep well plate. After mixing, samples were transferred to several 96-well plates (25 μL/well), and incubated at 37° C. The extent of metabolism was calculated as the disappearance of the test compound, compared to the 0-min control reaction incubations. Candesartan Cilexetil and omeprazole were included as positive controls for SIF and SGF, respectively, to verify assay performance.

At each of the time points, 150 μL of quench solution (100% acetonitrile with 0.1% formic acid) with internal standard (bucetin for positive ESI mode and warfarin for negative ESI mode) was transferred to each well. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B). Elution conditions are detailed in the table below.

TABLE 1

Gradient Conditions

| Time (min) | Flow (µL/min) | % A | % B |
|---|---|---|---|
| 0 | 500 | 98 | 2 |
| 0.30 | 500 | 98 | 2 |
| 1.40 | 500 | 2 | 98 |
| 2.00 | 500 | 2 | 98 |
| 2.01 | 500 | 98 | 2 |
| 2.50 | 500 | 98 | 2 |

Initial rates of the clearance of test compounds were calculated using linear regression of semi-log plot of % remaining of compounds versus time. The elimination rate constant (equals to −slope) of the linear regression was then used to determine t½ values.

Permeability Study

Caco Experiment Methods

Assay Conditions

[Compound]=10 µM

[GF120918]=0 or 10 µM

Buffer=HBSS, pH 7.4 with 5 mM HEPES

Time=1 hr

Controls=Digoxin

Experimental Protocol

Caco-2 cell plates were obtained commercially and were maintained for 21 days at 37° C. with 5% CO2. Cells were washed with Hank's Balanced Salt Solution (HBSS) 30 min before starting the experiment. Test compound solutions were prepared by diluting from DMSO stock into HBSS buffer in the presence or absence of 10 µM of P-gp inhibitor GF120918. The final DMSO concentration is 0.2%. Prior to each experiment, cell monolayer integrity was verified by transendothelial electrical resistance (TEER). Transport experiment was initiated by adding test compounds to the apical (75 µL) side. Transport plates were incubated at 37° C. in a humidified incubator with 5% CO2. Samples were taken from the donor and acceptor compartments after 1 hr and analyzed by liquid chromatography with tandem mass spectrometry (LC/MS/MS).

Apparent permeability (Papp) values were calculated using the following equation:

$$Papp=(dQ/dt)/A/C_0$$

where dQ/dt is the initial rate of amount of test compound transported across cell monolayer, A is the surface area of the filter membrane, and $C_0$ is the initial concentration of the test compound. $C_0$ is calculated for each condition using a 4-point calibration curve. To calculate Papp each pro-drug and MM-201 were monitored simultaneously and the concentrations were added up to determine the final compound concentration in the system.

Absorption quotient between the two assay conditions was calculated by the following equation:

Absorption quotient (AQ)=(Papp, A-B with inhibitor−Papp, A-B without inhibitor)/Papp, A-B with inhibitor where Papp, A-B with inhibitor and Papp, A-B without inhibitor represent the apparent permeability of test compound from the apical to basal side of the cellular monolayer in the presence and absence of 10 µM P-gp inhibitor GF120918, respectively.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (10 mm×2.1 mm) at a flow rate of 0.5 mL/min. The mobile phase consisted of 0.1% formic acid in water (solvent A) and 0.1% formic acid in acetonitrile (solvent B).

TABLE 1

Gradient Conditions

| Time (min) | Flow (µL/min) | % A | % B |
|---|---|---|---|
| 0 | 500 | 98 | 2 |
| 0.30 | 500 | 98 | 2 |
| 1.40 | 500 | 2 | 98 |
| 2.00 | 500 | 2 | 98 |
| 2.01 | 500 | 98 | 2 |
| 2.50 | 500 | 98 | 2 |

6.3. Example 3: In-Vivo Pharmacokinetics

Methods and Materials:

1. Eight (8) male JVC SD rats (purchased from Charles River Lab) were monitored daily for body condition and health status during the 3-5 days acclimation period. The rats were randomly assigned into one group (n=4).

2. On Day 1,
   Rats are weighed and PO dosed with
   Group 1: 13.2 mg/kg of A20 (10 mL/kg of 1.32 mg/mL)
   Group 2: 14.2 mg/kg of A22 (10 mL/kg of 1.42 mg/mL).

3. The dosed rats were individually placed into a metabolic cage, and have access to food and water at all times. The urine from each rat was collected daily from the metabolic cages, and kept in dry ice.

4. At predose (0 min), 5 min, 15 min, 30 min, 1 hr, 2 hr, 8 hr, and 24 hr post dosing, approximately 200 ul blood samples were collected from each rat and transferred to EDTA tubes.

5. The blood samples in EDTA vials were centrifuged at 4° C. and 6,000 rpm for 10 minutes to generate ~100 µl of plasma per sample. Blood samples were processed as quickly as possible and remain no longer than 2 min at room temperature and no longer than 15 minutes at 4° C. prior to processing.

6. All samples were transferred for bioanalytic assay using LCMS

Data for each study are shown below:
| Compound ID | Structure |
|---|---|
| Base Structure | N-hexanoic-L-tyrosine-L-isoleucine-(6)-aminohexanoic amide |
| A26 | 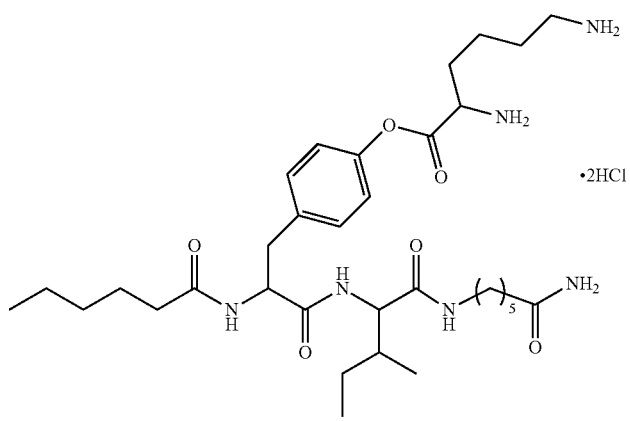 •2HCl |
| 2 | 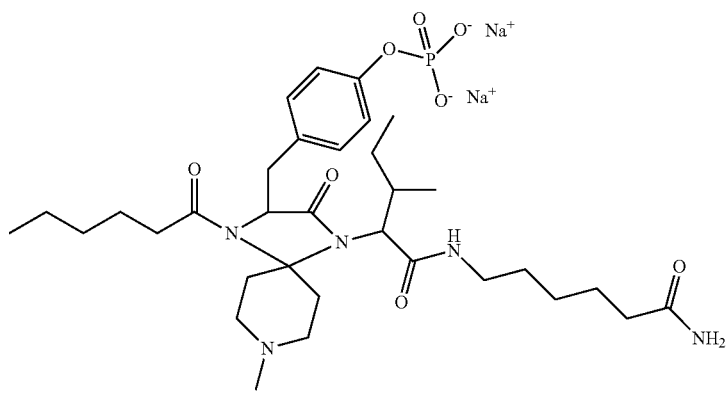 [SMILES: CCCCCC(=O)N1C(Cc2ccc(OP(=O)([O-])[O-])cc2)C(=O)N(C(C(=O)NCCCCCC(N)=O)C(C)CC)C12CCN(C)CC2 ; [Na+] ; [Na+]] |
| A28 | 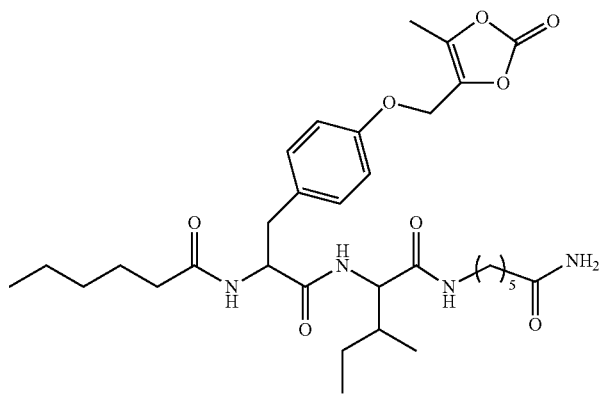 |

-continued
| Compound ID | Structure |
|---|---|
| A18 | 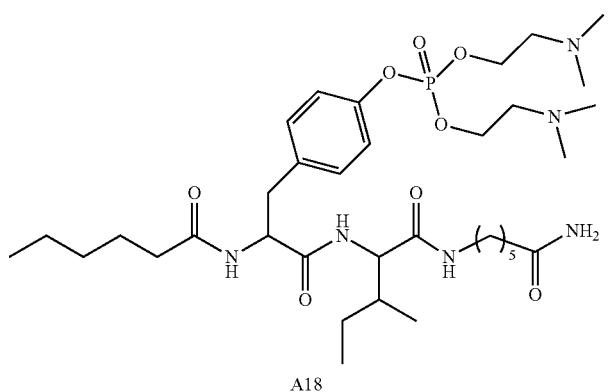<br>A18 |
| A29 | 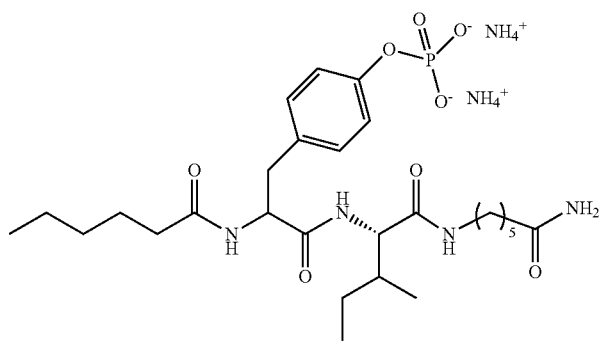 |
| A30 | 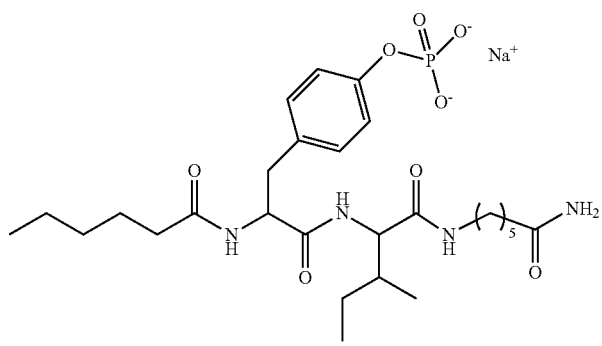 |
| A20 | 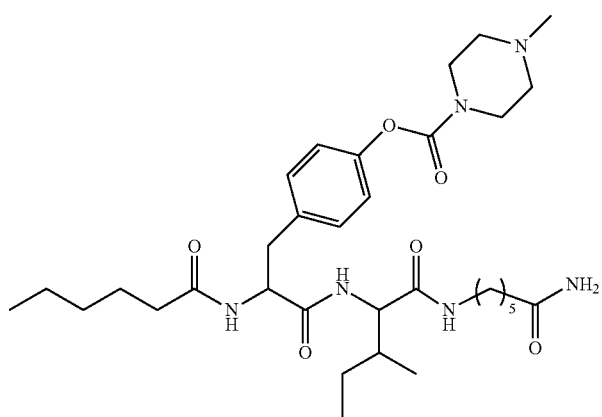 |

-continued
| Compound ID | Structure |
|---|---|
| A21 | 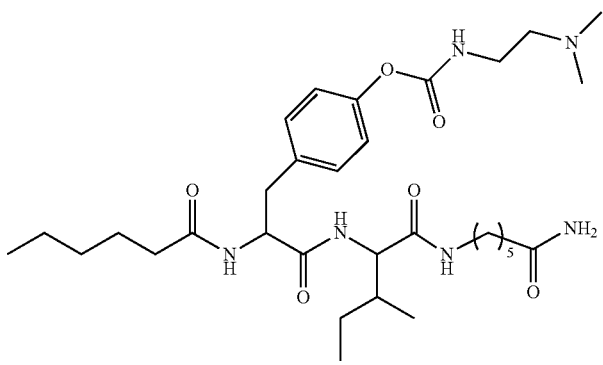 |
| A22 | 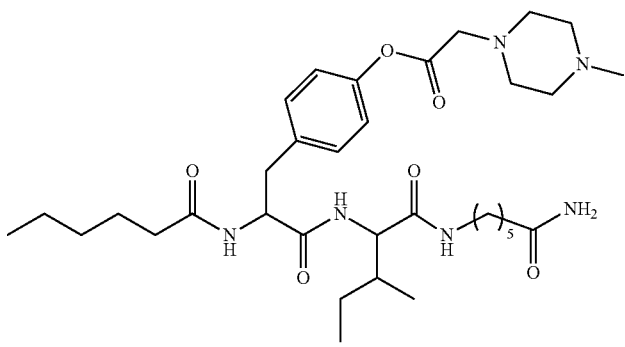 |
| A23 | 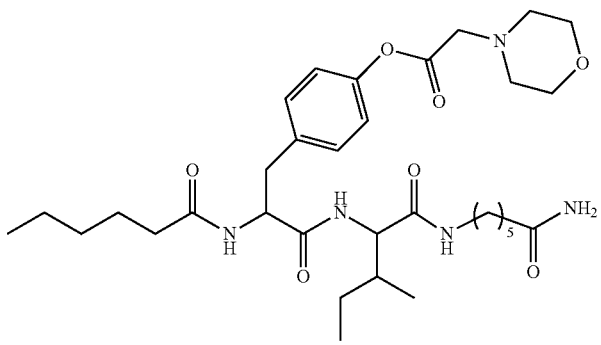 |
| A24 | 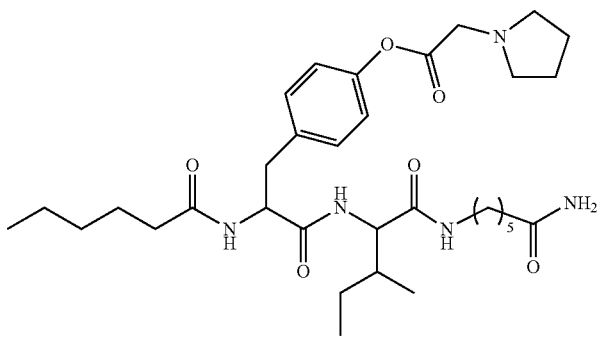 |

-continued

| Compound ID | Structure |
|---|---|
| A25 | 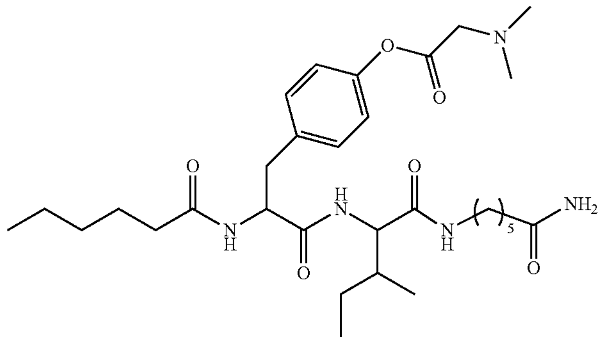 |
| A26 | 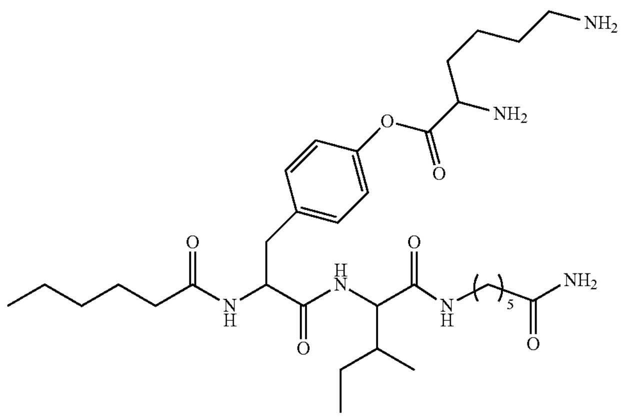 |
| A27 | 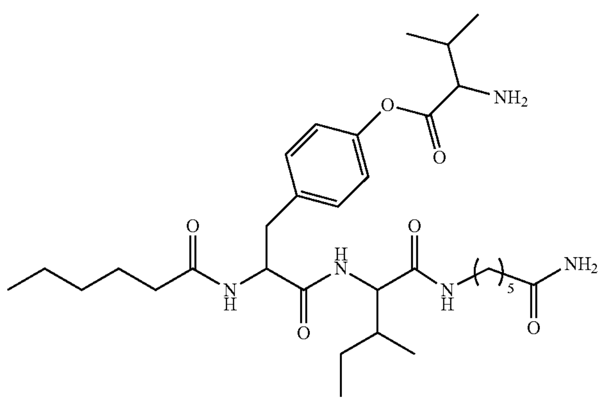 |

| | Plasma Stability (% Parent Remaining) | | | | | | | | |
|---|---|---|---|---|---|---|---|---|---|
| | Human Plasm | | | | | Rat Plasma | | | |
| Compound ID | 0 min | 60 min | 120 min | 240 min | Half-Life (min) | 0 min | 60 min | 120 min | 240 min | Half-Life (min) |
| Base Structure | 100% | 98% | 102% | 98% | 12558.0 | 100% | 87% | 89% | 83% | 1095.1 |
| A26 | 100% | 106% | 123% | 109% | NA | 100% | 112% | 117% | 111% | NA |
| 2 | 100% | 113% | 90% | 72% | 424.5 | 100% | 82% | 77% | 83% | 1083.6 |
| A28 | — | — | — | — | — | — | — | — | — | — |
| A18 | — | — | — | — | — | — | — | — | — | — |
| A29 | — | — | — | — | — | — | — | — | — | — |
| A30 | 100% | 36% | 20% | 12% | 84.2 | 100% | 88% | 87% | 86% | 1307.4 |

-continued

| | Plasma Stability (% Parent Remaining) | | | | | | | | | |
|---|---|---|---|---|---|---|---|---|---|---|
| | Human Plasm | | | | | Rat Plasma | | | | |
| Compound ID | 0 min | 60 min | 120 min | 240 min | Half-Life (min) | 0 min | 60 min | 120 min | 240 min | Half-Life (min) |
| A20 | 100% | 83% | 87% | 90% | 2957.7 | 100% | 73% | 56% | 34% | 157.0 |
| A21 | 100% | 59% | 33% | 11% | 73.4 | 100% | 61% | 34% | 9% | 69.7 |
| A22 | 100% | 59% | 37% | 15% | 87.9 | 100% | 1% | 0% | 0% | 8.7 |
| A23 | 100% | 29% | 7% | 1% | 31.3 | 100% | 1% | 1% | 0% | 8.2 |
| A24 | 100% | 0% | 0% | 0% | 7.3 | 100% | 55% | 27% | 47% | 64.2 |
| A25 | 100% | 2% | 0% | 0% | 10.1 | 100% | 1% | 0% | 0% | 8.2 |
| A26 | 100% | 11% | 7% | 13% | 18.8 | 100% | 5% | 10% | 8% | 13.5 |
| A27 | 100% | 4% | 4% | 5% | 13.2 | 100% | 27% | 29% | 37% | 31.9 |

| | SIF Stability (pH 6.8) | | | | | | | | | |
|---|---|---|---|---|---|---|---|---|---|---|
| | −Pancreatin | | | | | +Pancreatin | | | | |
| Compound ID | 0 min | 60 min | 120 min | 240 min | Half-Life (min) | 0 min | 60 min | 120 min | 240 min | Half-Life (min) |
| BASE STRUCTURE | 100% | 119% | — | 113% | Neg. | — | — | — | — | — |
| A26 | Not in report | Not in report | Not in report | Not in report | Not in report | Not in report | Not in report | Not in report | Not in report | Not in report |
| 2 | 100% | 82% | 82% | 78% | 801.5 | 100% | 94% | 51% | 34% | 142.4 |
| A28 | | | | | | | | | | |
| A18 | 100% | 25% | 17% | 8% | 30.2 | 100% | 40% | 12% | 25% | 39.4 |
| A29 | 100% | 96% | 97% | 103% | Neg. | 100% | 94% | 98% | 104% | Neg. |
| A30 | 100% | 43% | 22% | 8% | 68.4 | 100% | 70% | 51% | 34% | 156.6 |
| A20 | 100% | 65% | 57% | 51% | 95.4 | 100% | 62% | 54% | 61% | 86.6 |
| A21 | — | — | — | — | — | 100% | 95% | 97% | 93% | 3006.4 |
| A22 | 100% | 74% | 61% | 59% | 335.8 | 100% | 69% | 64% | 63% | 425.9 |
| A23 | 100% | 93% | 95% | 79% | 744.0 | 100% | 66% | 41% | 20% | 104.5 |
| A24 | 100% | 62% | 38% | 14% | 83.5 | 100% | 13% | 1% | 0% | 18.8 |
| A25 | — | — | — | — | — | 100% | 27% | 7% | 1% | 34.7 |
| A26 | 100% | 11% | 1% | 0% | 19.6 | 100% | 78% | 52% | 37% | 166.9 |
| A27 | 100% | 63% | 59% | 24% | 122.6 | 100% | 49% | 24% | 5% | 57.1 |

| | SGF Stability (pH 1.2) | | | | | | | | | |
|---|---|---|---|---|---|---|---|---|---|---|
| | −Pepsin | | | | | +Pepsin | | | | |
| Compound ID | 0 min | 60 min | 120 min | 240 min | Half-Life (min) | 0 min | 60 min | 120 min | 240 min | Half-Life (min) |
| BASE STRUCTURE | 100% | 127% | — | 122% | Neg. | 100% | 13% | — | 0.2% | 26.0 |
| A26 | Not in report | Not in report | Not in report | Not in report | Not in report | Not in report | Not in report | Not in report | Not in report | Not in report |
| 2 | 100% | 84% | 78% | 67% | 430.2 | 100% | 94% | 89% | 73% | 517.4 |
| A28 | — | — | — | — | — | — | — | — | — | — |
| A18 | 100% | 51% | 14% | 15% | 42.6 | 100% | 52% | 17% | 18% | 46.4 |
| A29 | 100% | 117% | 129% | 123% | Neg. | 100% | 86% | 63% | 49% | 225.0 |
| A30 | 100% | 95% | 98% | 89% | 1713.6 | 100% | 95% | 64% | 54% | 248.3 |
| A20 | 100% | 70% | 57% | 60% | 116.5 | 100% | 57% | 37% | 26% | 84.5 |
| A21 | — | — | — | — | — | 100% | 87% | 74% | 54% | 265.1 |
| A22 | 100% | 70% | 51% | 55% | 124.5 | 100% | 52% | 26% | 10% | 73.5 |
| A23 | 100% | 92% | 85% | 83% | 892.2 | 100% | 79% | 65% | 45% | 211.0 |
| A24 | 100% | 97% | 89% | 84% | 916.4 | 100% | 74% | 61% | 43% | 201.9 |
| A25 | — | — | — | — | — | 100% | 94% | 91% | 65% | 389.4 |
| A26 | 100% | 63% | 33% | 115% | 75.9 | 100% | 88% | 36% | 120% | 80.3 |
| A27 | 100% | 115% | 107% | 105% | Neg. | 100% | 102% | 95% | 71% | 449.7 |

| | Caco-2 Cells Permeability | | | | |
|---|---|---|---|---|---|
| | −GF120918 | | +GF120918 | | |
| Compound ID | $P_{app\,A\text{-}B}$ | Recovery Rate | $P_{app\,A\text{-}B}$ | Recovery Rate | Abs. Quotient |
| BASE STRUCTURE | 0.064 | 87% | 0.41 | 83% | 0.84 |
| A26 | 0.1 | 91% | 0.5 | 96% | 0.82 |
| 2 | — | — | — | — | — |
| A28 | — | — | — | — | — |
| A18 | 0.04 | 48% | 0.08 | 90% | 0.54 |
| A29 | 0.028 | 86% | 0.17 | 76% | 0.83 |
| A30 | — | — | — | — | — |
| A20 | 0.06 | 71% | 0.5 | 90% | 0.88 |
| A21 | 0.099 | 84% | 0.2 | 84% | 0.50 |
| A22 | 0.1 | 107% | 0.7 | 104% | 0.78 |
| A23 | 0.1 | 91% | 0.4 | 96% | 0.78 |
| A24 | 0.1 | 72% | 0.6 | 72% | 0.88 |
| A25 | 0.092 | 91% | 0.4 | 83% | 0.77 |
| A26 | 0.044 | 94% | 0.29 | 89% | 0.85 |
| A27 | 0.117 | 90% | 0.39 | 94% | 0.70 |

| | Rat PK (PO Route, 10 mg/kg Equiv., n = 4) Parent (BASE STRUCTURE) | | | | |
|---|---|---|---|---|---|
| Compound ID | "$AUC_{0\text{-}24}$ (ng · h/mL)" | "$AUC_{0\text{-}inf}$ (ng · h/mL)" | "Cmax (ng/mL)" | "Tmax (h)" | "Half-Life (h)" |
| BASE STRUCTURE | 0.4 ± 0.2 | — | 0.9 ± 0.5 | 0.4 ± 0.5 | — |
| A26 | — | — | — | — | — |
| 2 | — | — | — | — | — |
| A28 | — | — | — | — | — |
| A18 | 4.1 ± 3.8 | 6.8 ± 4 | 3.1 ± 2.5 | 0.2 ± 0.1 | 3.5 ± 2.6 |
| A29 | 35.9 ± 27.6 | 48.6 ± 26.5 | 39.7 ± 74.2 | 2.1 ± 4 | 15.7 ± 14.3 |
| A30 | | | | | |
| A20 | 0.8 ± 1 | 1.61 | 1.7 ± 1.3 | 0.3 ± 0 | 0.17 |
| A21 | 7.4 ± 0.9 | 47.8 ± 1 | 0.6 ± 0.1 | 0.9 ± 0.8 | 81.7 ± 5.7 |
| A22 | 25.1 ± 4.4 | 91.3 | 1.4 ± 0.1 | 15 ± 10.5 | 58.8 |
| A23 | 5.1 ± 1.4 | 12.4 ± 8.8 | 5.5 ± 6.2 | 0.2 ± 0.2 | 22.1 ± 17.1 |
| A24 | 0.4 ± 0.2 | 1.1 ± 0.9 | 0.3 ± 0.1 | 0.4 ± 0.4 | 5 ± 5.1 |
| A25 | 10.9 ± 4 | 31 ± 26.1 | 3.1 ± 3.5 | 0.3 ± 0.2 | 42.5 ± 49.9 |
| A26 | 14.1 ± 6.3 | 28 ± 12 | 6.8 ± 6.6 | 1.1 ± 1.9 | 8.9 ± 0.5 |
| A27 | 29.6 ± 35 | 9.0 | 2.8 ± 2.7 | 18.1 ± 11.8 | 13.4 |

| | Rat PK (PO Route, 10 mg/kg Equiv., n = 4) Prodrug | | | | |
|---|---|---|---|---|---|
| Compound ID | "AUC0-24 (ng · h/mL)" | "AUC0-inf (ng · h/mL)" | "Cmax (ng/mL)" | "Tmax (h)" | "Half-Life (h)" |
| BASE STRUCTURE | — | — | — | — | — |
| A26 | — | — | — | — | — |
| 2 | — | — | — | — | — |
| A28 | — | — | — | — | — |
| A18 | 4.9 ± 2.6 | — | 3.8 ± 0.1 | 1.5 ± 0.7 | — |
| A29 | 0 | 0 | 0 | 0 | 0 |
| A30 | | | | | |
| A20 | 0 | 0 | 0 | 0 | 0 |
| A21 | 2.8 ± 1.9 | 6.46 | 1.6 ± 0.5 | 0.8 ± 0.4 | 1.32 |
| A22 | 0 | 0 | 0 | 0 | 0 |
| A23 | 0 | 0 | 0 | 0 | 0 |
| A24 | 0.2 ± 0.1 | — | 0.5 ± 0.1 | 0.9 ± 0.3 | — |
| A25 | 91.2 ± 3.8 | 3709.5 | 4.2 ± 0.1 | 9.3 ± 10.2 | 667.8 |
| A26 | 0 | 0 | 0 | 0 | 0 |
| A27 | 0 | 0 | 0 | 0 | 0 |

| BASE STRUCTURE (20 mg/kg) | | | | | | | | |
|---|---|---|---|---|---|---|---|---|
| Parameter | Unit | Animal 1 | Animal 2 | Animal 3 | Animal 4 | Average | Std. Dev. | Combined |
| Dosed as Parent (Base Structure) | | | | | | | | |
| Lambda_z | 1/h | | | | | | | |
| t1/2 | h | | | | | | | |
| Tmax | h | 0.08 | 0.25 | 1 | | 0.4433333 | 0.4895236 | 0.4 ± 0.5 |
| Cmax | ng/ml | 0.689 | 1.54 | 0.551 | | 0.9266667 | 0.5356252 | 0.9 ± 0.5 |
| Tlag | h | 0 | 0 | 0 | | 0 | 0 | 0 ± 0 |
| Clast_obs/Cmax | | 0.8577649 | 0.6 | 1 | | 0.819255 | 0.2027616 | 0.8 ± 0.2 |
| AUC 0-t | ng/ml * h | 0.61636 | 0.517525 | 0.206625 | | 0.4468367 | 0.2138184 | 0.4 ± 0.2 |
| AUC 0-inf_obs | ng/ml * h | | | | | | | |
| AUC 0-t/0-inf_obs | | | | | | | | |
| AUMC 0-inf_obs | ng/ml * h^2 | | | | | | | |
| MRT 0-inf_obs | h | | | | | | | |
| Vz/F_obs | (mg/kg)/(ng/ml) | | | | | | | |
| Cl/F_obs | (mg/kg)/(ng/ml)/h | | | | | | | |
| Dosed as A18 (10 mg/kg equivalent of Base Structure) Parameters for Parent (Base Structure) following dosing of A18 | | | | | | | | |
| Lambda_Z | 1/h | 0.3302821 | 1.5184227 | 0.123071 | 0.1201033 | 0.5229698 | 0.6708888 | 0.5 ± 0.7 |
| t1/2 | h | 2.0986519 | 0.4564916 | 5.6320917 | 5.7712605 | 3.4896239 | 2.641384 | 3.5 ± 2.6 |
| Tmax | h | 0.25 | 0.08 | 0.08 | 0.25 | 0.165 | 0.0981495 | 0.2 ± 0.1 |
| Cmax | ng/ml | 1.3 | 3.37 | 1.27 | 6.62 | 3.14 | 2.5196428 | 3.1 ± 2.5 |
| Tlag | h | 0 | 0 | 0 | 0 | 0 | 0 | 0 ± 0 |
| Clast_obs/Cmax | | 0.4638462 | 0.0836795 | 0.7102362 | 0.026284 | 0.3210115 | 0.3240825 | 0.3 ± 0.3 |
| AUC 0-t | ng/ml * h | 1.663875 | 3.218 | 1.90263 | 9.77745 | 4.1404888 | 3.8195962 | 4.1 ± 3.8 |
| AUC 0-inf_obs | ng/ml * h | 3.4895869 | 3.403719 | 9.2317325 | 11.226203 | 6.8378105 | 3.999685 | 6.8 ± 4 |
| AUC 0-t/0-inf_obs | | 0.4768114 | 0.9454364 | 0.2060967 | 0.8709489 | 0.6248234 | 0.3467035 | 0.6 ± 0.3 |
| AUMC 0-inf_obs | ng/ml * h^2 | 10.678131 | 2.5861986 | 76.049072 | 97.479622 | 46.698256 | 47.200073 | 46.7 ± 47.2 |

-continued

| | BASE STRUCTURE (20 mg/kg) | | | | | | | |
|---|---|---|---|---|---|---|---|---|
| | Parameter | Unit | Animal 1 | Animal 2 | Animal 3 | Animal 4 | Average | Std. Dev. | Combined |
| 48 | MRT 0-inf_obs | h | 3.0599986 | 0.7598155 | 8.2377898 | 8.6832225 | 5.1852066 | 3.9010672 | 5.2 ± 3.9 |
| 49 | Vz/F_obs | (mg/kg)/(ng/ml) | 8.6764271 | 1.9348781 | 8.8015882 | 7.4167273 | 6.7074052 | 3.2425711 | 6.7 ± 3.2 |
| 50 | Cl/F_obs | (mg/kg)/(ng/ml)/h | 2.8656687 | 2.9379628 | 1.0832203 | 0.8907731 | 1.9444062 | 1.1087024 | 1.9 ± 1.1 |
| | Data for Prodrug A18 | | | | | | | | |
| 54 | Lambda_z | 1/h | — | — | | | | | |
| 55 | t1/2 | h | — | — | | | | | |
| 56 | Tmax | h | 2 | 1 | | | 1.5 | 0.7071068 | 1.5 ± 0.7 |
| 57 | Cmax | ng/ml | 3.84 | 3.68 | | | 3.76 | 0.1131371 | 3.8 ± 0.1 |
| 58 | Tlag | h | 0 | 0 | | | 0 | 0 | 0 ± 0 |
| 59 | Clast_obs/Cmax | | 1 | 1 | | | 1 | 0 | 1 ± 0 |
| 60 | AUC 0-t | ng/ml * h | 6.8 | 3.09875 | | | 4.949375 | 2.617179 | 4.9 ± 2.6 |
| 61 | AUC 0-inf_obs | ng/ml * h | — | — | | | | | |
| 62 | AUC 0-t/0-inf_obs | | — | — | | | | | |
| 63 | AUMC 0-inf_obs | ng/ml * h^2 | — | — | | | | | |
| 64 | MRT 0-inf_obs | h | — | — | | | | | |
| 65 | Vz/F_obs | (mg/kg)/(ng/ml) | — | — | | | | | |
| 66 | Cl/F_obs | (mg/kg)/(ng/ml)/h | — | — | | | | | |
| | Sample dosed as 2 (10 mg/kg, equivalent of Base Structure) Parameters for Parent (Base Structure) following dosing of 2 | | | | | | | | |
| 71 | Lambda_Z | 1/h | 0.1912491 | 0.0584922 | 0.0219906 | | 0.0905773 | 0.0890741 | 0.1 ± 0.1 |
| 72 | t1/2 | h | 3.6243165 | 11.85024 | 31.520108 | | 15.664888 | 14.333787 | 15.7 ± 14.3 |
| 73 | Tmax | h | 0.08 | 0.08 | 0.08 | 8 | 2.06 | 3.96 | 2.1 ± 4 |
| 74 | Cmax | ng/ml | 151 | 4.73 | 1.36 | 1.65 | 39.685 | 74.225665 | 39.7 ± 74.2 |
| 75 | Tlag | h | 0 | 0 | 0 | 0 | 0 | 0 | 0 ± 0 |
| 76 | Clast_obs/Cmax | | 0.0042848 | 0.0501057 | 0.3117647 | 0.3369697 | 0.1757812 | 0.1728955 | 0.2 ± 0.2 |
| 77 | AUC 0-t | ng/ml * h | 75.7995 | 30.4074 | 12.9897 | 24.48944 | 35.92151 | 27.551283 | 35.9 ± 27.6 |
| 78 | AUC 0-inf_obs | ng/ml * h | 79.182523 | 34.459219 | 32.270635 | | 48.637459 | 26.475426 | 48.6 ± 26.5 |
| 79 | AUC 0-t/0-inf_obs | | 0.9572756 | 0.882217 | 0.4025238 | | 0.7474055 | 0.3010124 | 0.7 ± 0.3 |
| 80 | AUMC 0-inf_obs | ng/ml * h^2 | 284.76414 | 414.61785 | 1486.3623 | | 728.58144 | 659.46145 | 728.6 ± 659.5 |
| 81 | MRT 0-inf_obs | h | 3.5963005 | 12.032131 | 46.059284 | | 20.562572 | 22.480048 | 20.6 ± 22.5 |
| 82 | Vz/F_obs | (mg/kg)/(ng/ml) | 0.6603457 | 4.9613088 | 14.091419 | | 6.5710244 | 6.8587039 | 6.6 ± 6.9 |
| 83 | Cl/F_obs | (mg/kg)/(ng/ml)/h | 0.1262905 | 0.2901981 | 0.3098792 | | 0.2421226 | 0.1007951 | 0.2 ± 0.1 |
| | Data for Prodrug 2 | | | | | | | | |
| 87 | Lambda_z | 1/h | 0 | | | | 0 | | 0 |
| 88 | t1/2 | h | 0 | | | | 0 | | 0 |
| 89 | Tmax | h | 0 | | | | 0 | | 0 |
| 90 | Cmax | ng/ml | 0 | | | | 0 | | 0 |
| 91 | Tlag | h | 0 | | | | 0 | | 0 |
| 92 | Clast_obs/Cmax | | 0 | | | | 0 | | 0 |
| 93 | AUC 0-t | ng/ml * h | 0 | | | | 0 | | 0 |
| 94 | AUC 0-inf_obs | ng/ml * h | 0 | | | | 0 | | 0 |
| 95 | AUC 0-t/0-inf_obs | | 0 | | | | 0 | | 0 |

-continued

| | BASE STRUCTURE (20 mg/kg) | | | | | | | | |
|---|---|---|---|---|---|---|---|---|---|
| | Parameter | Unit | Animal 1 | Animal 2 | Animal 3 | Animal 4 | Average | Std. Dev. | Combined |
| 96 | AUMC 0-inf_obs | ng/ml * h^2 | 0 | | | | 0 | | 0 |
| 97 | MRT 0-inf_obs | h | 0 | | | | 0 | | 0 |
| 98 | Vz/F_obs | (mg/kg)/(ng/ml) | 0 | | | | 0 | | 0 |
| 99 | Cl/F_obs | (mg/kg)/(ng/ml)/h | 0 | | | | 0 | | 0 |
| | Dosed as A20 (10 mg/kg, equivalent of Base Structure) Parameters for Parent (Base Structure) following dosing of A20 | | | | | | | | |
| 104 | Lambda_Z | 1/h | — | | | 4.0218636 | 4.0218636 | | 4.021864 |
| 105 | t1/2 | h | — | | | 0.1723448 | 0.1723448 | | 0.172345 |
| 106 | Tmax | h | 0.25 | | | 0.25 | 0.25 | 0 | 0.3 ± 0 |
| 107 | Cmax | ng/ml | 0.765 | | | 2.66 | 1.7125 | 1.3399674 | 1.7 ± 1.3 |
| 108 | Tlag | h | 0 | | | 0 | 0 | 0 | 0 ± 0 |
| 109 | Clast_obs/Cmax | | 1 | | | 0.0582707 | 0.5291353 | 0.6659032 | 0.5 ± 0.7 |
| 110 | AUC 0-t | ng/ml * h | 0.089275 | | | 1.5726 | 0.8309375 | 1.0488692 | 0.8 ± 1 |
| 111 | AUC 0-inf_obs | ng/ml * h | — | | | 1.6111393 | 1.6111393 | | 1.611139 |
| 112 | AUC 0-t/0-inf_obs | | — | | | 0.9760794 | 0.9760794 | | 0.976079 |
| 113 | AUMC 0-inf_obs | ng/ml * h^2 | — | | | 0.6699418 | 0.6699418 | | 0.669942 |
| 114 | MRT 0-inf_obs | h | — | | | 0.4158187 | 0.4158187 | | 0.415819 |
| 115 | Vz/F_obs | (mg/kg)/(ng/ml) | — | | | 1.5432616 | 1.5432616 | | 1.543262 |
| 116 | Cl/F_obs | (mg/kg)/(ng/ml)/h | — | | | 6.2067878 | 6.2067878 | | 6.206787 |
| | Data for Prodrug A20 | | | | | | | | |
| 120 | Lambda_z | 1/h | 0 | | | | 0 | | 0 |
| 121 | t1/2 | h | 0 | | | | 0 | | 0 |
| 122 | Tmax | h | 0 | | | | 0 | | 0 |
| 123 | Cmax | ng/ml | 0 | | | | 0 | | 0 |
| 124 | Tlag | h | 0 | | | | 0 | | 0 |
| 125 | Clast_obs/Cmax | | 0 | | | | 0 | | 0 |
| 126 | AUC 0-t | ng/ml * h | 0 | | | | 0 | | 0 |
| 127 | AUC 0-inf_obs | ng/ml * h | 0 | | | | 0 | | 0 |
| 128 | AUC 0-t/0-inf_obs | | 0 | | | | 0 | | 0 |
| 129 | AUMC 0-inf_obs | ng/ml * h^2 | 0 | | | | 0 | | 0 |
| 130 | MRT 0-inf_obs | h | 0 | | | | 0 | | 0 |
| 131 | Vz/F_obs | (mg/kg)/(ng/ml) | 0 | | | | 0 | | 0 |
| 132 | Cl/F_obs | (mg/kg)/(ng/ml)/h | 0 | | | | 0 | | 0 |
| | Dosed as A21 (10 mg/kg, equivalent of Base Structure) Parameters for Parent (Base Structure) following dosing of A21 | | | | | | | | |
| 137 | Lambda_z | 1/h | 0.0080896 | 0.0089246 | | | 0.0085071 | 0.0005904 | 0 ± 0 |
| 138 | t1/2 | h | 85.683945 | 77.667256 | | | 81.6756 | 5.6686552 | 81.7 ± 5.7 |
| 139 | Tmax | h | 0.25 | 0.25 | 1 | 2 | 0.875 | 0.8291562 | 0.9 ± 0.8 |
| 140 | Cmax | ng/ml | 0.744 | 0.604 | 0.555 | 0.577 | 0.62 | 0.0850608 | 0.6 ± 0.1 |

-continued

| | BASE STRUCTURE (20 mg/kg) | | | | | | | | |
|---|---|---|---|---|---|---|---|---|---|
| | Parameter | Unit | Animal 1 | Animal 2 | Animal 3 | Animal 4 | Average | Std. Dev. | Combined |
| 141 | Tlag | h | 0 | 0 | 0 | 0 | 0 | 0 | 0 ± 0 |
| 142 | Clast_obs/Cmax | | 0.4475806 | 0.5745033 | 0.8630631 | 0.9341421 | 0.7048223 | 0.2315052 | 0.7 ± 0.2 |
| 143 | AUC 0-t | ng/ml * h | 7.284615 | 8.224465 | 6.27042 | 8.02234 | 7.44996 | 0.8837489 | 7.4 ± 0.9 |
| 144 | AUC 0-inf_obs | ng/ml * h | 48.448677 | 47.103872 | — | — | 47.776275 | 0.9509207 | 47.8 ± 1 |
| 145 | AUC 0-t/0-inf_obs | | 0.1503574 | 0.1745603 | — | — | 0.1624588 | 0.017114 | 0.2 ± 0 |
| 146 | AUMC 0-inf_obs | ng/ml * h^2 | 6167.4557 | 5387.4053 | — | — | 5777.4305 | 551.5789 | 5777.4 ± 551.6 |
| 147 | MRT 0-inf_obs | h | 127.29874 | 114.37288 | — | — | 120.83581 | 9.139968 | 120.8 ± 9.1 |
| 148 | Vz/F_obs | (mg/kg)/(ng/ml) | 25.514794 | 23.787888 | — | — | 24.651341 | 1.2211068 | 24.7 ± 1.2 |
| 149 | Cl/F_obs | (mg/kg)/(ng/ml)/h | 0.206404 | 0.2122968 | — | — | 0.2093504 | 0.0041668 | 0.2 ± 0 |
| | Data for Prodrug A21 | | | | | | | | |
| 153 | Lambda_Z | 1/h | 0.5256781 | | | | 0.5256781 | | 0.525678 |
| 154 | t1/2 | h | 1.3185771 | | | | 1.3185771 | | 1.318577 |
| 155 | Tmax | h | 0.25 | 1 | 1 | 1 | 0.8125 | 0.375 | 0.8 ± 0.4 |
| 156 | Cmax | ng/ml | 2.18 | 1.89 | 1.01 | 1.38 | 1.615 | 0.5215681 | 1.6 ± 0.5 |
| 157 | Tlag | h | 0 | 0 | 0 | 0 | 0 | 0 | 0 ± 0 |
| 158 | Clast_obs/Cmax | | 0.2027523 | 0.6296296 | 0.6049505 | 0.5862319 | 0.5058911 | 0.2028725 | 0.5 ± 0.2 |
| 159 | AUC 0-t | ng/ml * h | 5.61855 | 2.381305 | 1.497735 | 1.885 | 2.8456475 | 1.8836413 | 2.8 ± 1.9 |
| 160 | AUC 0-inf_obs | ng/ml * h | 6.4593687 | | | | 6.4593687 | | 6.459369 |
| 161 | AUC 0-t/0-inf_obs | | 0.8698296 | | | | 0.8698296 | | 0.86983 |
| 162 | AUMC 0-inf_obs | ng/ml * h^2 | 13.688243 | | | | 13.688243 | | 13.68824 |
| 163 | MRT 0-inf_obs | h | 2.1191302 | | | | 2.1191302 | | 2.11913 |
| 164 | Vz/F_obs | (mg/kg)/(ng/ml) | 2.9450319 | | | | 2.9450319 | | 2.945032 |
| 165 | Cl/F_obs | (mg/kg)/(ng/ml)/h | 1.5481389 | | | | 1.5481389 | | 1.5481389 |
| | Dosed as A22 (10 mg/kg, equivalent of Base Structure) Parameters for Parent (Base Structure) following dosing of A22 | | | | | | | | |
| 170 | Lambda_z | 1/h | — | 0.0117847 | — | — | 0.0117847 | | 0.011785 |
| 171 | t1/2 | h | — | 58.817694 | — | — | 58.817694 | | 58.81769 |
| 172 | Tmax | h | 24 | 4 | 24 | 8 | 15 | 10.519823 | 15 ± 10.5 |
| 173 | Cmax | ng/ml | 1.51 | 1.32 | 1.35 | 1.55 | 1.4325 | 0.1144188 | 1.4 ± 0.1 |
| 174 | Tlag | h | 0 | 0 | 0 | 0 | 0 | 0 | 0 ± 0 |
| 175 | Clast_obs/Cmax | | 1 | 0.6477273 | 1 | 0.4251613 | 0.7682221 | 0.2826374 | 0.8 ± 0.3 |
| 176 | AUC 0-t | ng/ml * h | 28.915155 | 18.755375 | 26.459875 | 26.3888 | 25.129801 | 4.408945 | 25.1 ± 4.4 |
| 177 | AUC 0-inf_obs | ng/ml * h | — | 91.307251 | — | — | 91.307251 | | 91.30725 |
| 178 | AUC 0-t/0-inf_obs | | — | 0.2054095 | — | — | 0.2054095 | | 0.205409 |
| 179 | AUMC 0-inf_obs | ng/ml * h^2 | — | 8134.3242 | — | — | 8134.3242 | | 8134.324 |
| 180 | MRT 0-inf_obs | h | — | 89.087384 | — | — | 89.087384 | | 89.08738 |
| 181 | Vz/F_obs | (mg/kg)/(ng/ml) | — | 9.2934564 | — | — | 9.2934564 | | 9.293456 |
| 182 | Cl/F_obs | (mg/kg)/(ng/ml)/h | — | 0.1095203 | — | — | 0.1095203 | | 0.1095203 |
| 186 | Lambda_z | 1/h | 0 | | | | 0 | | 0 |
| 187 | t1/2 | h | 0 | | | | 0 | | 0 |
| 188 | Tmax | h | 0 | | | | 0 | | 0 |

-continued

| BASE STRUCTURE (20 mg/kg) | | | | | | | | |
|---|---|---|---|---|---|---|---|---|
| | Parameter | Unit | Animal 1 | Animal 2 | Animal 3 | Animal 4 | Average | Std. Dev. | Combined |
| 189 | Cmax | ng/ml | 0 | | | | 0 | | 0 ± 0 |
| 190 | Tlag | h | 0 | | | | 0 | | 0 |
| 191 | Clast_obs/Cmax | | 0 | | | | 0 | | 0 |
| 192 | AUC 0-t | ng/ml * h | 0 | | | | 0 | | 0 |
| 193 | AUC 0-inf_obs | ng/ml * h | 0 | | | | 0 | | 0 |
| 194 | AUC 0-t/0-inf_obs | | 0 | | | | 0 | | 0 |
| 195 | AUMC 0-inf_obs | ng/ml * h^2 | 0 | | | | 0 | | 0 |
| 196 | MRT 0-inf_obs | h | 0 | | | | 0 | | 0 |
| 197 | Vz/F_obs | (mg/kg)/(ng/ml) | 0 | | | | 0 | | 0 |
| 198 | Cl/F_obs | (mg/kg)/(ng/ml)/h | 0 | | | | 0 | | 0 |
| | Dosed as A23 (10 mg/kg, equivalent of Base Structure) Parameters for Parent (Base Structure) following dosing of A23 | | | | | | | | |
| 203 | Lambda_z | 1/h | 0.0435952 | 0.0738764 | 0.0440852 | 0.014645 | 0.0440505 | 0.0241832 | |
| 204 | t1/2 | h | 15.899634 | 9.3825196 | 15.722913 | 47.329796 | 22.083715 | 17.101536 | 22.1 ± 17.1 |
| 205 | Tmax | h | 0.08 | 0.5 | 0.08 | 0.25 | 0.2275 | 0.1985573 | 0.2 ± 0.2 |
| 206 | Cmax | ng/ml | 2.51 | 3.48 | 14.6 | 1.28 | 5.4675 | 6.1545288 | 5.5 ± 6.2 |
| 207 | Tlag | h | 0 | 0 | 0 | 0 | 0 | 0 | 0 ± 0 |
| 208 | Clast_obs/Cmax | | 0.0454183 | 0.0321839 | 0.0165753 | 0.2234375 | 0.0794038 | 0.0967434 | 0.1 ± 0.1 |
| 209 | AUC 0-t | ng/ml * h | 3.56898 | 4.61648 | 6.95044 | 5.29615 | 5.1080125 | 1.4189386 | 5.1 ± 1.4 |
| 210 | AUC 0-inf_obs | ng/ml * h | 6.1839488 | 6.1325248 | 12.439815 | 24.824934 | 12.395306 | 8.7996405 | 12.4 ± 8.8 |
| 211 | AUC 0-t/0-inf_obs | | 0.5771361 | 0.7527862 | 0.5587253 | 0.2133399 | 0.5254969 | 0.2257381 | 0.5 ± 0.2 |
| 212 | AUMC 0-inf_obs | ng/ml * h^2 | 156.19016 | 90.340465 | 316.30901 | 1873.3254 | 609.04125 | 848.18063 | 609 ± 848.2 |
| 213 | MRT 0-inf_obs | h | 25.257349 | 14.731366 | 25.427147 | 75.461445 | 35.219327 | 27.290489 | 35.2 ± 27.3 |
| 214 | Vz/F_obs | (mg/kg)/(ng/ml) | 37.093326 | 22.072662 | 18.23449 | 27.505596 | 26.226518 | 8.1823099 | 26.2 ± 8.2 |
| 215 | Cl/F_obs | (mg/kg)/(ng/ml)/h | 1.6170897 | 1.6306497 | 0.8038705 | 0.4028208 | 1.1136077 | 0.6115504 | 1.1 ± 0.6 |
| | Data for Prodrug A23 | | | | | | | | |
| 219 | Lambda_z | 1/h | 0 | | | | 0 | | 0 |
| 220 | t1/2 | h | 0 | | | | 0 | | 0 |
| 221 | Tmax | h | 0 | | | | 0 | | 0 |
| 222 | Cmax | ng/ml | 0 | | | | 0 | | 0 |
| 223 | Tlag | h | 0 | | | | 0 | | 0 |
| 224 | Clast_obs/Cmax | | 0 | | | | 0 | | 0 |
| 225 | AUC 0-t | ng/ml * h | 0 | | | | 0 | | 0 |
| 226 | AUC 0-inf_obs | ng/ml * h | 0 | | | | 0 | | 0 |
| 227 | AUC 0-t/0-inf_obs | | 0 | | | | 0 | | 0 |
| 228 | AUMC 0-inf_obs | ng/ml * h^2 | 0 | | | | 0 | | 0 |
| 229 | MRT 0-inf_obs | h | 0 | | | | 0 | | 0 |
| 230 | Vz/F_obs | (mg/kg)/(ng/ml) | 0 | | | | 0 | | 0 |
| 231 | Cl/F_obs | (mg/kg)/(ng/ml)/h | 0 | | | | 0 | | 0 |
| | Dosed as A24 (10 mg/kg, equivalent of Base Structure) Parameters for Parent (Base | | | | | | | | |

-continued

| | BASE STRUCTURE (20 mg/kg) | | | | | | | |
|---|---|---|---|---|---|---|---|---|
| | Parameter | Unit | Animal 1 | Animal 2 | Animal 3 | Animal 4 | Average | Std. Dev. | Combined |

| | Parameter | Unit | Animal 1 | Animal 2 | Animal 3 | Animal 4 | Average | Std. Dev. | Combined |
|---|---|---|---|---|---|---|---|---|---|
| | Structure) following dosing of A24 | | | | | | | | |
| 236 | Lambda_z | 1/h | 0.2216601 | — | 0.6866692 | 0.0645992 | 0.3243095 | 0.3234895 | 0.3 ± 0.3 |
| 237 | t1/2 | h | 3.1270727 | — | 1.009434 | 10.729971 | 4.9554926 | 5.1117072 | 5 ± 5.1 |
| 238 | Tmax | h | 0.5 | 1 | 0.08 | 0.08 | 0.415 | 0.4373786 | 0.4 ± 0.4 |
| 239 | Cmax | ng/ml | 0.351 | 0.287 | 0.217 | 0.218 | 0.26825 | 0.0641632 | 0.3 ± 0.1 |
| 240 | Tlag | h | 0 | 0 | 0 | 0 | 0 | 0 | 0 ± 0 |
| 241 | Clast_obs/Cmax | | 0.3019943 | 0.158885 | 0.4046083 | 0.4284404 | 0.323482 | 0.1226806 | 0.3 ± 0.1 |
| 242 | AUC 0-t | ng/ml * h | 0.530985 | 0.35458 | 0.12241 | 0.616765 | 0.406185 | 0.2184112 | 0.4 ± 0.2 |
| 243 | AUC 0-inf_obs | ng/ml * h | 1.0091947 | | 0.2502736 | 2.0626041 | 1.1073575 | 0.9101442 | 1.1 ± 0.9 |
| 244 | AUC 0-t/0-inf_obs | | 0.5261472 | | 0.4891047 | 0.2990225 | 0.4380915 | 0.1218531 | 0.4 ± 0.1 |
| 245 | AUMC 0-inf_obs | ng/ml * h^2 | 4.9662575 | | 0.3669321 | 36.618365 | 13.983852 | 19.736498 | 14 ± 19.7 |
| 246 | MRT 0-inf_obs | h | 4.9210102 | | 1.4661237 | 17.753463 | 8.0468655 | 8.5818169 | 8 ± 8.6 |
| 247 | Vz/F_obs | (mg/kg)/(ng/ml) | 44.703091 | | 58.188531 | 75.051126 | 59.31425 | 15.205303 | 59.3 ± 15.2 |
| 248 | Cl/F_obs | (mg/kg)/(ng/ml)/h | 9.9088907 | | 39.95627 | 4.8482401 | 18.2378 | 18.978184 | 18.2 ± 19 |
| | Data for Prodrug A24 Dosed as A25 (10 mg/kg, equivalent of Base Structure) Parameters for Parent (Base Structure) following dosing of A25 | | | | | | | | |
| 252 | Lambda_z | 1/h | — | — | — | — | | | |
| 253 | t1/2 | h | — | — | — | — | | | |
| 254 | Tmax | h | 1 | 1 | 1 | 0.5 | 0.875 | 0.25 | 0.9 ± 0.3 |
| 255 | Cmax | ng/ml | 0.503 | 0.678 | 0.513 | 0.503 | 0.54925 | 0.0859627 | 0.5 ± 0.1 |
| 256 | Tlag | h | 0 | 0 | 0 | 0 | 0 | 0 | 0 ± 0 |
| 257 | Clast_obs/Cmax | | 1 | 1 | 1 | 1 | 1 | 0 | 1 ± 0 |
| 258 | AUC 0-t | ng/ml * h | 0.188625 | 0.25425 | 0.192375 | 0.062875 | 0.1745313 | 0.0802895 | 0.2 ± 0.1 |
| 259 | AUC 0-inf_obs | ng/ml * h | — | — | — | — | | | |
| 260 | AUC 0-t/0-inf_obs | | — | — | — | — | | | |
| 261 | AUMC 0-inf_obs | ng/ml * h^2 | — | — | — | — | | | |
| 262 | MRT 0-inf_obs | h | — | — | — | — | | | |
| 263 | Vz/F_obs | (mg/kg)/(ng/ml) | — | — | — | — | | | |
| 264 | Cl/F_obs | (mg/kg)/(ng/ml)/h | — | — | — | — | | | |
| | Data for Prodrug A25 Dosed as A25 (10 mg/kg, equivalent of Base Structure) following dosing of A25 | | | | | | | | |
| 269 | Lambda_z | 1/h | 0.1243062 | 0.0152996 | 0.0061827 | 0.0980479 | 0.0609591 | 0.0590866 | 0.1 ± 0.1 |
| 270 | t1/2 | h | 5.5761279 | 45.304992 | 112.11041 | 7.0694775 | 42.515252 | 49.907149 | 42.5 ± 49.9 |
| 271 | Tmax | h | 0.25 | 0.08 | 0.5 | 0.25 | 0.27 | 0.1730125 | 0.3 ± 0.2 |
| 272 | Cmax | ng/ml | 8.15 | 0.862 | 0.699 | 2.67 | 3.09525 | 3.4861992 | 3.1 ± 3.5 |
| 273 | Tlag | h | 0 | 0 | 0 | 0 | 0 | 0 | 0 ± 0 |
| 274 | Clast_obs/Cmax | | 0.0342331 | 0.3422274 | 0.5035765 | 0.0700375 | 0.2375186 | 0.2244443 | 0.2 ± 0.2 |
| 275 | AUC 0-t | ng/ml * h | 16.15725 | 7.403555 | 11.877475 | 8.2102 | 10.91212 | 4.0022368 | 10.9 ± 4 |
| 276 | AUC 0-inf_obs | ng/ml * h | 18.401708 | 26.685135 | 68.810354 | 10.117432 | 31.003657 | 26.096229 | 31 ± 26.1 |
| 277 | AUC 0-t/0-inf_obs | | 0.8780299 | 0.2774412 | 0.1726117 | 0.8114905 | 0.5348933 | 0.3613762 | 0.5 ± 0.4 |
| 278 | AUMC 0-inf_obs | ng/ml * h^2 | 158.76057 | 1811.7945 | 10702.647 | 123.73178 | 3199.2334 | 5063.9044 | 3199.2 ± 5063.9 |
| 279 | MRT 0-inf_obs | h | 8.6274912 | 67.895273 | 155.53832 | 12.229564 | 61.072662 | 68.572231 | 61.1 ± 68.6 |

-continued

| | BASE STRUCTURE (20 mg/kg) | | | | | | | |
|---|---|---|---|---|---|---|---|---|
| | Parameter | Unit | Animal 1 | Animal 2 | Animal 3 | Animal 4 | Average | Std. Dev. | Combined |
| 280 | Vz/F_obs | (mg/kg)/(ng/ml) | 4.3716877 | 24.49352 | 23.505348 | 10.08072 | 15.612819 | 9.9687179 | 15.6 ± 10 |
| 281 | Cl/F_obs | (mg/kg)/(ng/ml)/h | 0.5434278 | 0.3747405 | 0.145327 | 0.9883931 | 0.5129721 | 0.3564752 | 0.5 ± 0.4 |
| | Data for Prodrug A25 | | | | | | | | |
| 285 | Lambda_z | 1/h | 0.001038 | — | — | — | 0.001038 | | 0.001038 |
| 286 | t1/2 | h | 667.7753 | — | — | — | 667.7753 | | 667.7753 |
| 287 | Tmax | h | 1 | 24 | 4 | 8 | 9.25 | 10.242884 | 9.3 ± 10.2 |
| 288 | Cmax | ng/ml | 4.23 | 4.21 | 4 | 4.28 | 4.18 | 0.1235584 | 4.2 ± 0.1 |
| 289 | Tlag | h | 0 | 0 | 0 | 0 | 0 | 0 | 0 ± 0 |
| 290 | Clast_obs/Cmax | | 0.8888889 | 1 | 0.9625 | 0.885514 | 0.9342257 | 0.0564327 | 0.9 ± 0.1 |
| 291 | AUC 0-t | ng/ml * h | 87.1052 | 93.73835 | 88.82275 | 95.084 | 91.187575 | 3.8273909 | 91.2 ± 3.8 |
| 292 | AUC 0-inf_obs | ng/ml * h | 3709.4746 | — | — | — | 3709.4746 | | 3709.475 |
| 293 | AUC 0-t/0-inf_obs | | 0.0234818 | — | — | — | 0.0234818 | | 0.023482 |
| 294 | AUMC 0-inf_obs | ng/ml * h^2 | 3577773.1 | — | — | — | 3577773.1 | | 3577773 |
| 295 | MRT 0-inf_obs | h | 964.49592 | — | — | — | 964.49592 | | 964.4959 |
| 296 | Vz/F_obs | (mg/kg)/(ng/ml) | 2.5971228 | — | — | — | 2.5971228 | | 2.597123 |
| 297 | Cl/F_obs | (mg/kg)/(ng/ml)/h | 0.0026958 | — | — | — | 0.0026958 | | 0.0026958 |
| | Dosed as A26 (10 mg/kg, equivalent of Base Structure) Parameters for Parent (Base Structure) following dosing of A26 | | | | | | | | |
| 302 | Lambda_z | 1/h | 0.074747 | 0.0804088 | — | — | 0.0775779 | 0.0040035 | 0.1 ± 0 |
| 303 | t1/2 | h | 9.2732385 | 8.6202849 | — | — | 8.9467617 | 0.4617079 | 8.9 ± 0.5 |
| 304 | Tmax | h | 0.25 | 0.08 | 4 | 0.08 | 1.1025 | 1.9333283 | 1.1 ± 1.9 |
| 305 | Cmax | ng/ml | 15.5 | 8.31 | 1.5 | 1.84 | 6.7875 | 6.5995221 | 6.8 ± 6.6 |
| 306 | Tlag | h | 0 | 0 | 0 | 0 | 0 | 0 | 0 ± 0 |
| 307 | Clast_obs/Cmax | | 0.0658065 | 0.07858 | 0.64 | 0.3625 | 0.2867216 | 0.2724423 | 0.3 ± 0.3 |
| 308 | AUC 0-t | ng/ml * h | 22.797 | 11.33965 | 14.321275 | 7.97054 | 14.107116 | 6.347608 | 14.1 ± 6.3 |
| 309 | AUC 0-inf_obs | ng/ml * h | 36.443024 | 19.460647 | — | — | 27.951836 | 12.008354 | 28 ± 12 |
| 310 | AUC 0-t/0-inf_obs | | 0.6255518 | 0.5826965 | — | — | 0.6041241 | 0.0303033 | 0.6 ± 0 |
| 311 | AUMC 0-inf_obs | ng/ml * h^2 | 724.50431 | 430.36668 | — | — | 577.43549 | 207.98671 | 577.4 ± 208 |
| 312 | MRT 0-inf_obs | h | 19.880466 | 22.114716 | — | — | 20.997591 | 1.5798534 | 21 ± 1.6 |
| 313 | Vz/F_obs | (mg/kg)/(ng/ml) | 3.6710606 | 6.3905596 | — | — | 5.0308101 | 1.9297761 | 5 ± 1.9 |
| 314 | Cl/F_obs | (mg/kg)/(ng/ml)/h | 0.2744009 | 0.5138575 | — | — | 0.3941292 | 0.1693214 | 0.4 ± 0.2 |
| | Data for Prodrug A26 | | | | | | | | |
| 318 | Lambda_z | 1/h | 0 | | | | 0 | | 0 |
| 319 | t1/2 | h | 0 | | | | 0 | | 0 |
| 320 | Tmax | h | 0 | | | | 0 | | 0 |
| 321 | Cmax | ng/ml | 0 | | | | 0 | | 0 |
| 322 | Tlag | h | 0 | | | | 0 | | 0 |
| 323 | Clast_obs/Cmax | | 0 | | | | 0 | | 0 |
| 324 | AUC 0-t | ng/ml * h | 0 | | | | 0 | | 0 |
| 325 | AUC 0-inf_obs | ng/ml * h | 0 | | | | 0 | | 0 |
| 326 | AUC 0-t/0-inf_obs | | 0 | | | | 0 | | 0 |
| 327 | AUMC 0-inf_obs | ng/ml * h^2 | 0 | | | | 0 | | 0 |

-continued

| BASE STRUCTURE (20 mg/kg) | | | | | | | | |
|---|---|---|---|---|---|---|---|---|
| Parameter | Unit | Animal 1 | Animal 2 | Animal 3 | Animal 4 | Average | Std. Dev. | Combined |
| 328 MRT 0-inf_obs | h | 0 | | | | 0 | | 0 |
| 329 Vz/F_obs | (mg/kg)/(ng/ml) | 0 | | | | 0 | | 0 |
| 330 Cl/F_obs | (mg/kg)/(ng/ml)/h | 0 | | | | 0 | | 0 |
| Dosed as A27 (10 mg/kg, equivalent of Base Structure) Parameters for Parent (Base Structure) following dosing of A27 | | | | | | | | |
| 335 Lambda_z | 1/h | — | — | 0.0517028 | — | 0.0517028 | | 0.051703 |
| 336 t1/2 | h | — | — | 13.406364 | — | 13.406364 | | 13.40636 |
| 337 Tmax | h | 24 | 24 | 0.5 | 24 | 18.125 | 11.75 | 18.1 ± 11.8 |
| 338 Cmax | ng/ml | 0.72 | 2.13 | 1.55 | 6.68 | 2.77 | 2.6701186 | 2.8 ± 2.7 |
| 339 Tlag | h | 0 | 0 | 0 | 0 | 0 | 0 | 0 ± 0 |
| 340 Clast_obs/Cmax | | 1 | 1 | 0.143871 | 1 | 0.7859677 | 0.4280645 | 0.8 ± 0.4 |
| 341 AUC 0-t | ng/ml * h | 8.586975 | 24.54622 | 4.686395 | 80.391315 | 29.552726 | 34.964384 | 29.6 ± 35 |
| 342 AUC 0-inf_obs | ng/ml * h | — | — | 8.9995036 | — | 8.9995036 | | 8.999504 |
| 343 AUC 0-t/0-inf_obs | | — | — | 0.5207393 | — | 0.5207393 | | 0.520739 |
| 344 AUMC 0-inf_obs | ng/ml * h^2 | — | — | 238.35106 | — | 238.35106 | | 238.3511 |
| 345 MRT 0-inf_obs | h | — | — | 26.484912 | — | 26.484912 | | 26.48491 |
| 346 Vz/F_obs | (mg/kg)/(ng/ml) | — | — | 21.491512 | — | 21.491512 | | 21.49151 |
| 347 Cl/F_obs | (mg/kg)/(ng/ml)/h | — | — | 1.1111724 | — | 1.1111724 | | 1.1111724 |
| Data for Prodrug A27 | | | | | | | | |
| 351 Lambda_z | 1/h | 0 | | | | 0 | | 0 |
| 352 t1/2 | h | 0 | | | | 0 | | 0 |
| 353 Tmax | h | 0 | | | | 0 | | 0 |
| 354 Cmax | ng/ml | 0 | | | | 0 | | 0 |
| 355 Tlag | h | 0 | | | | 0 | | 0 |
| 356 Clast_obs/Cmax | | 0 | | | | 0 | | 0 |
| 357 AUC 0-t | ng/ml * h | 0 | | | | 0 | | 0 |
| 358 AUC 0-inf_obs | ng/ml * h | 0 | | | | 0 | | 0 |
| 359 AUC 0-t/0-inf_obs | | 0 | | | | 0 | | 0 |
| 360 AUMC 0-inf_obs | ng/ml * h^2 | 0 | | | | 0 | | 0 |
| 361 MRT 0-inf_obs | h | 0 | | | | 0 | | 0 |
| 362 Vz/F_obs | (mg/kg)/(ng/ml) | 0 | | | | 0 | | 0 |
| 363 Cl/F_obs | (mg/kg)/(ng/ml)/h | 0 | | | | 0 | | 0 |

We claim:

1. A method for treating a neurogenerative disease in a subject in need thereof, comprising administering to the subject a therapeutically effective amount of a compound of formula (I):

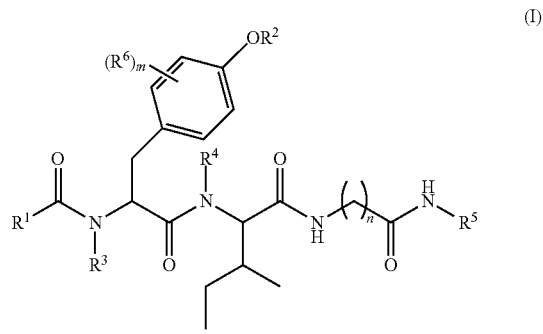

or a tautomer or a pharmaceutically acceptable salt thereof, or a pharmaceutically acceptable salt of the tautomer, wherein:

n is 1, 2, 3, 4, 5, 6, 7, 8, or 9;
m is 0, 1, 2, 3, or 4;
$R^1$ is $C_1$-$C_{12}$ alkyl or $C_1$-$C_{12}$ substituted alkyl;
$R^2$ is selected from

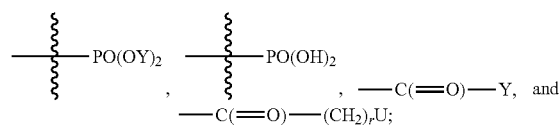

each Y is independently —Z—$(CH_2)_q$—W—$R^b$;
q is 0-4;
Z and W are independently selected from $CH_2$, $NR^c$, and $R^b$,
or Z and W are taken together to form a $C_3$-$C_8$ heterocycloalkyl;
each $R^c$ is independently hydrogen or $C_1$-$C_4$ alkyl;
each $R^b$ is independently selected from hydrogen, $C_1$-$C_{12}$ alkyl, $C_1$-$C_{12}$ substituted alkyl, $C_3$-$C_8$ heterocycloalkyl, and $C_3$-$C_8$ substituted heterocycloalkyl;
r is 0-5;
U is heterocycloalkyl;
$R^3$ and $R^4$ are independently hydrogen or $C_1$-$C_{12}$ alkyl, or $R^3$ and $R^4$ are taken together to form a spirocyclic ring system;
$R^5$ is hydrogen; and
each $R^6$ is independently selected from hydrogen, deuterium, $CH_3$, F, $^{19}$F, and $^{18}$F;
wherein each heterocyclic ring contains up to four heteroatoms selected from O, N, and S;
with the proviso that when both Z and W are heteroatoms, the value of q cannot be 1.

2. The method of claim 1, wherein:
n is 5;
m is 0;
$R^1$ is $C_1$-$C_{12}$ alkyl;
$R^2$ is selected from

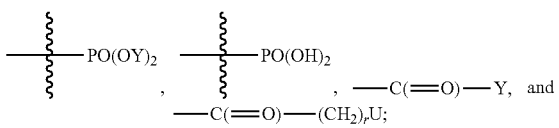

each Y is independently —Z—$(CH_2)_q$—W—$R^b$;
q is 0, 1, or 2;
Z and W are independently selected from $CH_2$, $NR^c$, and $R^b$,
or Z and W are taken together to form a $C_3$-$C_8$ heterocycloalkyl;
each $R^c$ is independently hydrogen or $C_1$-$C_4$ alkyl;
each $R^b$ is independently selected from hydrogen, $C_1$-$C_{12}$ alkyl, $C_1$-$C_{12}$ substituted alkyl, $C_3$-$C_8$ heterocycloalkyl, and $C_3$-$C_8$ substituted heterocycloalkyl;
r is 1;
U is heterocycloalkyl;
$R^3$ and $R^4$ are each hydrogen,
or $R^3$ and $R^4$ are taken together to form a spirocyclic ring system; and
$R^5$ is hydrogen;
wherein each heterocyclic ring contains up to four heteroatoms selected from O and N; and
with the proviso that when both Z and W are heteroatoms, the value of q cannot be 1.

3. The method of claim 2, wherein $R^1$ is $C_5$ alkyl.
4. The method of claim 2, wherein $R^2$ is

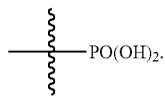

5. The method of claim 4, wherein the compound is a pharmaceutically acceptable salt.
6. The method of claim 2, wherein $R^2$ is

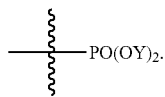

7. The method of claim 2, wherein $R^2$ is —C(=O)—Y.
8. The method of claim 2, wherein $R^2$ is —C(=O)—$(CH_2)_r$U.
9. The method of claim 2, wherein $R^3$ and $R^4$ are each hydrogen.
10. The method of claim 2, wherein $R^3$ and $R^4$ are taken together to form a spirocyclic ring system.
11. The method of claim 2, wherein the compound is a pharmaceutically acceptable salt.
12. The method of claim 1, wherein $R^1$ is $C_1$-$C_{12}$ alkyl.
13. The method of claim 1, wherein $R^1$ is $C_1$-$C_{12}$ alkyl optionally substituted with 1-5 substituents independently selected from alkoxy, cyano, halo, and hydroxy.
14. The method of claim 1, wherein:
$R^1$ is $C_1$-$C_{12}$ alkyl optionally substituted with 1-5 substituents independently selected from alkoxy, cyano, halo, and hydroxy;

each $R^b$ is independently selected from hydrogen; $C_1$-$C_{12}$ alkyl optionally substituted with 1-5 substituents independently selected from alkoxy, cyano, halo, and hydroxy; and $C_3$-$C_8$ heterocycloalkyl optionally substituted with 1-5 substituents selected from $C_1$-$C_6$ alkyl, alkoxy, cyano, halo, hydroxy, and oxo.

15. The method of claim 1, wherein the neurodegenerative disease is Alzheimer's disease, Parkinson's disease, amyotrophic lateral sclerosis, spinal cord injury, traumatic brain injury, sensorineural hearing, or vision loss.

16. The method of claim 15, wherein the neurodegenerative disease is Alzheimer's disease.

17. The method of claim 15, wherein the neurodegenerative disease is Parkinson's disease.

18. A method for treating a neurogenerative disease in a subject in need thereof, comprising administering to the subject a therapeutically effective amount of a compound of formula (II):

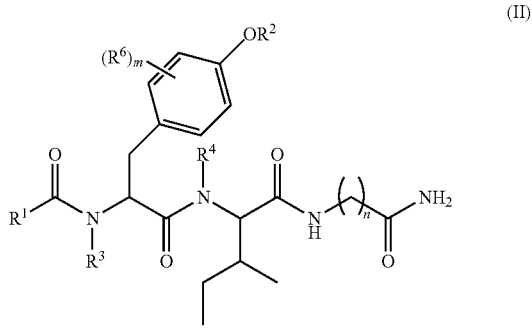

or a tautomer or a pharmaceutically acceptable salt thereof, or a pharmaceutically acceptable salt of the tautomer, wherein:
n is 3, 4, 5, 6, 7, 8, or 9;
m is 0, 1, 2, 3, or 4;
$R^1$ is selected from $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, and $C_2$-$C_{12}$ substituted alkynyl;
$R^2$ is selected from hydrogen,

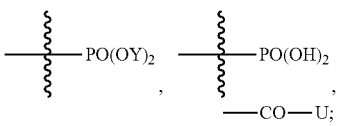

each Y is independently —Z—$(CH_2)_q$—W—$R^b$,
or —C(=O)—Y forms an amide bond through a nitrogen atom on Y, and Y is selected from glycine, sarcosine, N,N-dimethylglycine, alanine, valine, leucine, isoleucine, lysine, ornithine, arginine, serine, and threonine;
q is 0-4;
each Z and W is independently selected from $CH_2$, O, S, $NR^c$, and $R^b$,
or Z and W are taken together to form a $C_3$-$C_8$ heterocycloalkyl or $C_4$-$C_{10}$ heteroaryl or bicyclic ring system in which one of the rings is a $C_4$-$C_{10}$ heteroaryl;
each $R^c$ is independently selected from hydrogen, $C_1$-$C_4$ alkyl, and $C_3$-$C_6$ cycloalkyl;
each $R^b$ is independently selected from hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl;

U is selected from pyridine, 1,4-dihydropyridine, N-alkyl-1,4-dihydropyridine, and C-imidazole, or U is aryl, heteroaryl or heterocycloalkyl;

$R^3$ and $R^4$ are independently selected from hydrogen, $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, and $C_2$-$C_{12}$ substituted alkynyl, or $R^3$ and $R^4$ are taken together to form a fused bicyclic ring system or a spirocyclic ring system; and each $R^6$ is independently selected from hydrogen, deuterium, $CH_3$, F, $^{19}$F, and $^{18}$F;

wherein each heterocyclic and heteroaryl ring contains up to four heteroatoms selected from O, N, and S;

with the proviso that when both Z and W are heteroatoms, the value of q cannot be 1;

and with the proviso that when $R^2$ is hydrogen, at least one of the $R^3$ or $R^4$ groups is not hydrogen.

19. The method of claim 18, wherein:

$R^1$ is selected from $C_1$-$C_{12}$ alkyl optionally substituted with 1-5 substituents independently selected from alkoxy, cyano, halo, and hydroxy; $C_2$-$C_{12}$ alkenyl optionally substituted with 1-5 substituents independently selected from alkoxy, cyano, halo, and hydroxy; and $C_2$-$C_{12}$ alkynyl optionally substituted with 1-5 substituents independently selected from alkoxy, cyano, halo, and hydroxy;

each $R^b$ is independently selected from hydrogen; $C_1$-$C_{12}$ alkyl optionally substituted with 1-5 substituents independently selected from alkoxy, cyano, halo, and hydroxy; $C_3$-$C_8$ cycloalkyl optionally substituted with 1-5 substituents selected from $C_1$-$C_6$ alkyl, alkoxy, cyano, halo, hydroxy, and oxo; and $C_3$-$C_8$ heterocycloalkyl optionally substituted with 1-5 substituents selected from $C_1$-$C_6$ alkyl, alkoxy, cyano, halo, hydroxy, and oxo; and $R^3$ and $R^4$ are independently selected from hydrogen; $C_1$-$C_{12}$ alkyl optionally substituted with 1-5 substituents independently selected from alkoxy, cyano, halo, and hydroxy; $C_2$-$C_{12}$ alkenyl optionally substituted with 1-5 substituents independently selected from alkoxy, cyano, halo, and hydroxy; and $C_2$-$C_{12}$ alkynyl optionally substituted with 1-5 substituents independently selected from alkoxy, cyano, halo, and hydroxy.

20. The method of claim 18, wherein the compound is of formula (III):

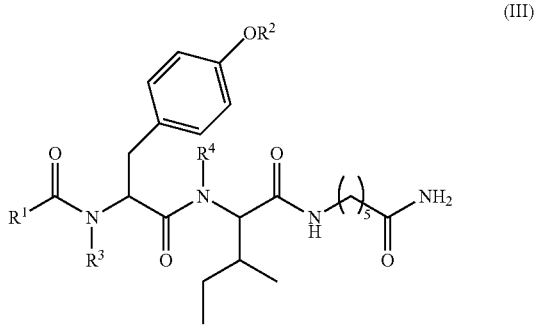

(III)

or a tautomer or a pharmaceutically acceptable salt thereof, or a pharmaceutically acceptable salt of the tautomer, wherein:

$R^1$ is a $C_1$-$C_{12}$ alkyl or $C_1$-$C_{12}$ substituted alkyl;

$R^2$ is selected from hydrogen,

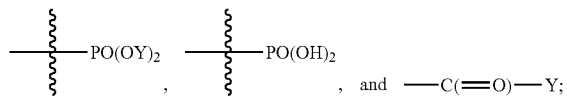

each Y is independently $-Z-(CH_2)_q-W-R^b$;

q is 0-4;

Z and W are independently selected from $CH_2$, O, S, $NR^c$, and $R^b$, or Z and W are taken together to form a $C_3$-$C_8$ heterocycloalkyl or $C_4$-$C_{10}$ heteroaryl or bicyclic ring system in which one of the rings is a $C_4$-$C_{10}$ heteroaryl;

each $R^c$ is independently selected from hydrogen, $C_1$-$C_4$ alkyl, and $C_3$-$C_6$ cycloalkyl;

each $R^b$ is independently selected from hydrogen, $C_1$-$C_{12}$ alkyl, $C_1$-$C_{12}$ substituted alkyl, $C_3$-$C_8$ cycloalkyl, $C_3$-$C_8$ substituted cycloalkyl, $C_3$-$C_8$ heterocycloalkyl, and $C_3$-$C_8$ substituted heterocycloalkyl; and $R^3$ and $R^4$ are independently selected from hydrogen, $C_1$-$C_{12}$ alkyl, $C_1$-$C_{12}$ substituted alkyl, $C_2$-$C_{12}$ alkenyl, $C_2$-$C_{12}$ substituted alkenyl, $C_2$-$C_{12}$ alkynyl, and $C_2$-$C_{12}$ substituted alkynyl, or $R^3$ and $R^4$ are taken together to form a fused bicyclic ring system or a spirocyclic ring system, wherein the fused ring is $C_3$-$C_8$ heterocycloalkyl, $C_6$-$C_{10}$ aryl, or $C_4$-$C_{10}$ heteroaryl;

wherein each heterocyclic and heteroaryl ring contains up to four heteroatoms selected from O, N, and S;

with the proviso that when both Z and W are heteroatoms, the value of q cannot be 1;

and with the proviso that when $R^2$ is hydrogen, at least one of the $R^3$ or $R^4$ groups is not hydrogen.

21. The method of claim 20, wherein:
$R^1$ is a $C_1$-$C_{12}$ alkyl;
$R^2$ is $-C(=O)-Y$; and
$R^3$ and $R^4$ are each hydrogen.

22. The method of claim 20, wherein:
$R^1$ is a $C_1$-$C_{12}$ alkyl;
$R^2$ is $-C(=O)-CH(NH_2)^iPr$; and
$R^3$ and $R^4$ are each hydrogen.

23. The method of claim 20, wherein:
$R^1$ is a $C_1$-$C_{12}$ alkyl;
$R^2$ is $-C(=O)-CH(NH_2)^iPr$;
$R^3$ and $R^4$ are each hydrogen;
m is 1 or 2; and
$R^6$ is F.

24. The method of claim 20, wherein:
$R^1$ is a $C_1$-$C_{12}$ alkyl;
$R^2$ is

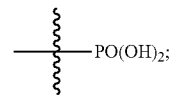

and
$R^3$ and $R^4$ are each hydrogen.

25. The method of claim 18, wherein:
m is 0;
$R^1$ is a $C_1$-$C_{12}$ alkyl; and
$R^3$ and $R^4$ are taken together to form a spirocyclic ring system.

26. The method of claim 18, wherein:
m is 1 or 2;
$R^1$ is a $C_1$-$C_{12}$ alkyl;
$R^3$ and $R^4$ are taken together to form a spirocyclic ring system; and
$R^6$ is selected from hydrogen, deuterium, F, $^{19}$F, and $^{18}$F.

27. The method of claim 18, wherein the neurodegenerative disease is Alzheimer's disease, Parkinson's disease, amyotrophic lateral sclerosis, spinal cord injury, traumatic brain injury, sensorineural hearing, or vision loss.

28. The method of claim 27, wherein the neurodegenerative disease is Alzheimer's disease.

29. The method of claim 27, wherein the neurodegenerative disease is Parkinson's disease.

30. A method for treating a neurogenerative disease in a subject in need thereof, comprising administering to the subject a therapeutically effective amount of a compound selected from:

1

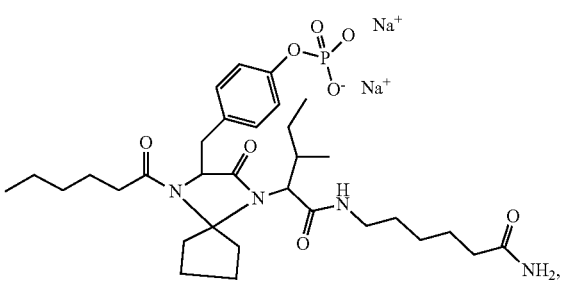

2

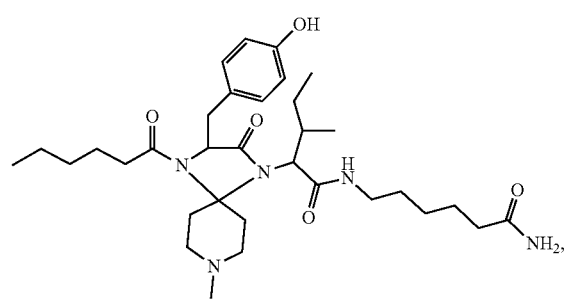

3

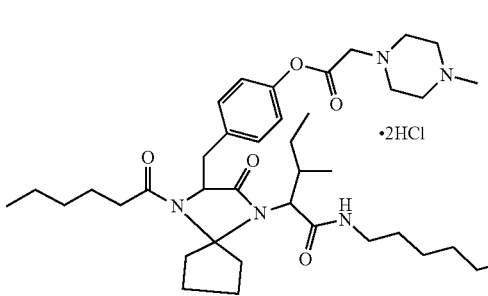

4

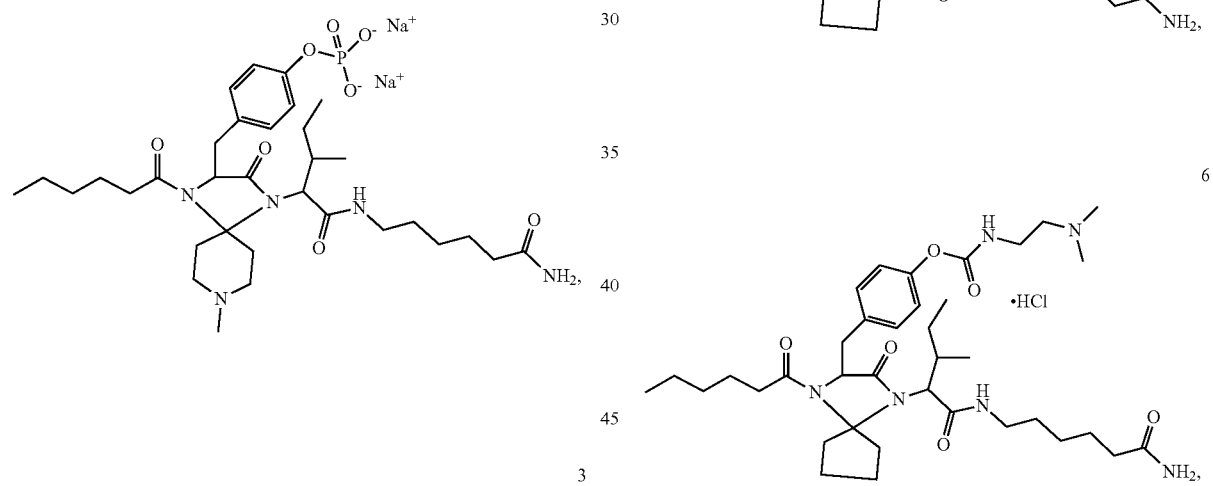

5

6

7

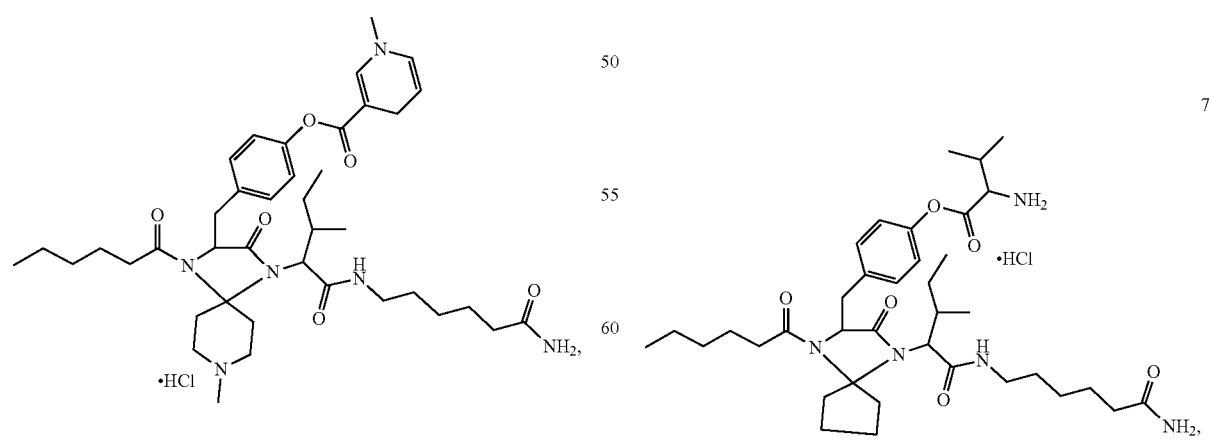

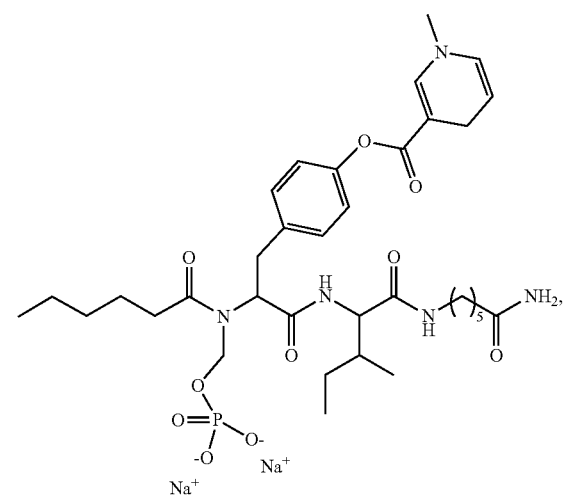
9
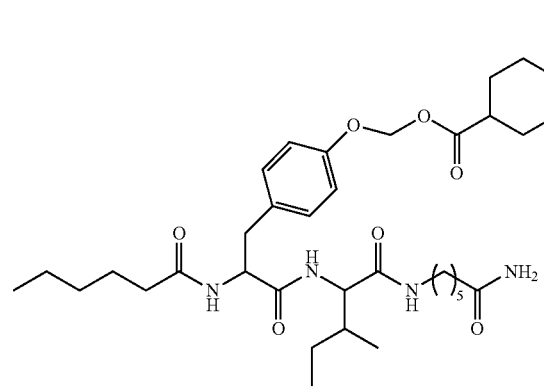
A17a
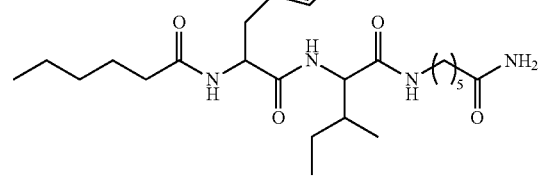
A17b
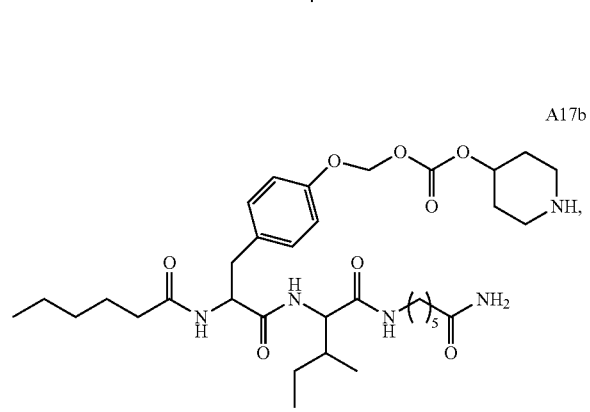
A17c
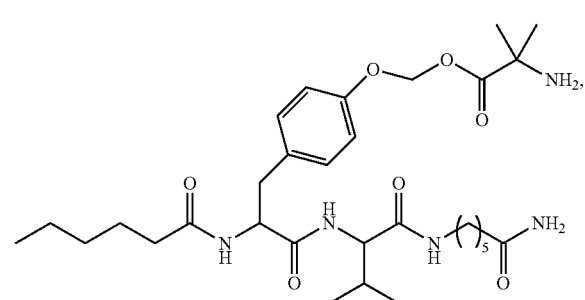
A17e
A17f
A17g
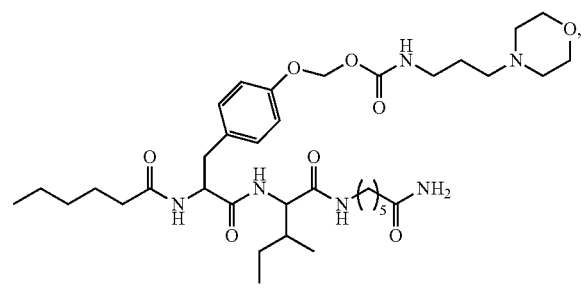
A17h
A17i A17j
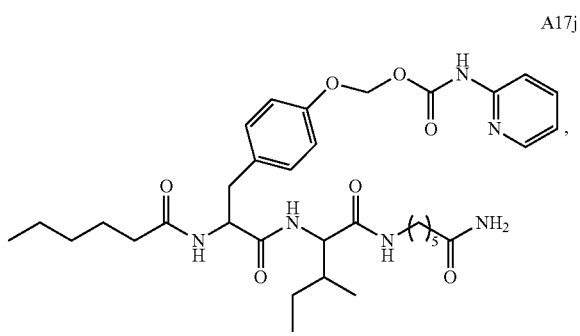
A17k
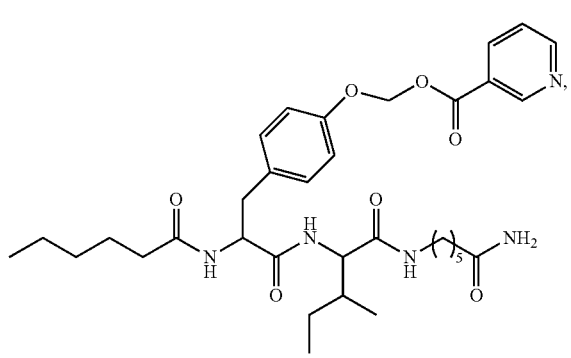
A17l
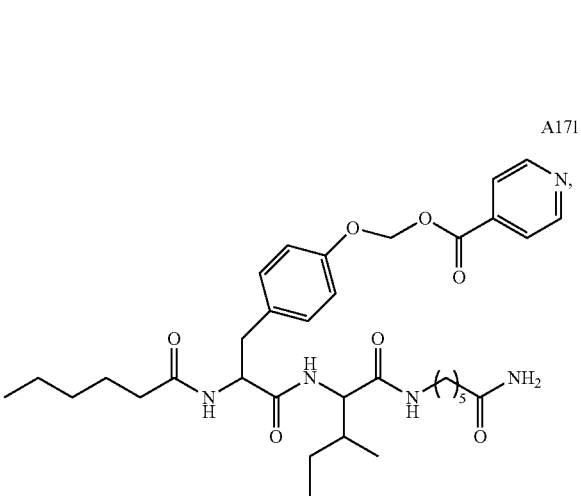
A17m
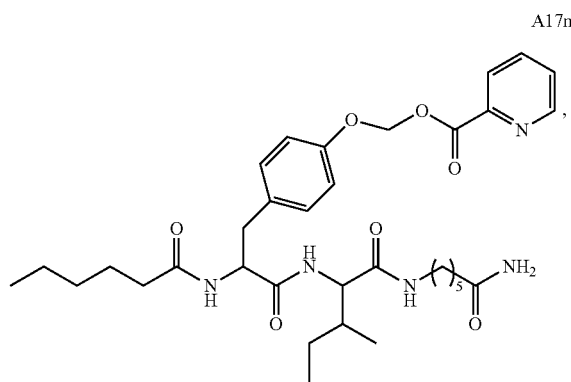
A18
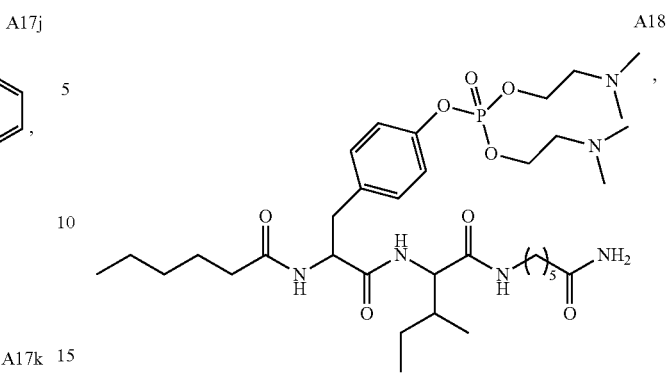
A19
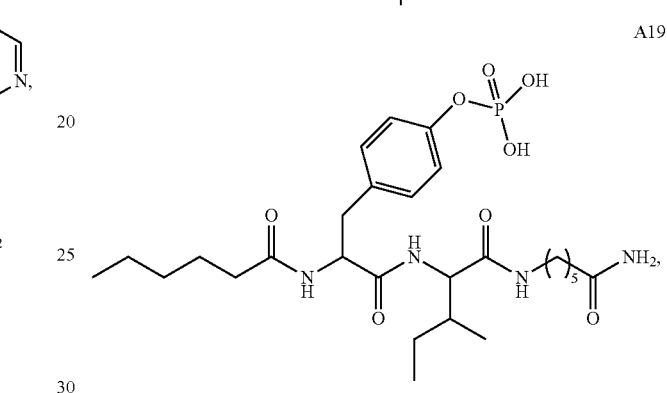
A20
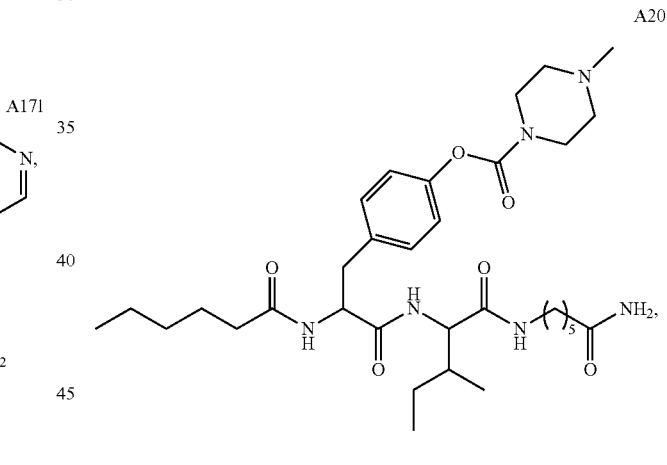
A21
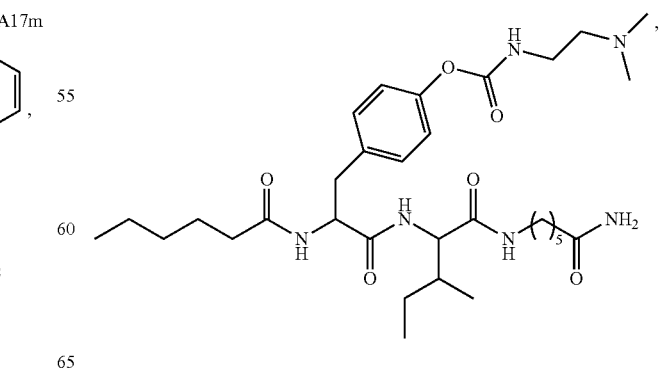

-continued

A22
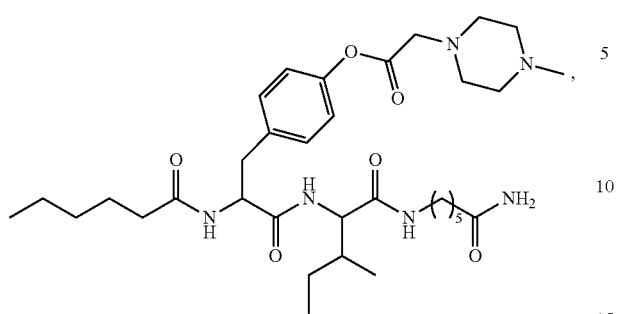

A23
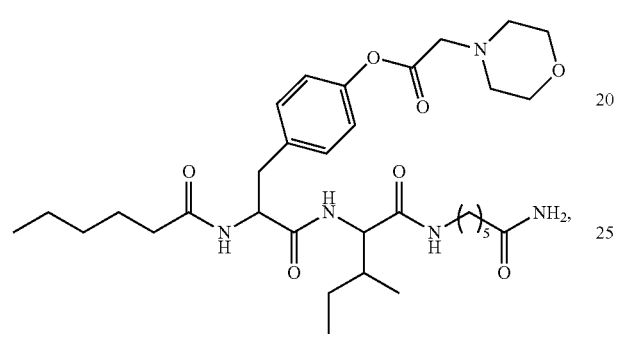

A24
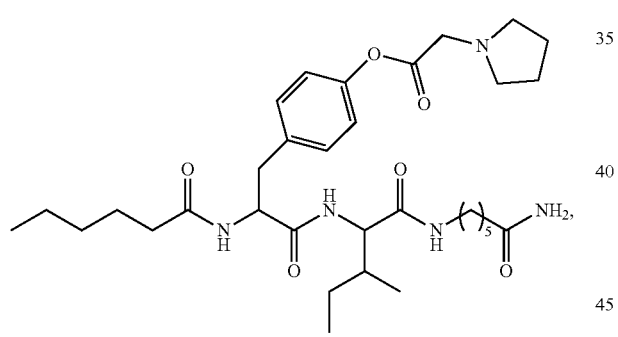

A25
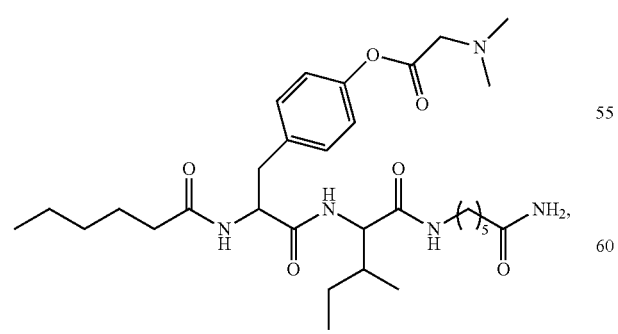

-continued

A26
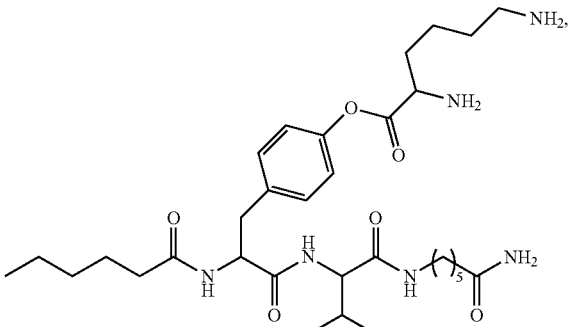

and

A27
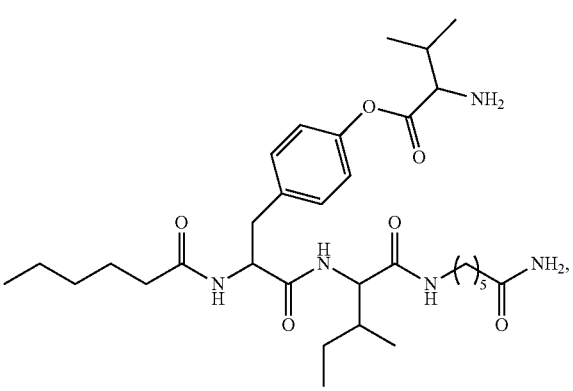

or a tautomer or a pharmaceutically acceptable salt thereof, or a pharmaceutically acceptable salt of the tautomer.

31. The method of claim 30, wherein the compound is:

A21
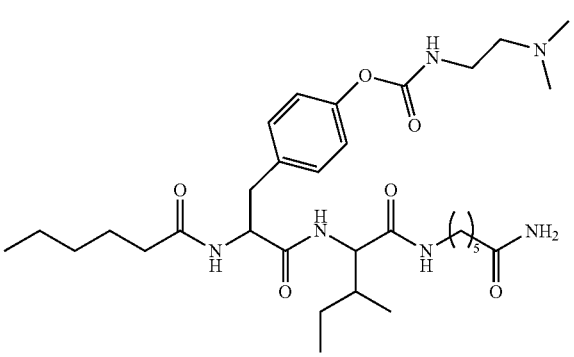

or a pharmaceutically acceptable salt thereof.

32. The method of claim 31, wherein the neurodegenerative disease is Alzheimer's disease, Parkinson's disease, amyotrophic lateral sclerosis, spinal cord injury, traumatic brain injury, sensorineural hearing, or vision loss.

33. The method of claim 32, wherein the neurodegenerative disease is Alzheimer's disease.

34. The method of claim 32, wherein the neurodegenerative disease is Parkinson's disease.

35. The method of claim 30, wherein the compound is:

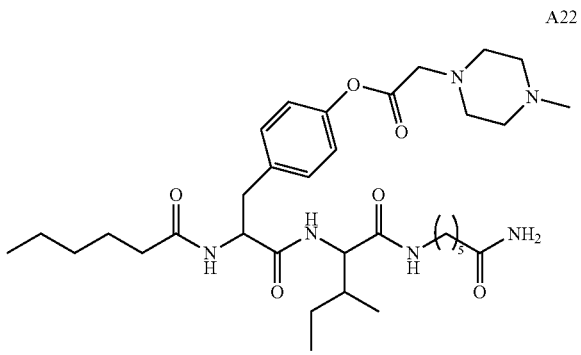
A22 or a pharmaceutically acceptable salt thereof.

36. The method of claim 35, wherein the neurodegenerative disease is Alzheimer's disease, Parkinson's disease, amyotrophic lateral sclerosis, spinal cord injury, traumatic brain injury, sensorineural hearing, or vision loss.

37. The method of claim 36, wherein the neurodegenerative disease is Alzheimer's disease.

38. The method of claim 36, wherein the neurodegenerative disease is Parkinson's disease.

39. The method of claim 30, wherein the compound is:

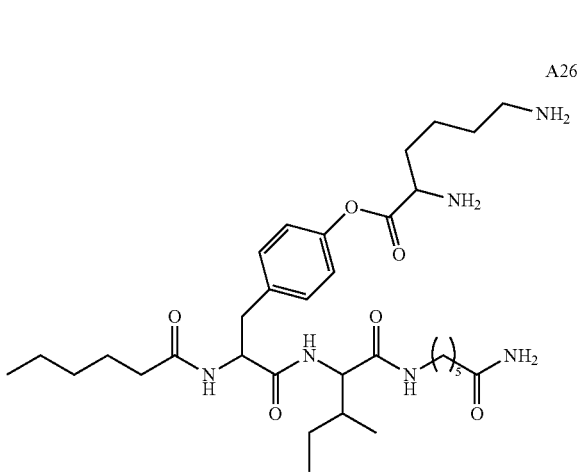
A26 or a pharmaceutically acceptable salt thereof.

40. The method of claim 39, wherein the neurodegenerative disease is Alzheimer's disease, Parkinson's disease, amyotrophic lateral sclerosis, spinal cord injury, traumatic brain injury, sensorineural hearing, or vision loss.

41. The method of claim 40, wherein the neurodegenerative disease is Alzheimer's disease.

42. The method of claim 40, wherein the neurodegenerative disease is Parkinson's disease.

43. The method of claim 30, wherein the compound is:

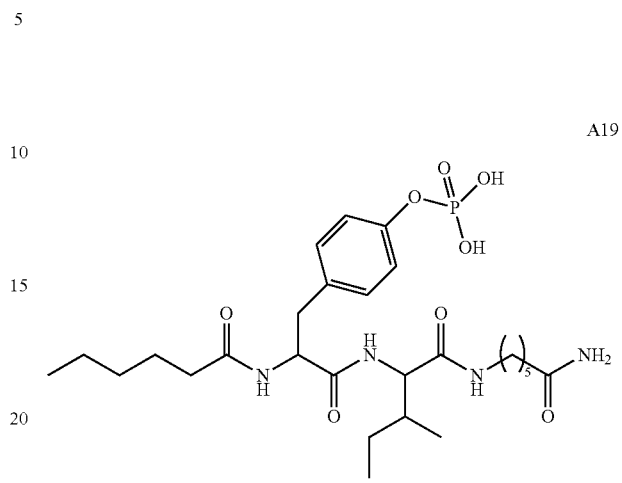
A19 or a pharmaceutically acceptable salt thereof.

44. The method of claim 43, wherein the compound is:

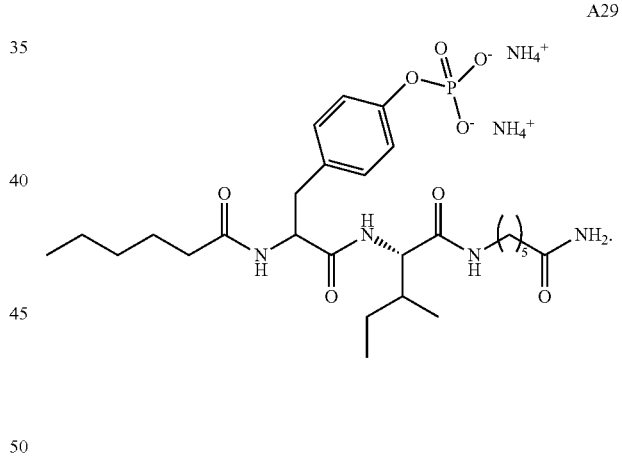
A29

45. The method of claim 44, wherein the neurodegenerative disease is Alzheimer's disease, Parkinson's disease, amyotrophic lateral sclerosis, spinal cord injury, traumatic brain injury, sensorineural hearing, or vision loss.

46. The method of claim 45, wherein the neurodegenerative disease is Alzheimer's disease.

47. The method of claim 45, wherein the neurodegenerative disease is Parkinson's disease.

48. The method of claim 43, wherein the neurodegenerative disease is Alzheimer's disease, Parkinson's disease, amyotrophic lateral sclerosis, spinal cord injury, traumatic brain injury, sensorineural hearing, or vision loss.

49. The method of claim 48, wherein the neurodegenerative disease is Alzheimer's disease.

50. The method of claim 48, wherein the neurodegenerative disease is Parkinson's disease.

51. The method of claim 43, wherein the compound is:

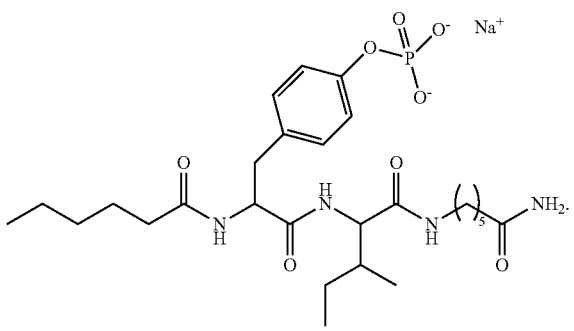

A30

52. The method of claim 51, wherein the neurodegenerative disease is Alzheimer's disease, Parkinson's disease, amyotrophic lateral sclerosis, spinal cord injury, traumatic brain injury, sensorineural hearing, or vision loss.

53. The method of claim 52, wherein the neurodegenerative disease is Alzheimer's disease.

54. The method of claim 52, wherein the neurodegenerative disease is Parkinson's disease.

55. The method of claim 30, wherein the neurodegenerative disease is Alzheimer's disease, Parkinson's disease, amyotrophic lateral sclerosis, spinal cord injury, traumatic brain injury, sensorineural hearing, or vision loss.

56. The method of claim 55, wherein the neurodegenerative disease is Alzheimer's disease.

57. The method of claim 55, wherein the neurodegenerative disease is Parkinson's disease.

* * * * *